United States Patent
Collazo

(10) Patent No.: US 10,357,255 B2
(45) Date of Patent: Jul. 23, 2019

(54) GLOBALIZED TOTAL KNEE INSTRUMENTATION

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 240 days.

(21) Appl. No.: 15/290,741

(22) Filed: Oct. 11, 2016

(65) Prior Publication Data

US 2017/0100132 A1    Apr. 13, 2017

Related U.S. Application Data

(60) Provisional application No. 62/238,922, filed on Oct. 8, 2015.

(51) Int. Cl.
*A61B 17/17* (2006.01)
*A61B 17/15* (2006.01)
*A61B 17/14* (2006.01)
*A61B 17/56* (2006.01)

(52) U.S. Cl.
CPC ............ *A61B 17/15* (2013.01); *A61B 17/142* (2016.11); *A61B 17/155* (2013.01); *A61B 2017/564* (2013.01)

(58) Field of Classification Search
CPC .................... A61B 17/15–158; A61B 17/1764
See application file for complete search history.

(56) References Cited

U.S. PATENT DOCUMENTS

| | | | |
|---|---|---|---|
| 4,703,751 A * | 11/1987 | Pohl | A61B 17/155 606/53 |
| 4,825,857 A | 5/1989 | Kenna | |
| 4,907,578 A | 3/1990 | Petersen | |
| 5,342,368 A | 8/1994 | Petersen | |
| 5,454,816 A | 10/1995 | Ashby | |
| 5,624,444 A | 4/1997 | Wixon et al. | |
| 5,662,656 A * | 9/1997 | White | A61B 17/155 606/86 R |
| 5,683,397 A | 11/1997 | Vendrely et al. | |
| 5,720,752 A * | 2/1998 | Elliott | A61B 17/155 606/79 |
| 5,776,137 A * | 7/1998 | Katz | A61B 17/155 606/102 |
| 5,830,216 A | 11/1998 | Insall et al. | |
| 6,173,200 B1 | 1/2001 | Cooke et al. | |

(Continued)

OTHER PUBLICATIONS

Smith & Nephew, Journey II BCS, Bi-Cruciate Stabilized Knee System, Surgical Technique—Summary, pp. 1-2, 2013.

*Primary Examiner* — Zade Coley
(74) *Attorney, Agent, or Firm* — Lerner, David, Littenberg, Krumholz & Mentlik, LLP

(57) ABSTRACT

A varus-valgus alignment instrument includes a body having a bone contact surface for contacting a distal femur and an opening extending through the body and bone contact surface. The opening is sized to receive an elongate shaft therein. An alignment member is moveably attached to the body and has first and second openings therethrough. The first and second openings are sized to receive the elongate shaft and are interchangeably positioned in alignment with the opening of the body.

7 Claims, 44 Drawing Sheets

(56) References Cited

U.S. PATENT DOCUMENTS

| | | | |
|---|---|---|---|
| 6,740,092 B2 | 5/2004 | Lombardo et al. | |
| 7,241,298 B2 | 7/2007 | Nemec et al. | |
| 7,309,339 B2 | 12/2007 | Cusick et al. | |
| 7,377,924 B2 | 5/2008 | Raistrick et al. | |
| 8,070,752 B2 | 12/2011 | Metzger et al. | |
| 8,157,869 B2 | 4/2012 | Metzger et al. | |
| 8,163,028 B2 | 4/2012 | Metzger et al. | |
| 8,187,280 B2 * | 5/2012 | May | A61B 17/1764 606/88 |
| 8,192,441 B2 * | 6/2012 | Collazo | A61B 17/151 606/86 R |
| 8,231,630 B2 | 7/2012 | Long et al. | |
| 8,277,455 B2 | 10/2012 | Couture et al. | |
| 8,328,873 B2 | 12/2012 | Metzger et al. | |
| 8,480,751 B2 | 7/2013 | Metzger et al. | |
| 8,506,571 B2 | 8/2013 | Chana et al. | |
| 8,562,616 B2 * | 10/2013 | May | A61B 17/155 606/88 |
| 8,801,715 B2 | 8/2014 | Sato | |
| 8,834,473 B2 | 9/2014 | Dees, Jr. et al. | |
| 8,926,618 B2 * | 1/2015 | Collazo | A61B 17/152 606/87 |
| 8,936,648 B2 | 1/2015 | Collard et al. | |
| 9,005,208 B2 | 4/2015 | Teeny et al. | |
| 9,089,343 B2 | 7/2015 | Dees, Jr. et al. | |
| 9,113,923 B2 | 8/2015 | Fox et al. | |
| 9,119,635 B2 | 9/2015 | Booth et al. | |
| 9,131,945 B2 | 9/2015 | Aram et al. | |
| 9,204,884 B2 | 12/2015 | Dees et al. | |
| 9,204,897 B2 | 12/2015 | Jones et al. | |
| 9,237,958 B2 | 1/2016 | Duggal et al. | |
| 2004/0172044 A1 | 9/2004 | Grimm et al. | |
| 2004/0220583 A1 * | 11/2004 | Pieczynski, II | A61B 17/1764 606/102 |
| 2008/0058949 A1 | 3/2008 | Dees et al. | |
| 2009/0125114 A1 | 5/2009 | May et al. | |
| 2009/0204115 A1 | 8/2009 | Dees, Jr. et al. | |
| 2010/0094301 A1 | 4/2010 | Dees et al. | |
| 2010/0234850 A1 | 9/2010 | Dees, Jr. et al. | |
| 2011/0060340 A1 | 3/2011 | Dees, Jr. et al. | |
| 2011/0184421 A1 | 7/2011 | Dees, Jr. et al. | |
| 2012/0053591 A1 | 3/2012 | Haines et al. | |
| 2012/0136359 A1 | 5/2012 | Grunder et al. | |
| 2013/0158556 A1 | 6/2013 | Jones et al. | |
| 2013/0178859 A1 | 7/2013 | Fox et al. | |
| 2013/0317501 A1 | 11/2013 | Booth et al. | |
| 2013/0338671 A1 | 12/2013 | Beedall et al. | |
| 2014/0039507 A1 | 2/2014 | Metzger | |
| 2014/0074095 A1 | 3/2014 | Long et al. | |
| 2014/0114318 A1 | 4/2014 | May et al. | |
| 2014/0180294 A1 | 6/2014 | Collins | |
| 2014/0194883 A1 | 7/2014 | Jones et al. | |
| 2014/0243835 A1 | 8/2014 | Teeny et al. | |
| 2014/0257308 A1 | 9/2014 | Johannaber | |
| 2014/0257309 A1 | 9/2014 | Aram et al. | |
| 2014/0336659 A1 | 11/2014 | Emslie et al. | |
| 2015/0100059 A1 | 4/2015 | Chana et al. | |
| 2015/0238202 A1 | 8/2015 | Collins et al. | |
| 2015/0359642 A1 | 12/2015 | Claypool et al. | |
| 2015/0374388 A1 | 12/2015 | Aram et al. | |
| 2016/0030053 A1 | 2/2016 | Yager et al. | |
| 2016/0051265 A1 | 2/2016 | Jones et al. | |
| 2016/0128702 A1 | 5/2016 | Grant et al. | |

* cited by examiner

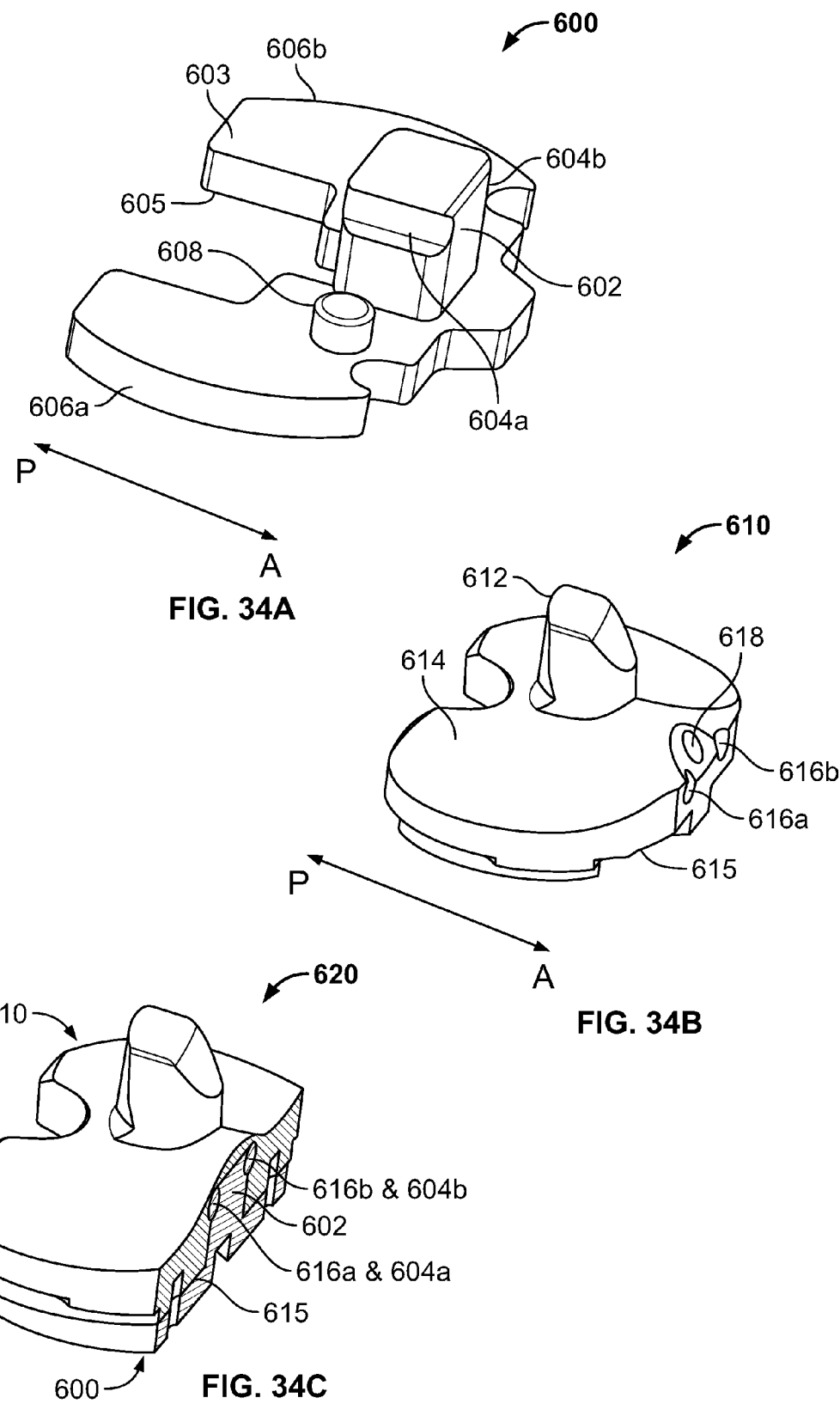

GLOBALIZED TOTAL KNEE INSTRUMENTATION

CROSS-REFERENCE TO RELATED APPLICATIONS

This application claims the benefit of the filing date of U.S. Provisional Patent Application No. 62/238,922 filed Oct. 8, 2015, the disclosure of which is hereby incorporated herein by reference.

BACKGROUND OF THE INVENTION

Total knee arthroplasty (TKA) or total knee replacement is a common orthopedic procedure in which damaged or diseased articular cartilage and/or bone of the knee is replaced with prosthetic components. Prior to implanting such prosthetic components, a surgeon generally resects a portion of the patient's native bone in order to shape the bone to receive the prosthetic components. For example, a surgeon might make one or more planar cuts at a distal end of a femur and proximal end of a tibia so that corresponding surfaces of femoral and tibial prosthetic components can be respectively attached thereto.

Each individual cut removal of a section of bone is carefully made. Once native bone is resected from a joint, it is gone forever. In addition, the amount of bone resected and the final geometries of the resected bone significantly influence the fit and alignment of the prosthetic components. Improper fit and/or alignment can result in instability of the joint, increased risk of bone fracture and component failure, pain, and reduced range of motion.

Multiple resection philosophies/techniques have emerged over the years to help ensure proper fit and alignment of the prosthetic components comprising the artificial joint. For example, mechanical axis alignment, anatomic axis alignment, gap balancing, measured resection, anterior referencing, and posterior referencing are some of the various techniques/philosophies that have been widely adopted for forming bone in a TKA procedure.

Surgeons often prefer one technique/philosophy over another. To accommodate surgeon preference, numerous instrument sets have been made available to help guide each cut of a femur and tibia in accordance with a particular technique/philosophy often to the exclusion of other techniques/philosophies. These instruments typically guide a saw blade or other cutting tool to cut a bone at a particular angle and to remove a particular amount of bone. Although, a certain amount of preoperative planning using radiographic images helps a surgeon plan each cut of a joint surface, the actual amount of bone removed and the angle of each cut is often unknown until the TKA procedure is well under way. As such, many instrument sets provide instruments with complicated mechanisms or duplicate instruments that are designed to remove different amounts of bone and guide a cut at different relative angles as needed during the procedure.

The result is that a single manufacturer may provide different sets of instruments for performing the various resection philosophies/techniques with each set including a large quantity of instruments. Prior to a TKA procedure, a surgeon or healthcare facility may order a set of instruments for performing the procedure according to the surgeon's preferred technique/philosophy. These instruments may be stored, sterilized, packaged, and shipped by the manufacturer to the healthcare facility in which the procedure is to take place. In some instances, the instruments may be stored and sterilized at the healthcare facility itself.

The demands of manufacturing, storing, maintaining, sterilizing, packaging, shipping and tracking such a diverse, complicated and large quantity of instruments can be expensive, particularly in a world that is increasingly demanding cheaper surgical procedures. For example, a set of instruments for performing a TKA procedure may cost about 40,000 USD to manufacture. These instruments may then be placed into circulation and are often only provided to a few surgeons who subscribe to the technique/philosophy for which the instrument set was designed. While in circulation, these instruments must be stored, repaired, sterilized, packaged and shipped numerous times over contributing to the overall costs of the instruments. The more instruments provided in each set, the greater the life-cycle costs become, which may reflect back to the cost of the TKA procedure.

Therefore, further improved instruments for use in TKA procedures are desired.

BRIEF SUMMARY OF THE INVENTION

Described herein are devices, systems, and methods for performing TKA. In particular, various devices are disclosed that may be provided in a set or sets of devices for performing a TKA procedure according to many resection philosophies/techniques. In addition, these devices consolidate functions typically performed by multiple other existing devices using easy to operate and durable mechanisms. Such easy to operate and durable mechanisms are generally designed to be easily disassembled for sterilization and to avoid the use of certain elements, such as ball detents, that are a frequent point of failure in presently existing devices. The combination of the described devices can reduce life-cycle costs from current devices by about half.

In one aspect of the present disclosure, a bone resection guide, includes a body having first and second guide surfaces defining a first slot, and a shim moveably connected to the body and disposed within the first slot so that the shim can move towards and away from the first and second guide surfaces. The shim has a thickness smaller than a distance between the first and second guide surface.

In another aspect of the present disclosure, a varus-valgus alignment instrument includes a body having a bone contact surface for contacting a distal femur and an opening extending through the body and bone contact surface. The opening is sized to receive an elongate shaft therein. An alignment member is moveably attached to the body and has first and second openings therethrough. Each of the first and second openings is sized to receive the elongate shaft and is interchangeably positioned in alignment with the opening of the body.

In a further aspect of the present disclosure, a bone forming assembly includes a reference guide having a reference body and an alignment member. The reference body has a bone contact surface and a reference opening extending through the reference body and bone contact surface. The alignment member has first and second openings extending therethrough and is adjustably mounted to the reference body such that the first and second openings are interchangeably aligned with the reference opening. A resection guide has a resection body and an engagement member connected to the resection body and the reference body. The resection body has a first resection surface that aligns with the bone contact surface when the resection guide is connected to the reference guide.

In an additional aspect of the present disclosure, a femoral sizing guide assembly includes a first body having a first plate portion extending therefrom and has a first resection guide surface extending in a direction transverse to the first plate portion. A second body portion has a second plate portion extending therefrom and has a second resection guide surface extending in a direction transverse to the second plate portion. The second plate portion has a bone contact surface and a recess extending through an upper surface thereof in a direction toward the second resection guide surface. The recess is dimensioned to slidingly receive the first plate portion.

In yet a further aspect of the present disclosure, a posterior condylar reference guide includes a first body having first and second arms extending therefrom and a first reference surface for contacting a posterior condyle. The first and second arms at least partially define a space therebetween and are moveable between a first and second position. A second body is disposed within the space and has first and second guide openings extending therethrough. The second body is rotatable within the space when the first and second arms are in the second position and is prohibited from rotating when in the first position.

In still a further aspect of the present disclosure, a multipurpose handle includes a body having a first end configured to connect to a first instrument, and a channel extending through the body in a direction transverse to a longitudinal axis thereof. The body includes an extension extending into the channel for receipt into an opening of a second instrument.

In another aspect of the present disclosure, a tibial resection guide assembly includes an ankle clamp having a clamp member and an elongate shaft extending from the clamp member. The resection guide also includes a guide block having first and second members connected by an intermediate member. The first and second members are connectable to the elongate shaft and each have an abutment surface. An elongate member has first and second ends. The first end is slidably connectable to the elongate shaft between the first and second members of the adjustable guide block. A resection block is connectable to a first end of the elongate member and has a resection guide surface, wherein, when assembled, abutting the abutment surface of the first member with the first end of the elongate member positions the resection guide surface at a first angle with respect to a tibia, and abutting the abutment surface of the second member with the first end of the elongate member positions the resection guide surface at a second angle with respect to the tibia.

In an additional aspect of the present disclosure, a method of forming a femur for receipt of a prosthesis includes inserting an elongate member into an intramedullary canal of the femur. Also included in the method is determining a desired varus-valgus angle of a distal resected surface of the femur selecting between first and second alignment holes of an alignment member based the desired varus-valgus angle. The first and second alignment holes each corresponding to a different varus-valgus angle. The method further includes inserting the elongate member into the selected alignment hole and a through-hole in a body. The alignment member and body are connected and comprise a distal reference guide. The method additionally includes cutting the femur along a resection guide surface of a cutting guide connected to the distal reference guide.

In a further aspect of the present disclosure, a method of resecting a femur includes determining a desired amount of bone to be resected; selecting between first and second sides of a moveable shim disposed within a slot of a cutting guide based on the desired amount of bone to be resected, the first side of the shim corresponding to a first depth of resection, the second side of the shim corresponds to a second depth of resection; placing the cutting guide against the femur; and resecting the femur through the slot on the selected side of the moveable shim.

In an even further aspect of the present disclosure, a method of locating guide pins in a femur includes contacting a distal resected surface of a femur with a bone contact surface of a reference guide; contacting a posterior condyle with a first reference surface of the reference guide; moving a pair of arms extending from a first body of the reference guide from a first position to a second position to release a second body of the reference guide; rotating the second body from a first orientation to a second orientation; moving the pair of arms from the second position to the first position to lock the second body in the second orientation; and inserting guide pins through corresponding guide holes disposed within the second body.

In still a further aspect of the present disclosure, a method of using a multipurpose handle includes inserting an extension extending into a channel of a handle into an opening disposed within an end of a reamer such that a longitudinal axis of the reamer is transverse to a longitudinal axis of the handle; reaming an intramedullary canal of a femur by applying torque thereto via the handle; disconnecting the handle from reamer; and connecting a first end of the handle to a tibial baseplate.

In an additional aspect of the present disclosure, a method of adjusting a posterior slope of a proximal tibial resection includes connecting a first end of an elongate member at a proximal end of a tibia, the first end has a resection guide includes a resection guide surface attached thereto; connecting a second end of the elongate member to a distal end of the tibia via an ankle clamp, the ankle clamp includes an extension extending therefrom, the second end of the elongate member is moveably connected to the extension between a first abutment surface and second abutment surface of a reference block; abutting the first abutment surface of the reference block with the second end of the elongate member to position the resection guide surface at a first orientation relative to the tibia; and abutting the second abutment surface with the second end of the elongate member to position the resection guide surface at a second orientation relative to the tibia.

In an even further aspect of the present disclosure, a method of resecting a femur includes determining a varus-valgus angle for an implanted artificial knee prosthesis; selecting a first reference opening of an alignment member of a reference guide from a plurality of reference openings of the alignment member each corresponding to a different varus-valgus angle; rotating the alignment member relative to a reference body of the reference guide to a position in which the first reference opening aligns with a body opening of the reference body, the first opening and body opening forming an axis, the axis being angled relative to a reference surface of the reference body corresponding to the determined varus-valgus angle; positioning an intramedullary rod through the first opening and body opening; inserting the intramedullary rod into the femur; positioning the reference surface of the reference guide adjacent the femur; and resecting the femur through a resection slot of a resection guide coupled to the reference guide, the resection slot being indexed to the reference surface of the reference guide.

BRIEF DESCRIPTION OF THE DRAWINGS

The features, aspects, and advantages of the present invention will become better understood with regard to the following description, appended claims, and accompanying drawings in which:

FIG. 34A is a perspective view of an insert shim according to an embodiment of the present disclosure.

FIG. 34B is a perspective view of a tibial insert trial according to an embodiment of the present disclosure.

FIG. 34C is an assembly of the insert shim and tibial insert trial of FIGS. 34A and 34B, respectively.

DETAILED DESCRIPTION

When referring to specific directions in the following discussion of certain devices, it should be understood that such directions are described with regard to the device's orientation and position during exemplary application to the human body. Thus, as used herein, the term "proximal" means closer to the heart, and the term "distal" means further from the heart. The term "anterior" means toward the front part of the body or the face, the term "posterior" means toward the back of the body. The term "medial" means closer to or toward the midline of the body, and the term "lateral" means further from or away from the midline of the body. The term "inferior" means closer to or toward the feet, and the term "superior" means closer to or toward the crown of the head.

Also, as used herein, the term "flexion/extension ("F/E") gap" refers to the gap formed between a distal femur and proximal tibia during flexion and extension of the knee joint.

Further, as used herein, the terms "about," "generally," and "substantially" are intended to mean that slight deviations from absolute are included within the scope of the term so modified.

Figure 1:
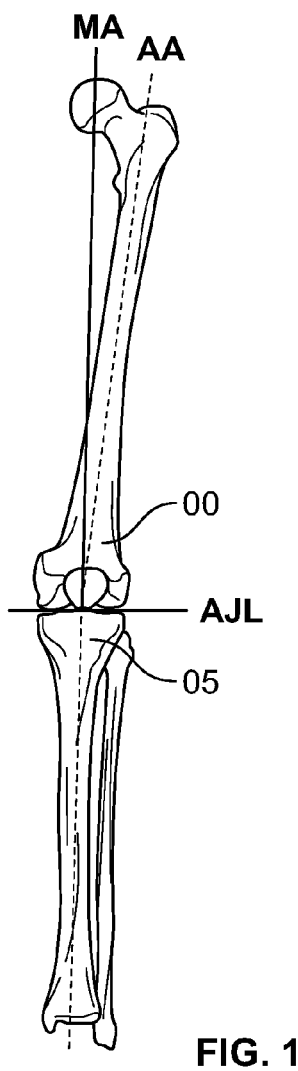
FIG. 1 is a schematic view of a femur and tibia and respective axes thereof.

FIG. 1 illustrates various leg bones, including a femur 00 and tibia 05. Femur 00 and tibia 05 interface to form an anatomic joint line (AJL) and a tibiofemoral joint. Femur 00 and tibia 05 each have a mechanical axis (MA), which extends from a center of a femoral head through the distal femur to the medial tibial spine, and from the medial tibial spine to the center of the ankle joint. Femur 00 and tibia 05 also have an anatomic axis (AA), which bisects the intramedullary ("IM") canal of femur 00 and tibia 05, respectively. The AA and MA of tibia 05 are typically aligned.

The axes of these bones and their relative positioning for a particular patient can be determined prior to a surgical procedure during a preoperative planning phase using radiographic imagery. During a TKA procedure, a surgeon typically locates the AA of femur 00 and/or tibia 05 using an IM rod or extramedullary device. Using the AA as a reference, the surgeon can then locate the MA.

Multiple techniques/philosophies exist for forming a proximal end of tibia 05 and distal end of femur 00 to receive corresponding prostheses. This can include MA and AA alignment in which resections of femur 00 and tibia 05 are performed at predetermined relative angles to the MA or AA, respectively. These techniques/philosophies are generally used to establish the final orientation of a prosthetic joint line, which may be different than that of the AJL.

Other techniques/philosophies include gap balancing and measured resection, which are generally concerned with preparation of a distal end of femur 00, such as the distal femoral condyles and posterior femoral condyles, so that the finally implanted prostheses align with each other and are balanced relative to soft tissue structures, such as the collateral ligaments.

Further techniques/philosophies include posterior referencing and anterior referencing, which are generally concerned with preparation of a distal end of femur 00, such as an anterior aspect thereof and the posterior femoral condyles, so that femur 00 can properly match an anteroposterior dimension of a prefabricated femoral component.

The following devices and sets of devices can perform a combination of some or all of the various techniques/ philosophies described above. In addition, they employ durable and simple to operate mechanisms that help consolidate the operation of multiple devices in order to provide operational flexibility with few devices.

The following devices are preferably made from biocompatible and sterilizable materials including, but not limited to, titanium, stainless steel, cobalt-chromium, tantalum, and niobium.

FIGS. 2A-2F illustrate a distal resection assembly 20, which includes a distal referencing guide 30 and a distal cutting guide 50. Distal referencing guide 30 includes a body 21 and an alignment member 40 rotatably connected to body 21.

Body 21 includes a reference plate or reference member 22 and a block portion 31 extending from reference plate 22. Reference plate 22 has a planar bone contact surface 26 (best shown in FIG. 2D), which is sufficiently large to extend from one femoral condyle to another femoral condyle. The perimeter of bone contact surface 26 and reference plate 22 is defined by a reference edge 23. Protrusions 27 (best shown in FIG. 2D) extend from reference edge 23 at lateral and medial sides of reference plate 22. Such protrusions 27 may be used to reference an epicondylar axis, for example. Additionally, reference edge 23 may be sloped in a lateral-medial direction (best shown in FIGS. 2B & 2C). Such slope may be about 3 degrees with respect to a coronal plane bisecting body 21. However, other angles are contemplated, such as 2 and 6 degrees. Such sloped edge 23 may be used to reference a posterior condylar axis of a femur, for example.

Block portion 31 extends from reference plate 22 and includes utility openings 33 extending into and through the entire block portion 31 in a direction substantially parallel to reference plate 22. Such utility openings 33 are sufficiently large to allow elongate members 59 of distal cutting guide 50 (see FIGS. 2E-F) to slide therein, but sufficiently small to create a friction lock that prevents distal cutting guide 50 from moving under the force of gravity absent external forces applied by an operator. In other words, utility openings 33 are sized to prevent elongate members 59 from sliding therein unless deliberately moved by an operator.

An angled pin hole 34 extends through body 21 and through bone contact surface 26. The angled pin hole 34 is sized to receive a bone pin and helps prevent rotation of distal referencing guide 30 when attached to an IM rod and also helps prevent distal referencing guide 30 from sliding along the bone pin away from the femur when attached thereto.

A toggle-hole or through-hole 24 also extends through body 21 and bone contact surface 26. Toggle-hole 24 includes a first portion and a second portion. The first portion is a circular hole extending through reference plate 22. The second portion is an oval hole defined by block portion 31 and by an ovular boss 32 that extends away from block portion 33. The largest dimension of the ovular geometry extends in a lateral-medial direction. The narrowest dimension of the ovular geometry extends in a direction transverse to the largest dimension. The narrowest dimension is substantially equal or slightly larger to the diameter of first portion. The largest dimension is larger than the diameter of the first portion. The communication of the circular first portion and ovular second portion forms a rim 25 at an interface thereof (best shown in FIG. 2C). This rim 25 allows for an elongate instrument, such as an IM rod, to be inserted through toggle-hole 24 and toggled or pivoted about rim 25 in a lateral-medial direction from one side of the ovular second portion to the other side. This allows such an elongate instrument to be oriented at a number of different angles with respect to bone contact surface 26.

Figure 2A:
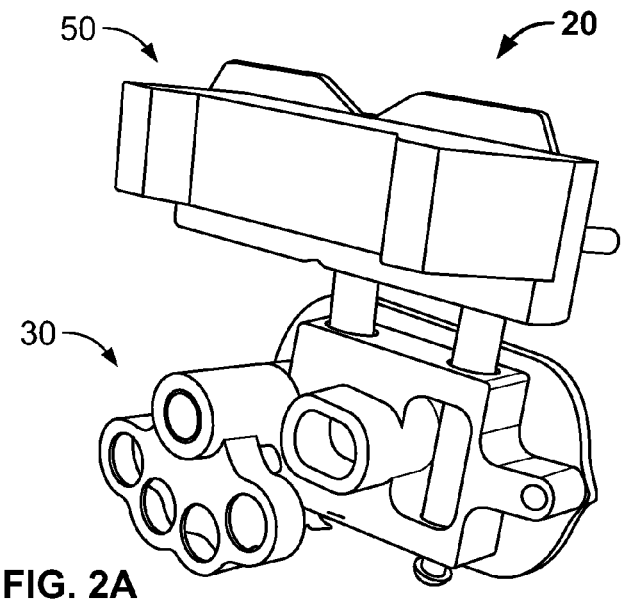
FIG. 2A is a front perspective view of a distal resection assembly including a distal referencing guide and a distal cutting guide according to an embodiment of the present disclosure.
Figure 2B:
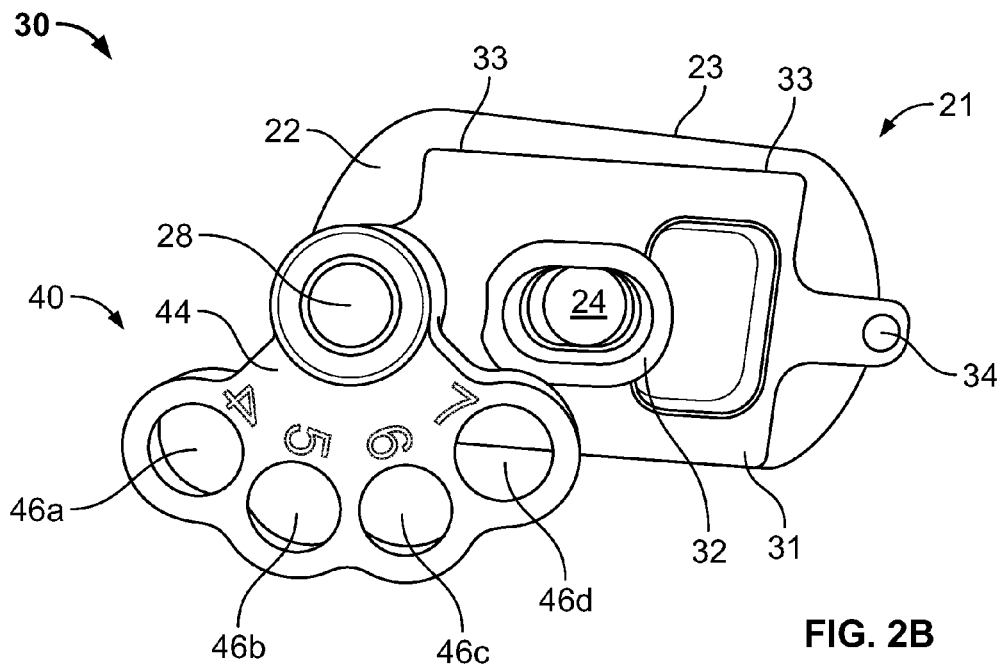
FIG. 2B is a front view of the distal referencing guide of FIG. 2A.
Figure 2C:
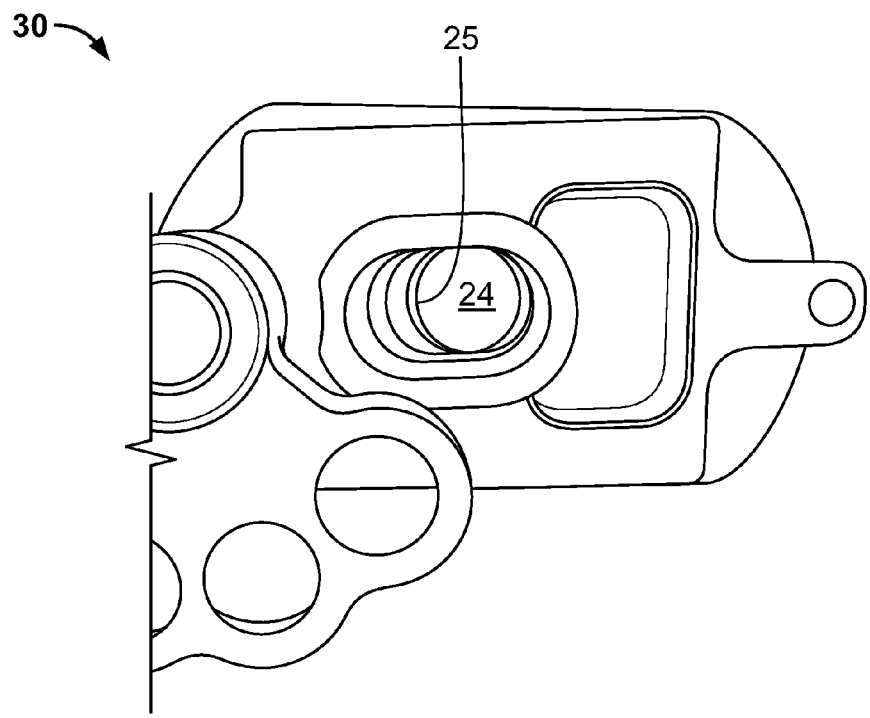
FIG. 2C is a magnified front view of the distal referencing guide of FIG. 2A.
Figure 2D:
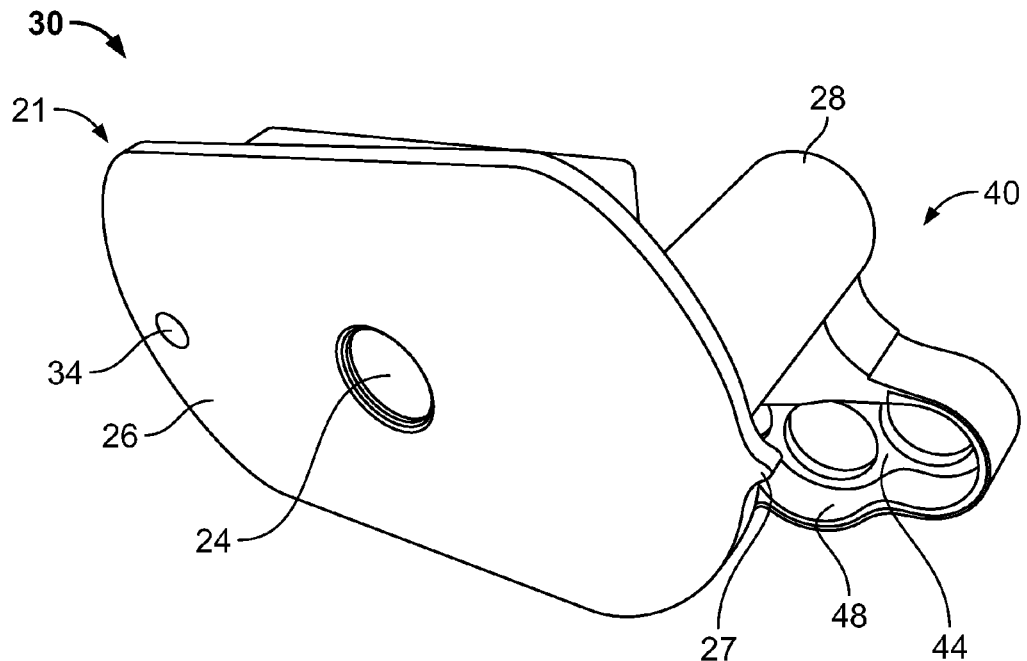
FIG. 2D is a rear perspective view of the distal referencing guide of FIG. 2A.
Figure 2E:
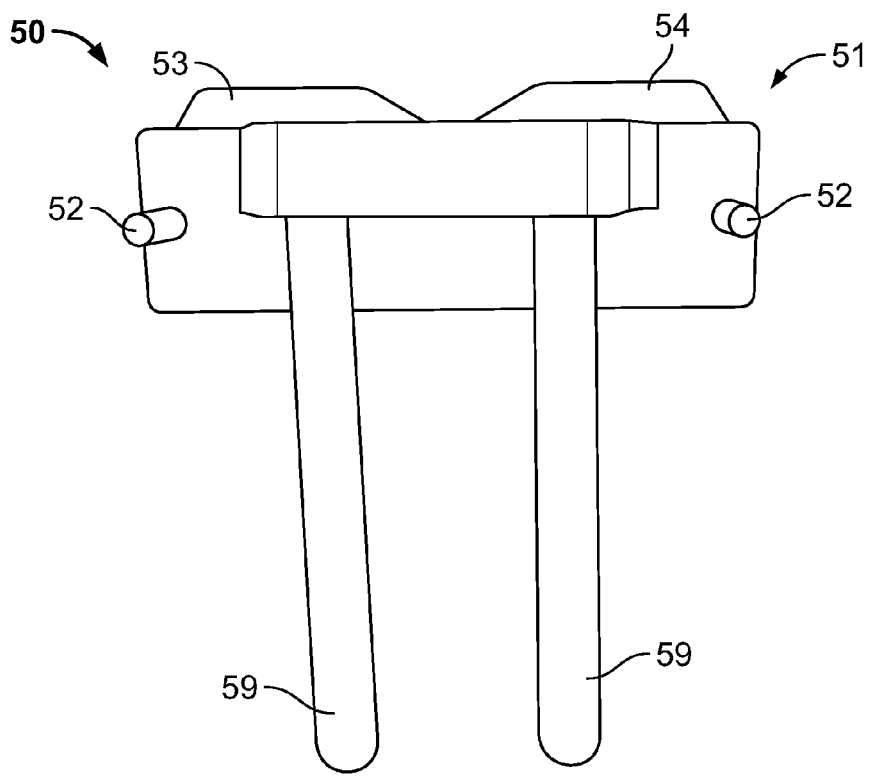
FIG. 2E is a front view of the distal cutting guide of FIG. 2A.
Figure 2F:
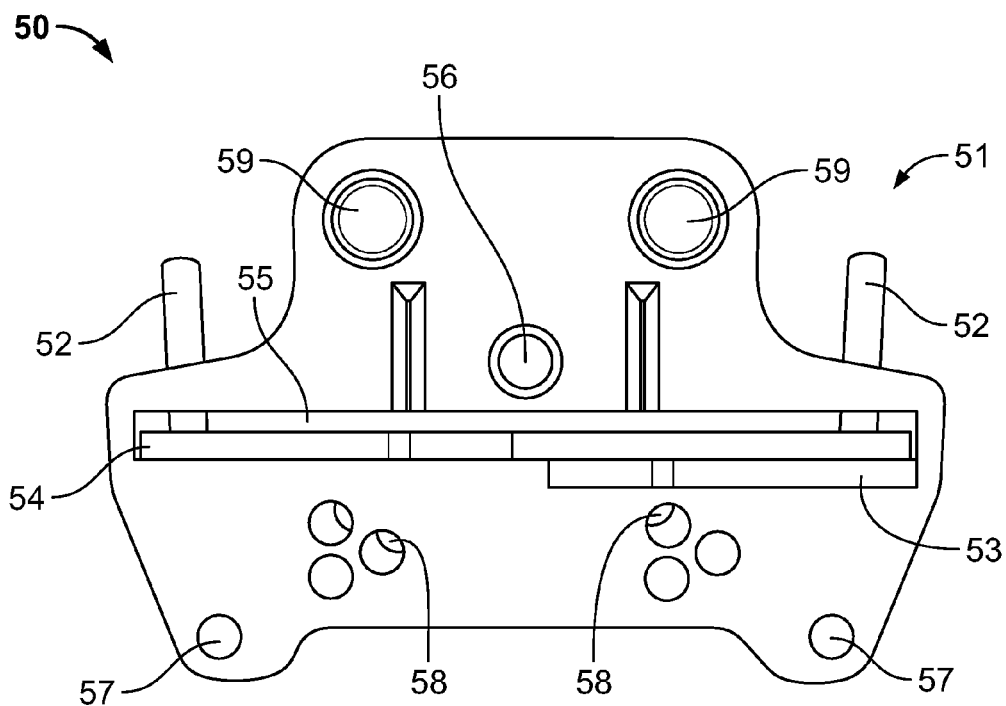
FIG. 2F is a top view of the distal cutting guide of FIG. 2A.

Alignment member 40 generally includes a plate portion 44 surrounded at its periphery by a frame 48 (best shown in FIG. 2D). However, in other embodiments, alignment member 40 may not have frame 48, and plate portion 44 may be thicker than the depicted embodiment. Alignment member 40 is generally fan shaped and includes a plurality of alignment holes 46a-d extending through plate portion 44. Alignment member 40 is rotatably connected to a hinge extension 28 extending from body 21. Hinge extension 28 defines a rotation axis about which alignment member 40 rotates.

As shown, alignment holes 46a-d includes four holes disposed adjacent one another. However, it is contemplated that alignment member 40 may include less than four holes or more than four holes. These holes 46a-d are positioned relative to one other and to the rotation axis so that when alignment member 40 is rotated relative to body 21, each alignment hole 46a-d can be positioned in alignment with toggle-hole 24 of body 21. In addition, each alignment hole 46a-d, when positioned in alignment with toggle-hole 24, forms an axis with toggle-hole 24 that has an angle relative to bone contact surface 26, which differs from an axis formed by the other alignment holes. In other words, positioning the first alignment hole 46a in alignment with toggle-hole 24 forms an axis having an angle different than an axis formed by the second, third, or fourth alignment holes 46b-d.

Each of these angles corresponds to a different varus-valgus angle. For example, first hole 46a may be associated with a varus-valgus angle of 4 degrees, second hole 46b may be associated with a varus-valgus angle of 5 degrees, third hole 46c may be associated with a varus-valgus angle of 6 degrees, and fourth hole 46d may be associated with a varus-valgus angle of 7 degrees. However, other angles are contemplated, such as 0 to 3 degrees, 1 to 4 degrees, 2 to 5 degrees, 3 to 6 degrees, and 5 to 8 degrees, for example. Thus, when first alignment hole 46a is aligned with toggle-hole 24, an axis formed thereby is oriented 7 degrees from a normal axis perpendicular to bone contact surface 26 or 83 degrees relative to bone contact surface 26. This allows for bone contact surface 26 to be positioned at various angles in relation to an IM rod extending from femur 00 and inserted into toggle-hole 24 and one of alignment holes 46a-d. In short, the combination of alignment member 40 and toggle-hole 24 can be used to establish varus-valgus alignment of referencing guide 30 relative to femur 00 during a TKA procedure.

The various angles formed by the alignment of toggle-hole 24 and alignment holes can be achieved by the structure of the depicted embodiment. As previously mentioned, rim 25 formed by the communication of the first and second portions of toggle-hole 24 allow for an IM rod to be positioned at various angles therein. In addition, alignment holes 46a-d of the alignment guide 30 are positioned adjacent one another along a circular arc. Such arc may have a center point, which itself is offset from the rotation axis of alignment member 40. Thus, when alignment member 40 is rotated and each alignment hole 46a-d is passed over toggle-hole 24, each alignment hole 46a-d is positioned over toggle-hole 24 in a different lateral-medial location than the other alignment holes. For example, when fourth alignment hole 46d is positioned over toggle-hole 24, fourth alignment hole 46d is positioned closer to hinge extension 28 in a lateral-medial direction than when first alignment hole 46a is positioned over toggle-hole 24. Therefore, rim 25 allows for an IM rod to be positioned at various angles therein, and alignment holes 46a-d establish a predetermined angle for the IM rod.

It is noted that distal referencing guide 30 is universal to a right and left femur of a patient by rotating the guide 180 degrees. Therefore, distal referencing guide 30, which can establish multiple varus-valgus angles in both legs, consolidates multiple referencing guides that would typically be needed to perform the same functions, thereby reducing the number of devices needed in the operating theater.

The distal cutting guide 50 (best shown in FIGS. 2E & 2F) includes a body 51 and elongate members 59 extending from body 51. The elongate members 59 are generally cylindrical and are sized to fit within utility openings 33 of distal referencing guide 30. In addition, elongate members 59 have a length sufficient to allow body 51 to be positioned at various heights above distal referencing guide 30.

Body 51 includes a utility opening 56, a plurality of adjustment pinholes 58, and a plurality of angled pin holes 57 each extending through body 51. Utility opening 56 can receive various instruments, such as an aiming device or stylus, for example. Adjustment pinholes 58 are sized to receive a bone pin and are positioned relative to each other in specific increments, such as 1 mm increments, to allow body 51 to be incrementally positioned proximally or distally relative to a femur without altering the angular orientation of body 51 thereto. Angled pinholes 57 are sized to receive bone pins and are angled to help prevent movement of the body away from femur 00 during resection thereof.

Body 51 also includes a slot 55 extending therethrough. Slot 55 or floating slot is defined by resection guide surfaces disposed opposite each other. Also, resection guide surfaces are generally planar and parallel to each other. A pair of rails 52 extend through the body and slot at lateral and medial positions thereof. Although, in some embodiments a single rail may be provided, such as through the center of slot 55. A shim 54 is positioned within slot 55 between the resection guide surfaces and attached to rails 52 so that shim 54 is slidable from one resection guide surface to the other. Shim 54 has a substantially uniform thickness and is sized relative to slot 55 to allow a bone saw blade to be inserted into slot 55 on either side of shim 54. Thus, when the bone saw blade resects bone through slot 55 at a first side of shim 54, the saw blade resects a first thickness of bone, and when the saw blade resects bone through slot 55 at a second side of shim 54, the saw blade resects a second thickness of bone.

In one embodiment of body 51, the distance between the resection guide surfaces, and, therefore, a thickness of slot 55, is about 4 mm, and the thickness of shim 54 is about 2 mm. In such an embodiment, resecting through slot 55 at a first side of shim 54 resects about 8 mm of bone, and resecting through slot 55 at a second side of shim 54 resects about 10 mm of bone. Other dimensions of slot 55 and shim 54 are contemplated and may be selected to correspond with a distal thickness of various femoral prostheses. In other words, the dimensions of slot 55 and shim 54 may be selected so that resecting along one side of shim 54 removes an amount of bone substantially equal to a distal thickness of a first femoral prosthesis, and resecting along a second side of shim 54 removes an amount of bone substantially equal to a distal thickness of a second femoral prosthesis. The first and second femoral prostheses may be different sized prostheses provided in a kit. While the depicted embodiment has only one shim 54, other embodiments having two or three shims stacked adjacent one another are also contemplated. This floating slot mechanism helps consolidate multiple instruments each used to resect a different amount of bone, thereby reducing the number of instruments in an operating theater.

Figure 3:
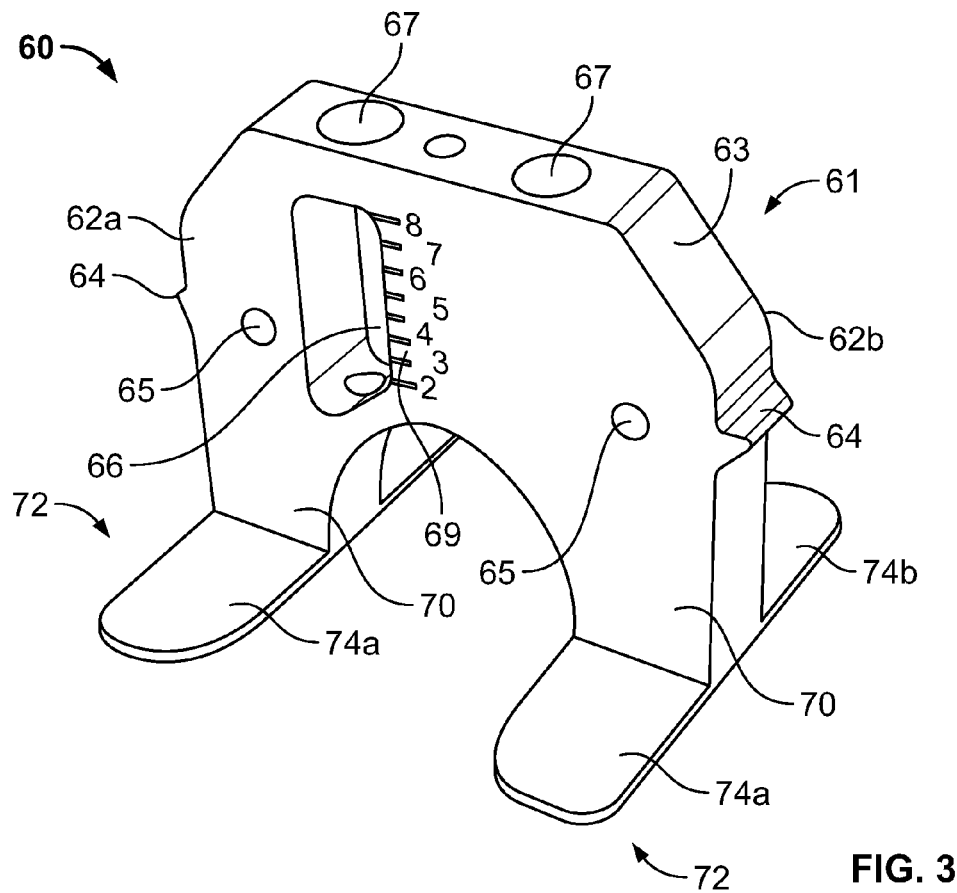
FIG. 3 is a front perspective view of an A/P referencing/sizing guide according to an embodiment of the present disclosure.

FIG. 3 is an anterior/posterior ("A/P") referencing and/or sizing guide 60 which is configured for a posterior referencing technique/philosophy. A/P guide 60 can be used to reference bone surfaces to establish internal/external ("I/E") rotation of a femoral component and size for a femoral component. A/P guide 60 includes a body 61, which has first and second bone contact surfaces 62a and 62b disposed opposite each other and separated by a sidewall 63. Bone contact surfaces 62a and 62b are generally planar for contacting a distal resected surface of a femur.

A window 66 extends through body 61 from first bone contact surface 62a to second bone contact surface 62b. Additionally, a pair of utility openings 67 extends into sidewall 63 in a direction substantially parallel to the bone contact surfaces 62a and 62b. One of utility openings 67 intersects window 66. Indicia 69 are formed on first and second bone contact surfaces 62a and 62b adjacent window 66, which can indicate a prosthesis size. As such, a reference plate (discussed further below) or some other reference device, can be attached to body 61 via utility openings 67 and indicia 69 can be correlated with markings on a portion of the reference device exposed within window 66 to indicate a femoral component size.

Body 61 also includes a pair of legs 70 extending therefrom. A foot 72, for referencing a posterior condyle, is attached to each leg 70 and extends transversely to legs 70 in opposing directions therefrom. Each foot 72 includes a pair of reference surfaces 74a and 74b. Reference surfaces 74a and 74b are substantially planar and oriented substantially perpendicular to a respective bone contact surface 62a and 62b.

Guide pin holes 65 extend through body 61 from first bone contact surface 62a to second bone contact surface 62b. Such guide holes 65 are generally sized to receive bone pins or reference pins therein. Such reference pins may be used by other devices, some of which are described below, for orientation relative to femur 00. Guide pin holes 65 and 65 are positioned a predetermined distance relative to reference surface 74a and 74b of the feet 72 in accordance with a posterior referencing technique/philosophy. In addition, guide pin holes 65 are positioned relative to reference surfaces 62a and 62b such that a plane bisecting pinholes 65 is oriented a predetermined angle relative to a plane defined by reference surfaces 74a and 74b of the feet 72. Such angle may be 3 degrees as shown in the depicted embodiment. Other embodiments may have other angles, such as 1, 2, 4, 5, and 6 degrees, for example. Additionally, indicia may be provided on bone contact surfaces 62a and 62b to indicate this relative angle and also to indicate which leg, right or left, is associated with each bone contact surface 62a, 62b.

Protrusions 64 extend from sidewall 63 at lateral and medial locations thereof. A plane bisecting such protrusions 64 may be parallel to a plane bisecting guide holes 65. Such protrusions 64 may be used to reference bony landmarks, such as an epicondylar axis, for example.

Figure 4A:
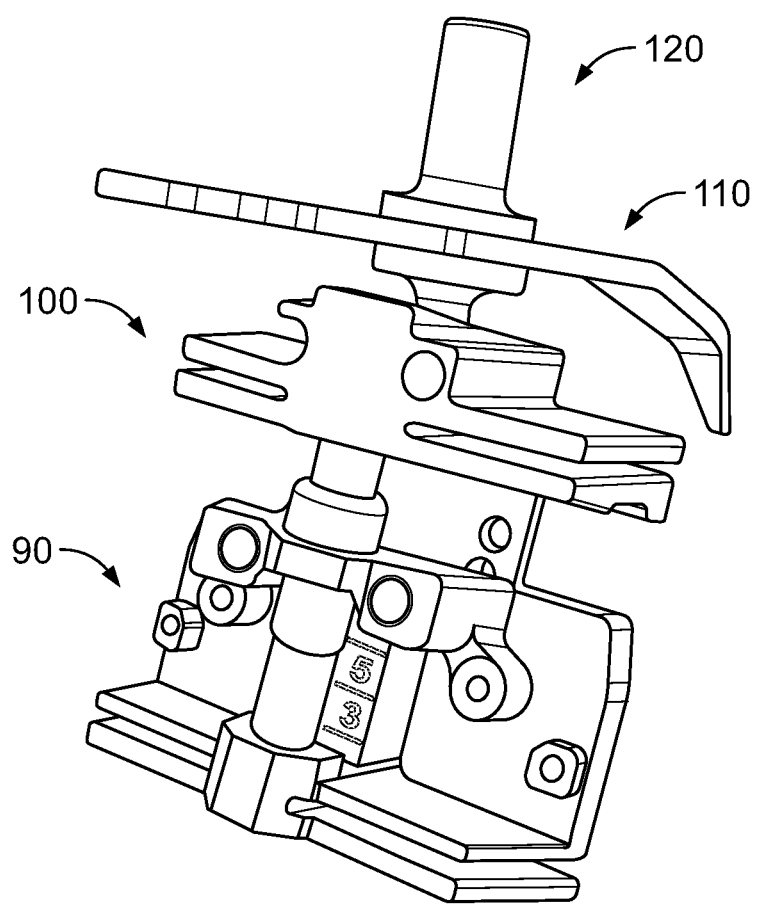
FIG. 4A is a front perspective view of an A/P cutting/sizing guide including a lower and upper body according to an embodiment of the present disclosure.
Figure 4B:
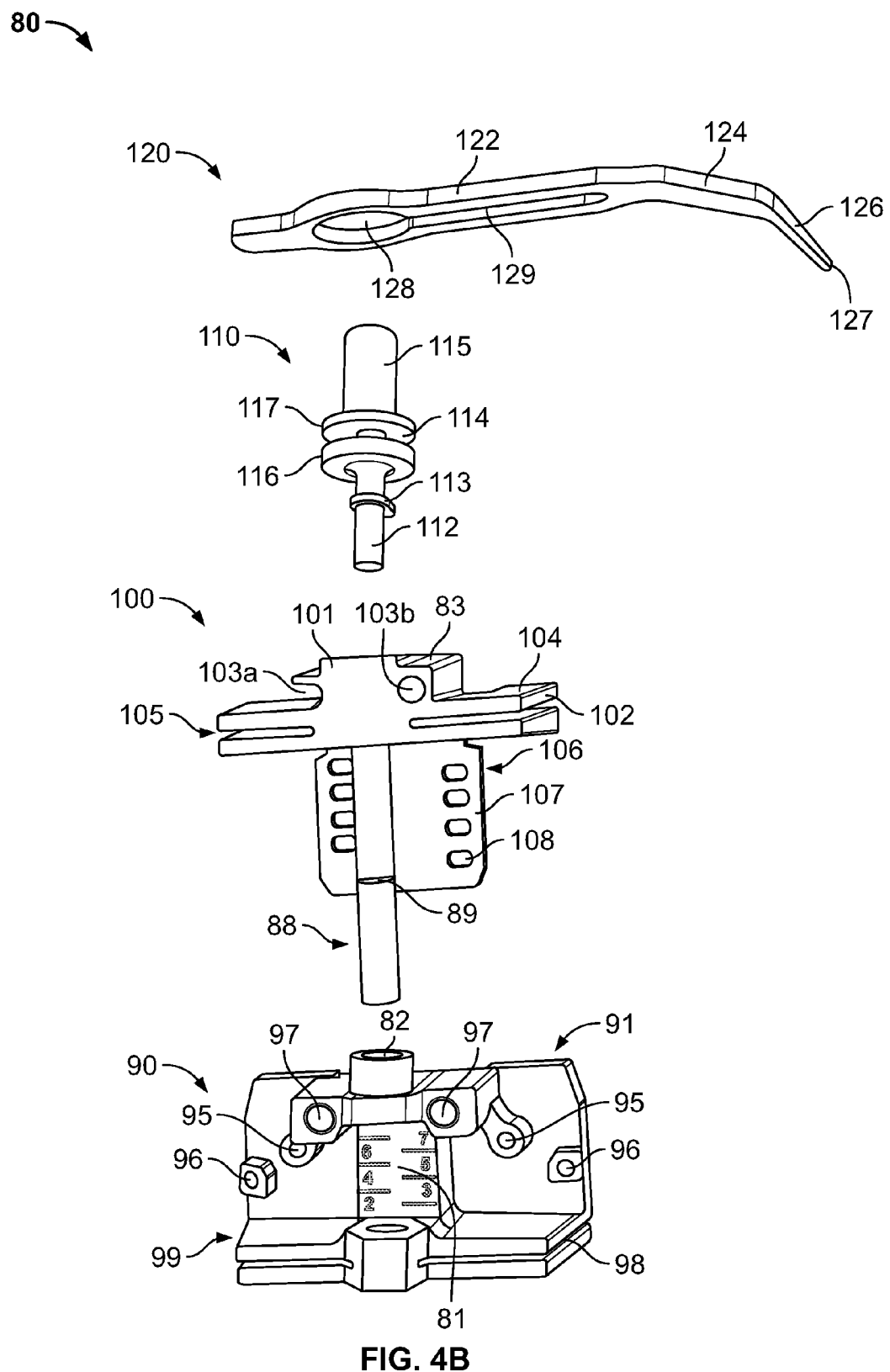
FIG. 4B is an exploded view of the A/P cutting/sizing guide of FIG. 4A.
Figure 4C:
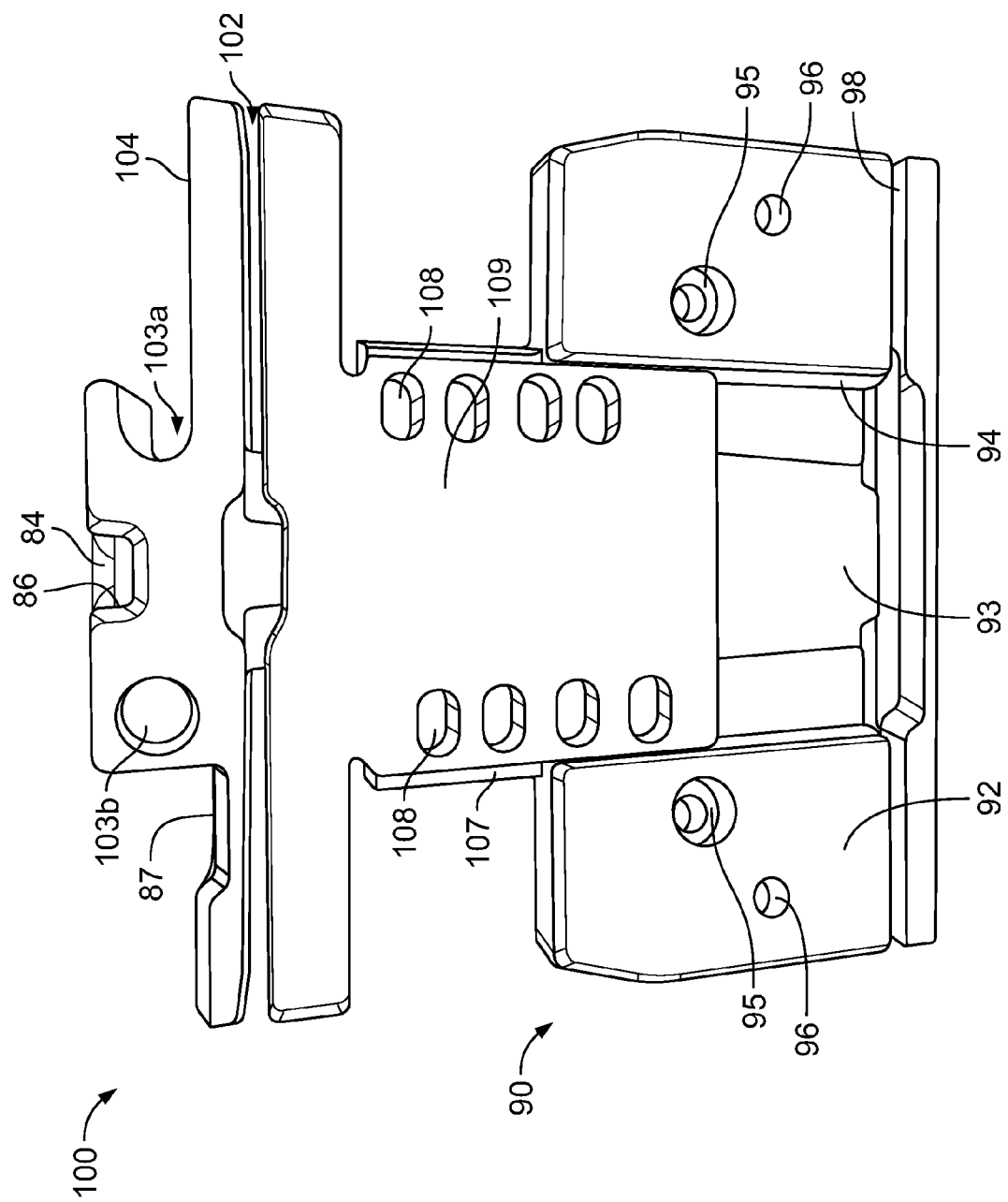
FIG. 4C is a rear view of the lower and upper bodies of FIG. 4A.

FIGS. 4A-4C depict an A/P cutting and/or sizing guide 80. A/P guide 80 can be used to perform posterior and anterior femoral resections and can also be used to size a femoral component. A/P guide 80 generally includes a first body 100, second body 90, connection bolt 120, and resection stylus 110.

First body 100 or upper body includes a resection member 105, a mating member 89, and an elongate member 88. Resection member 105 includes opposing guide surfaces defining an anterior resection slot 102 extending therethrough. Slot 102 is configured to receive and guide a bone saw blade for performing an anterior resection of femur 00.

First and second utility openings 103a and 103b extend through resection member 105 adjacent to slot 102 in the same general direction as slot 102. As shown, first utility opening 103a may be open on a side thereof along its length. However, in some embodiments, both openings 103a and 103b may be enclosed along their respective lengths. Utility openings 103a and 103b are configured to receive elongate members of a contact plate, which is described in further detail below.

A connection bolt opening 84 (best shown in FIG. 4C) extends into resection member 105 in a direction transverse to utility openings 103a and 103b and slot 102. Bolt opening 84 includes a groove 86 formed about an axis thereof for receipt of a protrusion 113 of connection bolt 110 (described further below).

An upper surface 104 of resection member 105 adjacent slot 102 includes an indented region 87 (best shown in FIG. 4C), which may be sloped to correspond with a skim cut angle and is dimensioned to receive an extension of a contact plate (described further below).

Resection member 105 also includes a notched surface 83 adjacent second utility opening 103b. Notched surface 83 includes a plurality of notches each being configured to receive a forked portion of a contact plate (described further below).

Mating member 106 extends from resection member 105 and, as depicted, is in the form of a quadrilateral plate. Mating member 106 includes a bone contact surface 109 (best shown in FIG. 4C). Bone contact surface 109 is substantially planar and may align with a bone facing side of resection member 105 to form a continuous bone contact surface. A plurality of retaining holes 108 extends through mating member 89 and through bone contact surface 109. Retaining holes 108 are situated in two rows at lateral and medial sides of mating member 106. Each row downwardly extends from resection member 105. Each retaining hole 108 is spaced from an adjacent retaining hole 108 a distance based on different sizes of a femoral component. Mating member 106 also includes a tongue 107 extending along a peripheral edge thereof for receipt in a groove 94 of second body 90, as described further below.

Elongate member 88 also extends from resection member 105 in generally the same direction as mating member 106. Mating member 106 and elongate member 88 are offset from each other so as to form a space therebetween. Elongate member 88 is generally cylindrical and is sized to be slidingly received in an opening 82 in second body 90. An indicator line 89 is formed along the length of elongate member 88 to facilitate size assessment.

Second body 90 or lower body generally includes a bone contact portion 91 and a resection portion 99. Bone contact portion 91 is a plate-like structure that includes a bone contact surface 92. Bone contact surface 92 is substantially planar for contacting a distal resected surface of femur 00. A recess 93 (best shown in FIG. 4C) extends through an upper surface of bone contact portion 91 toward resection portion 99. Recess 93, as shown, also extends through bone contact surface 92 a distance that allows bone contact surface 109 of mating member 106 to align with bone contact surface 92 when mating member 106 is disposed within recess 93. However, in some embodiments, recess 93 may only extend through an upper surface of bone contact portion 91 such that recess 93 is enclosed on all sides. A groove 94 extends along a perimeter of recess 93 for receipt of the tongue 107.

Second body 90 also includes retaining holes 97, guide holes 95, and angled pinholes 96 extending therethrough. Retaining holes 97 intersect recess 93 and align with a pair of retaining holes 108 of first body 100 when mating member 106 is disposed within recess 93. Guide holes 95 extend through bone contact surface 92 and are positioned relative to each other to match the spacing of guide holes 65 of A/P guide 60, which allows A/P guide 80 to be properly oriented and positioned relative to femur 00. Angled pinholes 96 are configured to receive pins to prohibit relative movement of A/P guide 80 during resection.

Resection portion 99 is disposed at an end of bone contacting portion 91 and includes opposing resection guide surfaces defining a posterior resection guide slot 98. Slot 98 is located a predetermined distance and orientation relative to guide holes 95. In a preferred embodiment, guide holes 95 are parallel to slot 98 and the predetermine distance is based on a posterior thickness of a prosthesis and the distance between reference surfaces 74a-b and guide holes 65 of A/P guide 60.

An opening 82 extends through bone contact portion 91 and resection portion 98 and is offset from recess 93. Opening 82 is configured to receive elongate member 88 of first body 100. A portion of second body 90 is cut out so that when elongate member 88 is inserted through opening 82, a portion of elongate member 88 is visible (best shown in FIG. 4A). Second body 90 includes indicia 81 in this cut out region which can be used in conjunction with markings 89 on elongate member 88 to size a femoral prosthesis.

Attachment bolt 110 includes lower and upper shaft portions 112, 115. A groove 114 is formed between lower and upper shaft portions 112, 115. As shown, groove 114 partially defines first and second disc-like portions 116, 117 that each have a cross-sectional dimension larger than a cross-sectional dimension of lower and upper shaft portions 112, 115. In addition, upper shaft portion 115 has a larger cross-sectional dimension than lower shaft portion 112. However, in some embodiments, connection bolt 110 may be a continuous shaft with a groove formed along its length. Upper shaft portion 115 is generally configured for tactile manipulation, particularly between a thumb and index finger. Lower shaft portion 112 is sized to fit within connection bolt opening 86 of first body 100 and includes protrusion 113 extending radially outwardly for receipt within groove 86 of bolt opening 84.

Resection stylus 120 includes first, second, and third elongate portions 122, 124, 126. Second elongate portion 124 extends from first elongate portion 122 at a first downwardly depending angle. Third elongate portion 126 extends from second elongate portion 124 at second downwardly depending angle that may be steeper than the first downwardly depending angle. A contact tip 127 is disposed at a terminal end of third elongate portion 126 and has a width greater than a thickness thereof for contacting an anterior cortex of a femur. A circular opening 128 and elongate slot 129 extends through first elongate portion 122 and are in fluid communication with each other. Circular opening 128 is larger than the largest radial dimension of connection bolt 110. Elongate slot 129 is narrower than the largest radial dimension of connection bolt 110 such that rail portions defining the slot are receivable by groove 114 of connection bolt 110.

When A/P guide 80 is assembled (best shown in FIG. 4A), first and second bodies 100, 90 are slidingly connected, connection bolt 110 is rotatably connected to first body 100, and resection stylus 120 is slidingly connected to connection bolt 110. More particularly, mating member 106 is disposed within recess 93 and elongate member 88 is disposed within opening 82. Resection member 105 can be moved toward or away from second body 90 by sliding mating member 105 within recess 93 and elongate member 88 within the opening 82.

Lower shaft portion 112 of connection bolt 110 is disposed within connection bolt opening 84 of first body 100 and protrusion 113 is disposed within groove 86 to help retain connection bolt 110 within opening 84. Stylus 120 is positioned within groove 114 of anchoring bolt 110 and can be slid relative to anchoring bolt 110 to help position tip 127 relative to femur 00. When coupled to anchoring bolt 110, tip 127 aligns with a plane defined by anterior resection slot 102. Anterior resection slot 102 aligns with posterior resection slot 98, and may have differing slopes (i.e., planes defined by said slots 98 and 102 may not be parallel, although they can be) based on the configuration of corresponding surfaces of a femoral prosthesis.

Figure 5A:
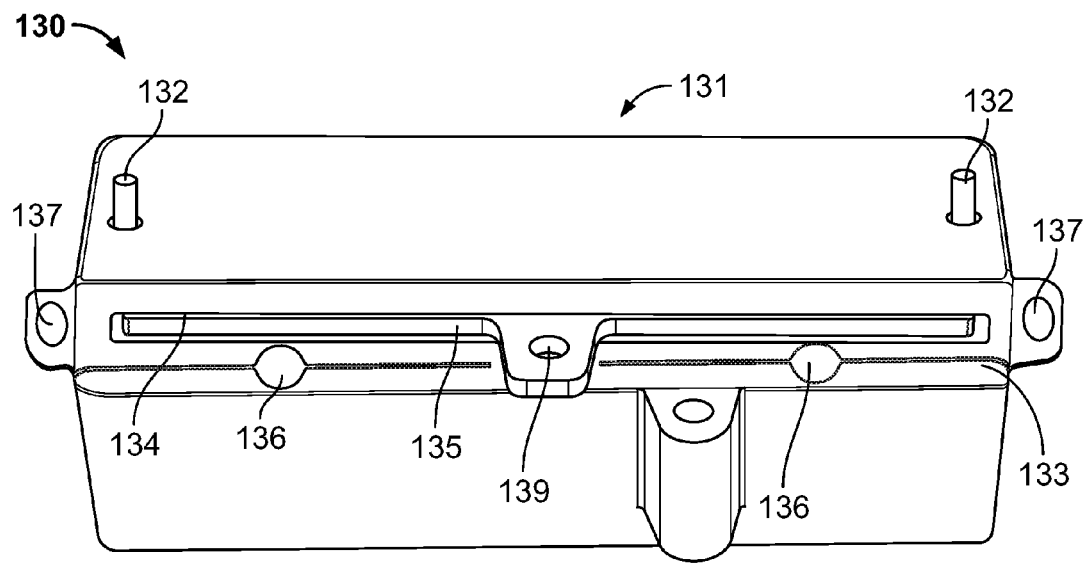
FIG. 5A is a front view of a chamfer resection block according to an embodiment of the present disclosure.
Figure 5B:
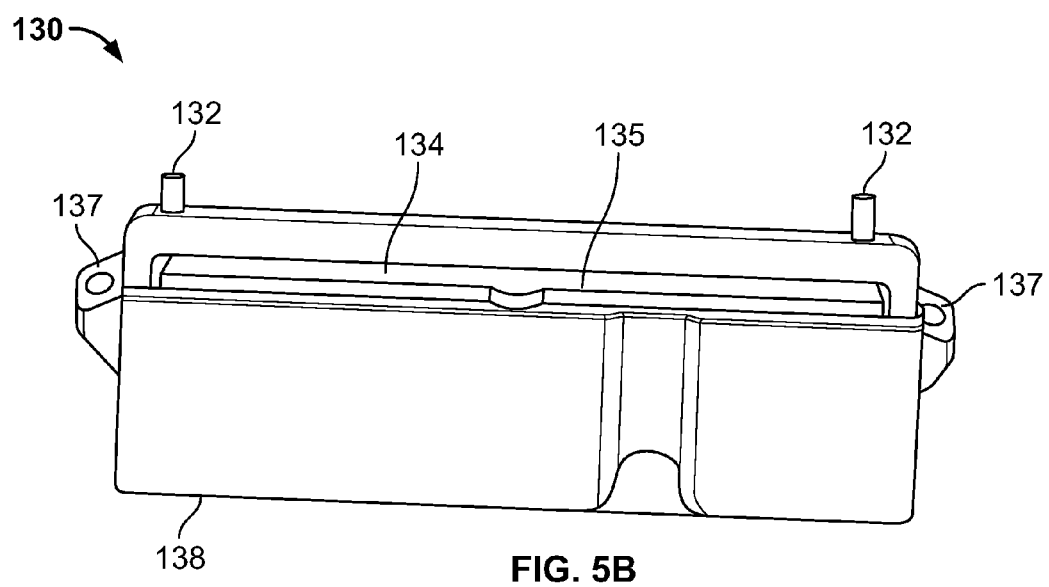
FIG. 5B is a bottom perspective view of the chamfer resection block of FIG. 5A.

FIGS. 5A and 5B depict a chamfer resection block 130. Chamfer resection block 130 can be used to perform anterior and posterior femoral chamfer resections. Chamfer resection block 130 generally includes a triangular body 131 that includes a bone contact surface 138. Bone contact surface 138 is substantially planar for contacting a distal resected surface of femur 00. An adjustable or floating slot 134 is defined by a pair of opposing resection guide surfaces and extends through body 131 and bone contact surface 138 at a first orientation for performing an anterior chamfer resection. A fixed or nonadjustable slot 133 extends through body 131 and bone contact surface 138 at a second orientation for guiding a posterior chamfer resection. The first and second orientations are based on relative angles of corresponding surfaces of a femoral prosthesis.

A pair of rails 132 extends through adjustable slot 134 at lateral and medial locations. A shim 135 is positioned within slot 134 between the resection guide surfaces and is attached to rails 132 so that shim 135 is slidable from one resection guide surface to the other. Shim 135 has a substantially uniform thickness and is sized to allow a bone saw blade to be inserted into slot 134 on either side of the shim 135, which helps vary the depth of resection to accommodate various sized femoral prostheses. Thus, when a bone saw blade resects bone through slot 134 at a first side of shim 135, the saw blade resects a first thickness of bone, which may correspond to a first size prosthesis, and when the saw blade resects bone through slot 134 at a second side of shim 135, the saw blade resects a second thickness of bone, which may correspond to a second size prosthesis. In the embodiment depicted, a first side or anterior side of shim 135 corresponds with a size 6 prosthesis, and a second side or posterior side of shim 135, which results in more bone being resected, corresponds to a smaller size 5 prosthesis. Operator facing indicia indicates which side of shim 135 corresponds to which prosthesis. While the depicted embodiment has only one shim, other embodiments having two or three shims stacked adjacent one another are contemplated. The floating slot mechanism described above helps consolidate multiple instruments each used to resect a different amount of bone, thereby reducing the number of instruments in an operating theater.

Chamfer block 130 also includes guide openings 136 disposed between adjustable and nonadjustable slots 134, 133. Guide openings 136 are positioned relative to each other similar to guide openings 65 of the A/P guide 60 so that chamfer block 130 can be properly I/E oriented. Chamfer block 130 further includes angled pinholes 137 at lateral and medial edges thereof to help stabilize and retain chamfer block 130 against femur 00 during resection.

Although the depicted embodiment includes a nonadjustable slot 133 for performing a posterior chamfer resection, such nonadjustable slot 133 can also be adjustably configured similar to slot 134. In addition, nonadjustable slot 133 may be partitioned into two segments in order to create space for a tab 139 of shim 135 with indicia located thereon. Such tab 139, as shown, may extend beyond body 131 and may help guide a saw blade and provide a visual indication to an operator of which side of shim 135 the blade is located.

Many current instrument sets include 4-in-1 cutting blocks, which include four cutting slots for performing posterior and anterior resections as well as posterior and anterior chamfer resections. However, these 4-in-1 cutting blocks are often non-adjustable. As such, instruments sets typically require multiple 4-in-1 cutting blocks to correspond with the various prosthesis sizes. A/P guide 80 and chamfer block 130 decouples the chamfer resections from the anterior and posterior resections, which ultimately results in less total instruments in a set. This is achieved by the adjustability of A/P guide 80 and chamfer block 130, which can each guide resections corresponding to multiple femoral component sizes. Thus, reducing the total number of instruments needed for a TKA procedure.

FIGS. 2A-5B depict a first set of devices which, as a set, can perform MA or AA alignment, measured resection, and posterior referencing techniques/philosophies. A method of using these devices to perform an MA alignment, measured resection and posterior referencing techniques/philosophies is illustrated in FIGS. 6-10 and is now described.

In a TKA procedure, after the knee joint is exposed, an IM rod 10 is placed within the IM canal of femur 00 such that IM rod 10 at least partially extends from the distal end of the femur 00. IM rod 10 can be a portion of an IM reamer, which reams through the distal end of femur 00 into the IM canal. At this point, the IM rod 10 is substantially aligned with an AA axis of femur 10.

The orientation of the MA axis is determined relative to the AA axis, which is typically oriented 3 to 7 degrees from the AA axis. Distal referencing guide 30 is obtained and a varus-valgus angle is determined, which may correspond with the angular difference between the AA and MA axes. Alignment member 40 is rotated until the desired alignment hole 46a-d corresponding with the determined varus-valgus angle is positioned over and aligned with toggle-hole 24. Thus, the orientation of distal resection of femur 00 relative to the MA, in a MA alignment philosophy/technique, helps determine, which alignment hole 46a-d is selected. For example, where it is desired to perform a distal resection perpendicular to the MA and the MA is oriented 4 degrees relative to the AA, alignment hole 46a corresponding to 4 degrees varus-valgus is selected.

Figure 6:
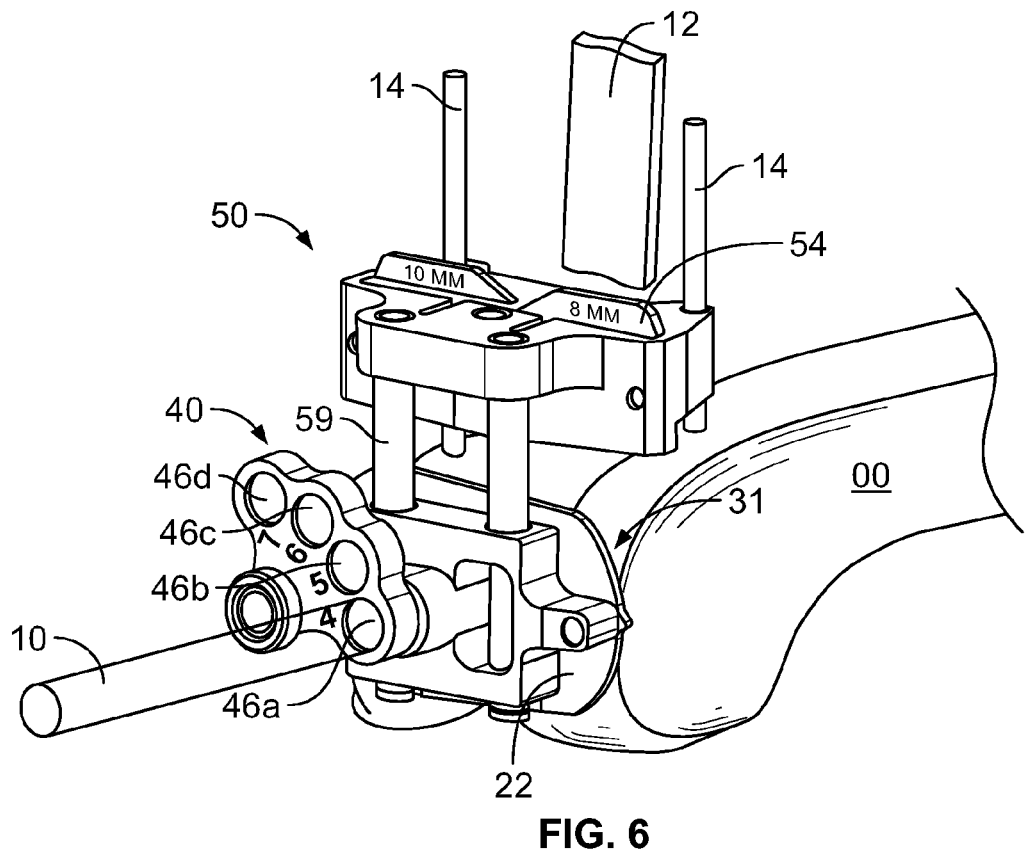
FIG. 6 illustrates a method of using distal resection assembly of FIG. 2A.
Figure 7:
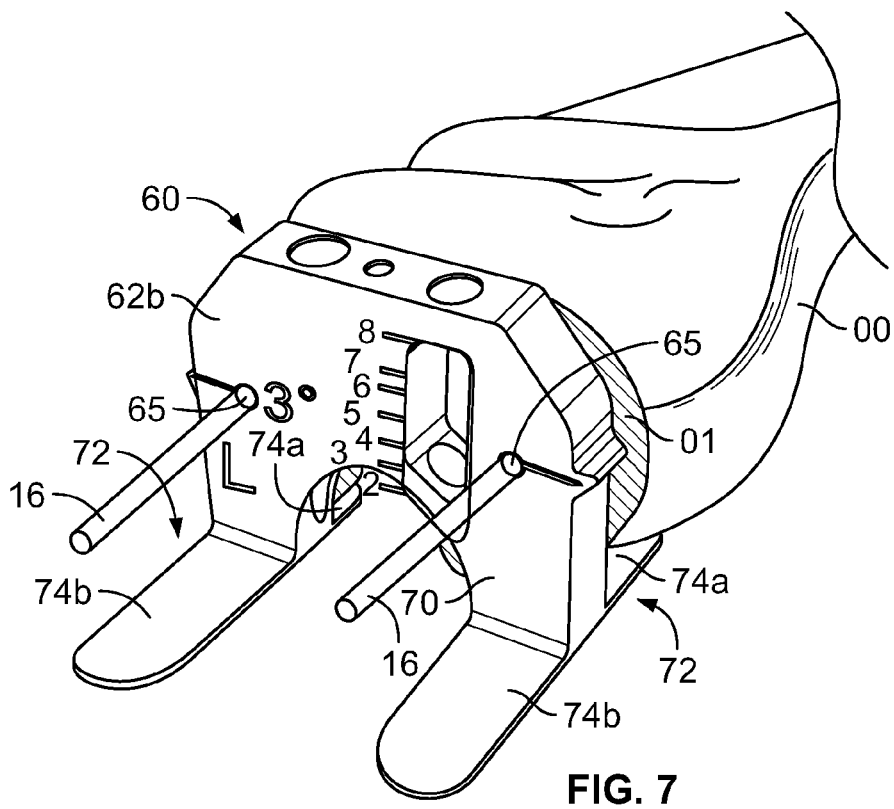
FIG. 7 illustrates a method of using A/P referencing/sizing guide of FIG. 3.
Figure 8:
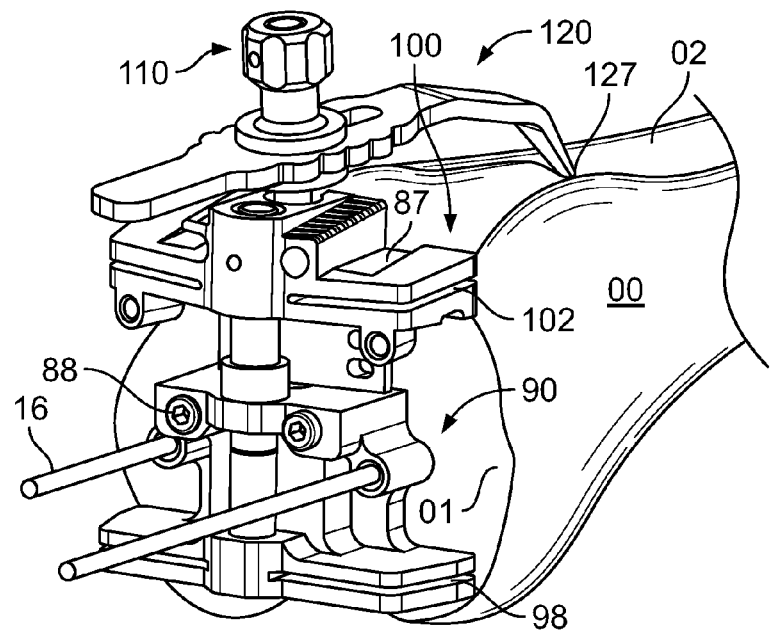
FIGS. 8 and 9 illustrate a method of using A/P cutting/sizing guide of FIG. 4A.

Once the desired alignment hole 46a-d is aligned with toggle-hole 24, referencing guide 30 is slid onto the IM rod 10 by passing IM rod 10 through toggle opening 24 and selected alignment hole 46a-d (best shown in FIG. 6). This aligns IM rod axis with an axis formed by toggle-hole 24 and alignment hole 46a-d. Referencing guide 40 is slid along IM rod 10 until bone contact surface 26 abuts the distal femur. Due to the angle of IM rod 10 relative to bone contact surface 26, which is imposed by the alignment of toggle-hole 24 and alignment opening 46a-d, bone contact surface 26 may only contact one distal condyle. At this point bone contact surface 26 aligns with the MA axis as desired and a bone pin may be inserted into angled pinhole 34 to firmly fix referencing guide 30 to femur 00.

Distal cutting guide 50 is connected to referencing guide 30, which can take place either before or after connecting referencing guide 30 to IM rod 10. Connection of cutting guide 50 is performed by inserting elongate members 59 into corresponding utility openings 33 in referencing guide 30. The height of cutting guide 50 relative to referencing guide 30 can be adjusted by sliding elongate members 59 within utility openings 33 until distal cutting guide 50 contacts femur 00 (best shown in FIG. 6). At this point, adjustable/floating slot 55 is parallel to bone contact surface 26 of referencing guide 20 and, therefore, positioned in the desired orientation relative to the MA axis. Bone pins are inserted into angled pinholes 57 of cutting guide 50 to firmly fix cutting guide 50 to femur 00.

Thereafter, IM rod 10 is removed from the IM canal and, optionally, referencing guide 30 is removed from cutting guide 50. A saw blade 12 is inserted through adjustable slot 55 at a selected side of shim 54 and cuts through femur 00 to remove a desired amount of bone (best shown in FIG. 6). Cutting through the first side, or distal side, of shim 54 removes less bone than a second side, or proximal side, of the shim. In a measured resection technique, the amount of bone removed generally corresponds to the thickness of the femoral prosthesis at a distal end thereof. For example, where the prosthesis is 8 mm thick, saw blade 12 is inserted through slot 55 at the first side of shim 54 corresponding to 8 mm of bone. Where the prosthesis is 10 mm thick, saw blade 12 is inserted through slot 55 at the second side of shim 54 corresponding to 10 mm of bone. Once the distal resection is performed, further bone can be removed using adjustment pinholes 58 or by resecting on the second side of shim 54 if the initial resection was performed on the first side of shim 54.

A/P referencing guide 60 can then be used to establish I/E rotation of the femoral prosthesis and ultimately a location of a posterior resection through referencing posterior condyles of femur 00 in accordance with a posterior referencing technique/philosophy. As shown in example of FIG. 7, A/P guide 60 is obtained and the appropriate bone contact surface 62a or 62b for the particular leg, right or left, is determined. The selected bone contact surface 62a is placed flush against distal resected surface 01 and feet 72 are placed against the posterior condyles such that reference surfaces 74a thereof contact the bone. This contact with the posterior condyles references the posterior condylar axis of femur 00. Reference pins 16 are inserted into guide holes 65. A plane bisecting reference holes 65 is externally rotated at a predetermined angle relative to the posterior condylar axis. This predetermined angle is preferably about 3 degrees, but can be 1 to 6 degrees. Once reference pins 16 are inserted, A/P guide 60 is removed therefrom while pins 16 remain in the bone.

Thereafter, a femoral component is sized using the A/P sizing/cutting guide 80. A/P guide is obtained and attached to reference pins 16 via guide holes 95 in second body 90. A/P guide 80 is then slid along pins 16 until the bone contact surfaces 109 and 92 of the first and second bodies 100, 90 lie flush against distal resected surface 01 of femur 00. At this point, posterior resection slot 98 and anterior resection slot 102 are similarly oriented to a plane bisecting guide openings 95. In addition, posterior resection slot 98 is positioned a predetermined distance from guide openings 95 so that a predetermined amount of bone, preferably corresponding to thickness of a posterior aspect of a femoral component, is removed from femur 00.

The height of resection member 105 of first body 100 is adjusted relative to second body 90 by sliding mating member 106 within recess 93, tongue 107 within groove 94, and elongate member 88 within opening 82. This is done until reference tip 127 of resections stylus 120 contacts an anterior cortex 02 of femur 00. If needed, the length of stylus 120 can be adjusted to reach anterior cortex 02 by sliding first elongate portion 122 through groove 114 in connection bolt 110, and connection bolt 110 through elongate slot 129 in first elongate portion 122. The location of tip 127 indicates a run-out location of saw blade 12 inserted through anterior resections slot 102.

Once anterior cortex 02 is properly contacted with stylus 120, a femoral prosthesis size can be determined by observing a marking 89 on elongate member 88 relative to indicia 81 on second body 90. Stylus 120 can be removed by sliding along connection bolt 110 until connection bolt 110 is positioned within circular opening 128 and then lifted away from connection bolt 110. Connection bolt 110 can also be removed by twisting attachment bolt 110 until protrusion 113 is released from groove 86 and then lifted away from first body 100.

Figure 9:
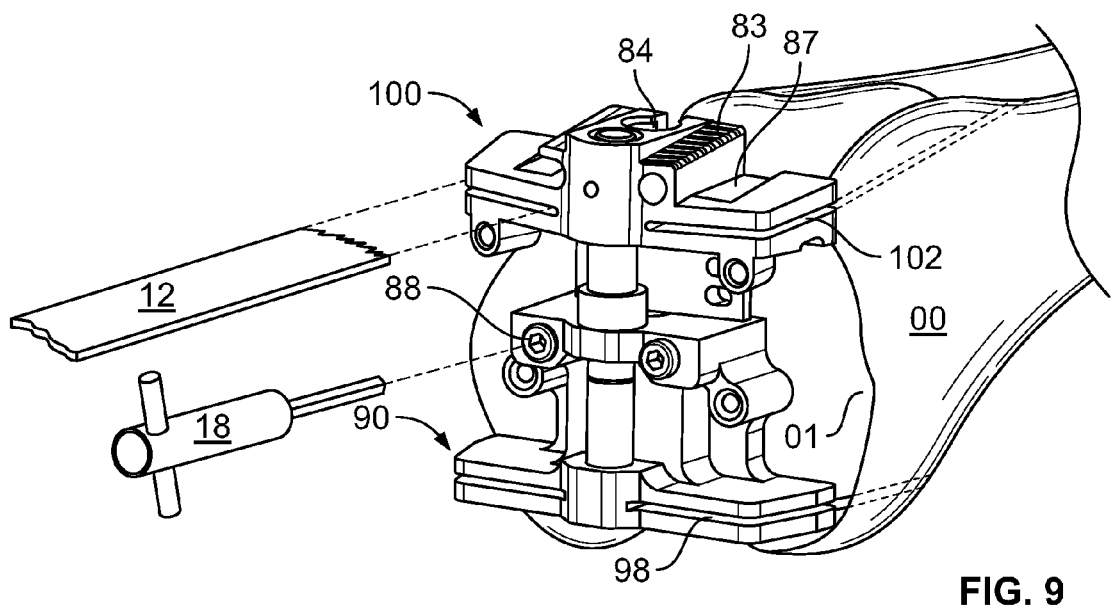

After a femoral prosthesis size is determined, retaining screws 88 are driven via driver 18 through retaining holes 97 of second body 90 and into retaining holes 108 of mating member 106 (best shown in FIG. 9). This helps firmly fix first body 100 relative to second body 90 for resection. Thereafter saw blade 12 is inserted through posterior and anterior resection slots 98, 102 (best shown in FIG. 9) to remove bone and form anterior and posterior resected surfaces. The distance between the anterior and posterior resected surfaces is substantially equal to an A/P dimension of a femoral prosthesis. Thereafter, first and second bodies 100, 90 are removed from reference pins 16 while leaving reference pins 16 within the bone.

Figure 10:
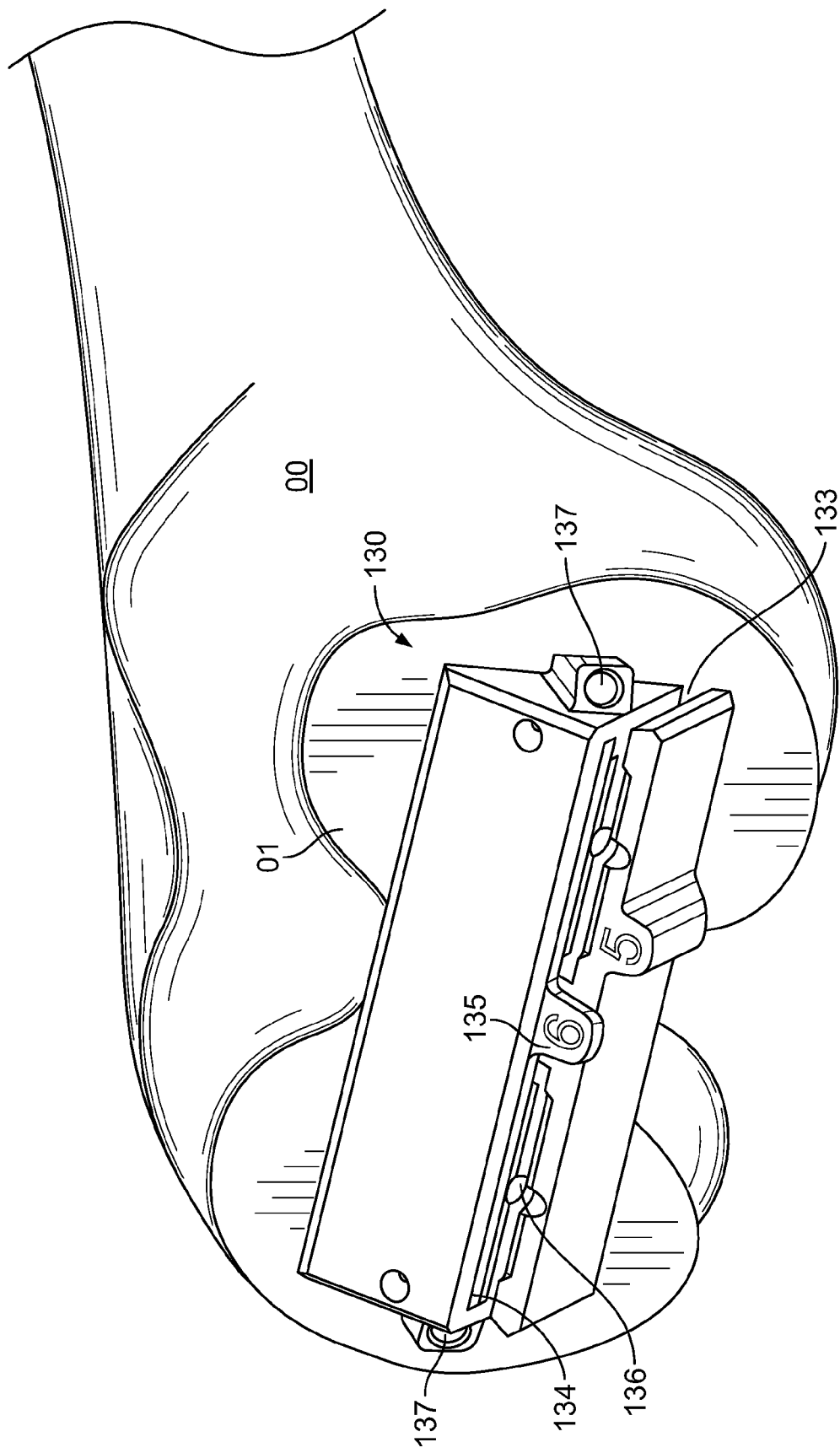
FIG. 10 illustrates a method of using the chamfer resection block of FIG. 5A.

Thereafter, anterior and posterior chamfer resections are performed using chamfer resection block 130. As illustrated in FIG. 10, bone contact surface 138 of chamfer resection block 130 is placed flush against distal resected surface 01. Although, reference pins 16 are not shown in the figure, chamfer block 130 is placed over reference pins 16 via guide holes 136 and slid along pins 16 until block 130 abuts bone. The orientation of pins 16, which was initially determined by A/P guide 60, helps determine the I/E orientation of chamfer resection block 130. In addition, the size of femoral component determined by A/P guide 80 determines the side of shim 135 at which the anterior chamfer resection is to be performed.

Once resection block 130 is positioned against the bone, bone pins are inserted into angled pinholes 137 to prevent rotation of chamfer block 130 and to prohibit movement away from the bone during resection. Reference pins 16 are then removed.

Saw blade 12 is inserted through nonadjustable slot 133 and is used to cut through femur 00 to remove a segment of bone and to form a posterior chamfer resected surface. Saw blade 12 is also inserted through adjustable/floating slot 134 at a first or second side of shim 135 based on a size of a prosthesis, as was determined using A/P guide. For example, as shown, where a size of the prosthesis is determined to be a size 6, less bone is removed and saw blade 12 is inserted through slot 134 at a first side or anterior side of shim 135. Where a size 5 is determined, more bone is removed and saw blade 12 is inserted through slot 134 at a second side or posterior side of shim 135. Saw blade 12 cuts femur 00 to remove a segment of bone and form an anterior chamfer resected surface. Thereafter, bone pins and chamfer cutting block 130 are removed from femur 00.

Figure 11A:
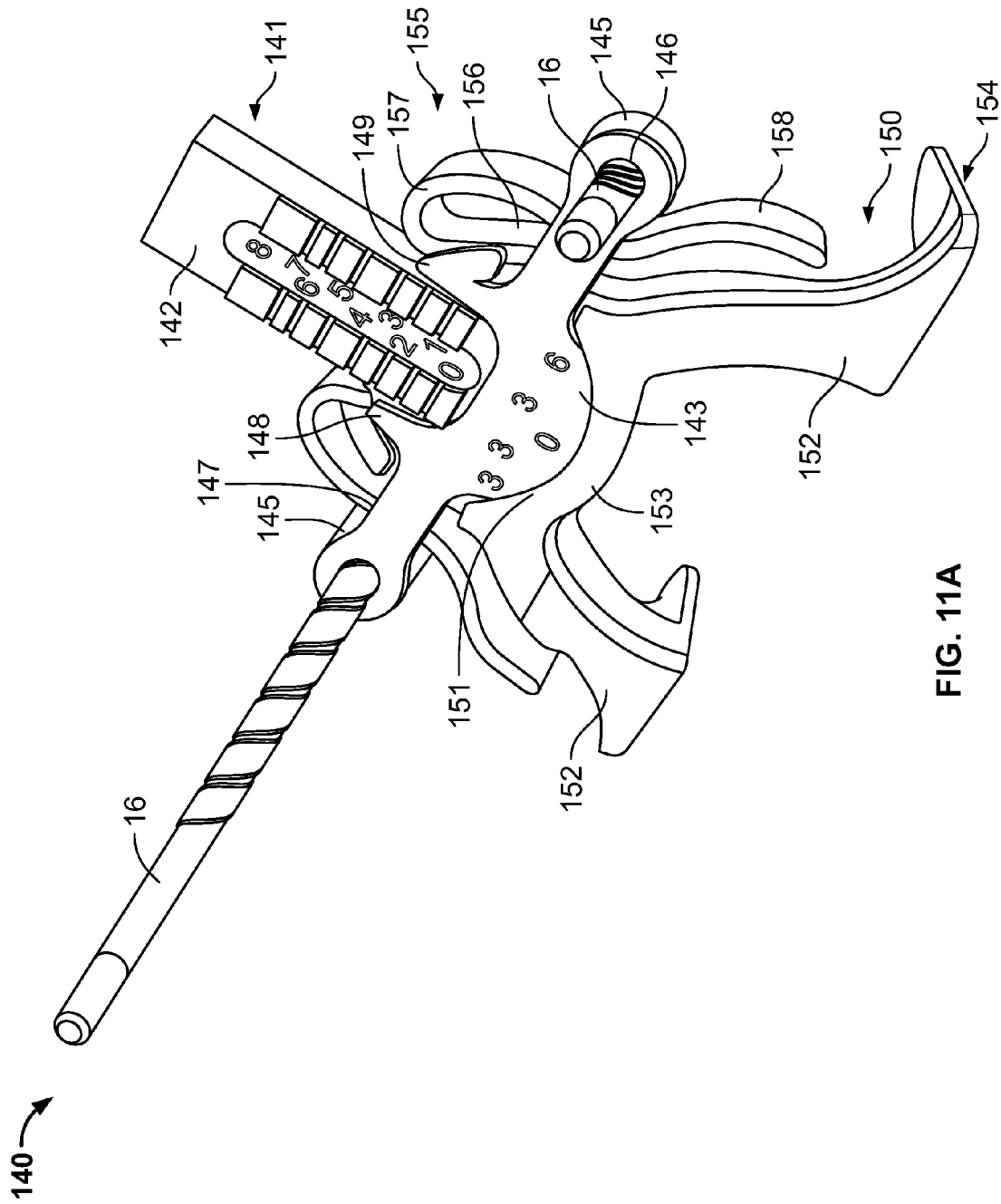
FIG. 11A is a front perspective view of an A/P reference/sizing guide according to another embodiment of the present disclosure.

FIG. 11A depicts an alternative A/P sizing and/or referencing guide 140, which may be used in lieu of A/P guide 60 and may be used in a posterior referencing technique/philosophy. A/P guide 140 generally includes a first body 150 and as second body 141.

First body 150 or lower body generally includes a pair of legs 152 connected by an intermediate portion 153. Intermediate portion 153 is curved to form a generally concave articulating surface 151. Markings are located on intermediate portion 153 adjacent to concave surface 151, which may be used to determine an orientation of second body 141 relative to first body 150. Each leg 152 includes a foot 154 extending therefrom in a single direction transverse to legs 152. Each foot 154 includes a reference surface 159 for contacting a posterior condyle.

A spring-arm 155 is cantilevered to each leg 152 and extends away from each leg 152 in an upward direction, curves outwardly and then extends downwardly. Thus, each spring-arm 155 includes an upwardly extending portion 156, a curved portion 157, and a downwardly extending portion 158, which terminates a terminal end thereof. Spring-arms 155 are flexible. Each spring-arm 155 can be flexed in a lateral-medial direction at their respective connections with legs 152. In addition, downwardly extending portions 158 are outwardly biased yet can be moved inwardly toward upwardly extending portions 156 about the curved portion 157 upon application of a force.

Teeth or protrusions 149 extend from spring-arms 155 in a direction transverse to a length of each arm 155. Such teeth include outer surfaces shaped to articulate with corresponding teeth 148 of second body 141.

Second body 141 or upper body generally includes a planar bone contact surface (not shown) for contacting a distal resected surface and a convex articular surface 143 that articulates with concave articular surface 151 of first body 150. Indicia are located on second body 141 adjacent convex surface 143, which may be used in conjunction with the markings on first body 150 to determine an orientation of second body 141 relative to first body 150. Second body 141 also includes teeth 148 or protrusions for engaging teeth 149 of first body 150.

A post 142 extends from second body 141 in a direction opposite convex surface 143. Post 142 includes indicia that can be used to size a femoral component. For example, another device, such as a bone contact plate (not shown) can be slidably attached to post 142 and include a marker for correspondence with the indicia to indicate a femoral prosthesis size.

Lateral and medial extensions 145 extend from body 141 in a lateral-medial direction transverse to post 142 and each include a channel 147 extending therethrough for receipt of a corresponding spring-arm 155. A guide opening 146 extends through a terminal end of each extension 145.

When first and second bodies 150, 141 are assembled, second body 141 is disposed within the space between spring-arms 155. Each spring-arm 155 extends through a corresponding channel 147 formed through extensions 145 such that curved portion 157 is positioned on one side of an extension 145, and the terminal end of spring-arm 155 is positioned on another side of extension 145. Convex and concave articular surfaces 143, 151 abut each other, and post 142 extends out from the space between spring-arms 155.

Teeth 149 and 148 of first and second bodies 150, 141 engage one another. As mentioned above, teeth 149 of first body 150 have outer surfaces that allow teeth 148 of second body 141 to articulate therewith. This articulation occurs during rotation of second body 141 relative to first body 150.

Spring-arms 155 have first and second conditions. In the first condition, spring-arms 155 press against their corresponding extension 145 from the inside of channels 147 under the natural bias of spring-arms 155. This prevents second body 141 from being rotated relative to first body 150. In the second condition, downward extending portion 158 of each spring-arm 155 is moved toward a corresponding leg 150 such that the spring-arm 155 no longer contact extension 145, or at least provide very light contact. Second body 141 can rotate when spring-arms 155 are in the second condition.

Figure 11B:
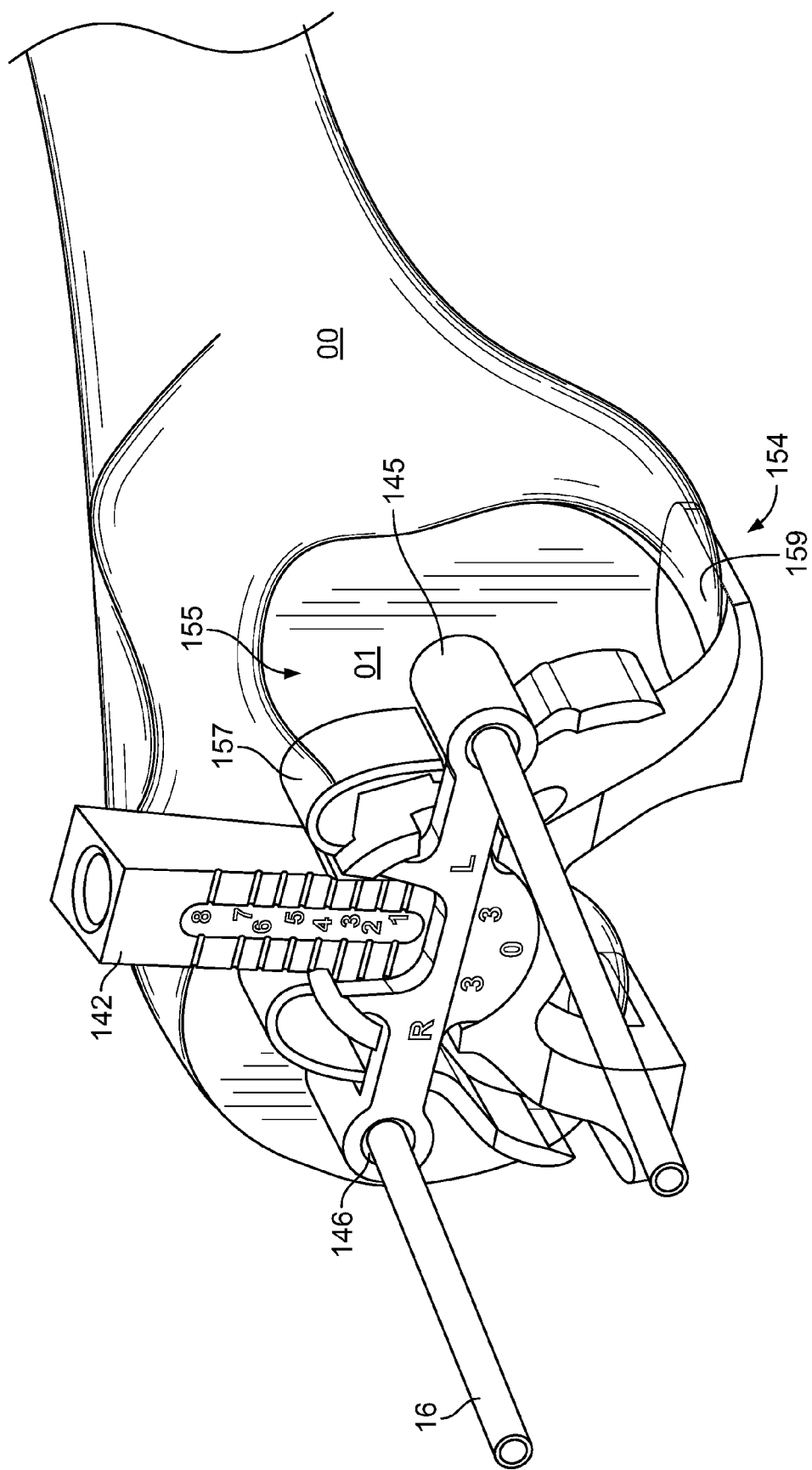
FIG. 11B illustrates a method of using the A/P reference/sizing guide of FIG. 11A.

In a method of use, which is depicted in FIG. 11B, A/P guide 140 is placed against femur 00 such that the bone contact surface lies flush against distal resected surface 01 of femur 00 and reference surface 159 of feet 154 contact corresponding posterior condyles.

As shown, second body 141 may be in a neutral position (0 degrees) relative to first body 150 in which guide openings 146 are aligned with reference surfaces 159 of feet 154 such that a plane bisecting guide openings 146 is parallel to a plane defined by reference surfaces 159. Other positions may be selected, such as 3 degrees of external rotation in which guide openings 146 are oriented 3 degrees relative to reference surfaces 159, for example. In order to adjust second body 141 to alternative positions, spring-arms 155 are compressed moving them from the first condition to the second condition, and second body 141 is rotated until the indicia indicate the desired angle of rotation. During rotation, teeth 148 of second body 141 push teeth 149 of first body 150, and consequently upwardly extending portion 156, outwardly providing tactile feedback to the operator. Second body 141 can be rotated in either direction making it universal to a right and left leg. When in the desired angular position of second body 141 is achieved, spring-arms 155 are released to the first condition, which locks second body 141 in the new orientation. A/P guide 140 can achieve a number of different orientations and preferably can achieve 0 and +/−3 degrees. In other embodiments, A/P guide can achieve 0 to +/−6 degrees of rotation. The desired orientation of guide holes 146 relative to reference surfaces 149 can be set prior to or after contacting femur 00.

Once the desired orientation of second body 141 relative to first body 150 is achieved, reference pins 16 are inserted into guide holes 146 and A/P guide 140 is removed from femur 00 while leaving reference pins 16 in place for use by A/P sizer 80 and chamfer block 130.

FIGS. 12A-12D depict an alternative distal resection assembly 160, which is configured for both anterior and posterior referencing techniques/philosophies, unlike referencing guide assembly 20, which is configured for posterior referencing. Distal referencing assembly 160 can also be used for MA and AA alignment and a measured resection technique/philosophy. Distal referencing assembly 160 includes a distal referencing guide 170, a multicut guide 190, connection bolt 120, and a skim stylus 200.

Distal referencing guide 170 is similar to distal referencing guide 30 in that it includes a body 171 and an alignment guide 180 and is universal to a right and left leg. In addition, body 171 is similar to body 21 in that body 171 includes a plate portion 172, planar bone contact surface 178, block portion 176, toggle-hole 177 forming a rim, utility openings 161, protrusions 179, ovular boss 175 and an angled pin hole 174.

However, distal referencing guide differs from referencing guide in that ovular boss 175 extends further from body 171 than in referencing guide 30. This creates a clearance space between body 171 and alignment guide 180 for multicut guide 190, as is described in further detail below.

In addition, the body 171 includes a retaining opening 162 that intersects with one of utility openings 161. Retaining opening 162 may be threaded and is sized to receive a retaining fastener therein for firmly gripping an elongate member 199 of multicut guide 190 to prevent movement of multicut guide 190 during a skim cut (described further below).

Alignment guide 180 is rotatably connected to a hinge extension 182 extending from body 171. Hinge extension 182 defines a rotation axis of alignment guide 180. Alignment guide 180 includes first and second alignment holes 186a and 186b and is generally bow-tie shaped. This shape provides a low profile to make space for multicut guide 190 when an alignment hole 186a-b is positioned over toggle-hole 177. Each alignment hole 186a and 186b is partitioned into first and second circular portions 187a and 187b by opposing protrusions 185, which gives each alignment hole 186a-b a partial snowman-like shape. Circular portions 187a and 187b are in fluid communication with each other and can each receive an elongate rod therein without the elongate rod traversing to the other circular portion as it is prohibited from doing so by protrusions 185. The fluid communication between circular portions 187*a* and 187*b* allows them to be closely spaced, which reduces the overall profile of alignment guide 180.

Circular portions 187*a* and 187*b* of each opening 186*a* and 186*b* are positioned relative to the rotational axis of alignment guide 180 such that when each circular portion 187*a-b* is aligned with toggle opening 177, toggle opening 177 and circular portion 187*a* or 187*b* define an axis that has a different angle relative to bone contact surface 178 than the other circular portion. Each of these angles corresponds to a different varus-valgus angle. For example, first circular 187*a* portion of first alignment hole 186*a* may be associated with a 4 degree varus-valgus angle, while second circular portion 187*b* of first alignment hole 186*a* may be associated with a 5 degree varus-valgus angle. In addition, first circular portion 187*a* of the second alignment hole 186*b* may be associated with a 6 degree varus-valgus angle, while second circular portion 187*b* of second alignment hole 186*b* may be associated with a 7 degree varus-valgus angle. Thus, when first circular portion 187*a* of first alignment hole 186*a* is aligned with toggle-hole 177, an axis formed thereby is oriented 4 degrees from a normal axis perpendicular to bone contact surface 178 or 86 degrees relative to bone contact surface 178. This allows for bone contact surface 178 to be positioned at various angles in relation to an IM rod extending from femur 00 and inserted into toggle-hole 177 and one of circular portions 187*a-b* of one of alignment holes 186*a-b*. In short, the combination of alignment member 180 and toggle-hole 177 can be used to establish varus-valgus alignment of referencing guide 170 relative to femur 00 during a TKA procedure.

The various angles formed by the alignment of toggle-hole 177 and circular portions 187*a-b* of alignment holes 186*a-b* can be achieved by the structure of the depicted embodiment. In the depicted embodiment, circular portions 187*a-b* of each alignment hole 186*a-b* are positioned adjacent one another along a circular arc. Such arc may have a center point, which itself is offset from the rotation axis of alignment member 180. Thus, when alignment member 180 is rotated and each circular portion is passed over toggle-hole 177, each circular portion 187*a-b* is positioned over toggle-hole 177 in a different lateral-medial location than the other circular portions. For example, when first circular portion 187*a* of first alignment hole 186*a* is positioned over toggle-hole 177, first circular portion 187*a* is positioned closer to hinge extension 182 in a lateral-medial direction than when second circular portion 187*b* of first alignment hole 186*a* is positioned over toggle-hole 177.

This construction consolidates multiple referencing guides that would typically be needed to perform the same functions, thereby reducing the number of instruments needed in the operating theater.

Multicut guide 190 includes a body 191 and elongate members 199 extending from body 191 for sliding connection to utility openings 161 of referencing guide 170. Body 191 is similar to body 51 of the distal cutting guide 50 in that body 191 includes adjustment pinholes 198, angled pinholes 197, and opposing cutting guide surfaces defining a distal resection slot 195.

However, body 191 differs from body 51 in that it includes a connection bolt opening 164, which is similar to connection bolt 84 opening of A/P guide 80. As such, connection bolt opening 164 preferably includes a groove (not shown) for receipt of connection bolt protrusion 113.

Body 191 also includes a skim cut slot 163 extending therethrough in a direction transverse to distal resection slot 195. In addition, skim cut slot 163 intersects distal resection slot 195. Such intersection is preferably at an angle between about 85 and 90 degrees or 5 to 0 degrees from horizontal. In one embodiment, the angle formed between the intersection of skim cut slot 163 and distal resection slot 195 is 88 degrees or 2 degrees from horizontal. A platform portion 192 extends from body adjacent to skim cut slot 163. Elongate members 199 are connected to platform portion 192. Platform portion 192 includes a planar surface 193 continuous with a resection guide surface that partially defines skim cut slot 163. Such planar surface 193 helps guide a saw blade.

As shown, distal resection slot 195 is a nonadjustable slot. However, in some embodiments, distal resection slot 195 can include a shim, similar to shim 54 of cutting guide 50 for removing differing amounts of bone from femur 00. However, such shim may include a transverse slot (not shown) extending therethrough, which may align with skim cut slot 163 when connected to body 191, such as by a pair of rails 52. Such a transverse slot allows a bone saw blade to pass through skim cut slot 163 unimpeded. In other embodiments, the shim may be dimensioned such that it would terminate before reaching the intersection of skim cut slot 163 and distal resection slot 195.

Body 191 includes a cut-out region at a lower end thereof. Such cut-out region forms a bottom surface 166 and a flange portion 167 having a downwardly depending surface 168 intersecting bottom surface 166. Flange portion 167 is offset from elongate members 199 so as to form a gap therebetween. Such flange portion 167 is dimensioned to fit within a space created between body 171 and alignment guide 180 of distal referencing guide 170. Distal resection slot 195 preferably extends through the flange portion 167. However, it should be understood that some embodiments of body 191 may not include flange portion 167.

Connection bolt 120 is the same as that previously described. Skim stylus 200 is similar to the resection stylus 110 in that it includes a first, second, and third elongate portions 202, 204, 206. In addition skim stylus includes a circular opening 208 and elongate slot 209 in communication therewith. However, skim stylus 200 is generally longer than resection stylus 110. In addition, the angles between each portion 202, 204 and 206 are generally shallower than that of resection stylus 110. This is generally due to a tip of skim stylus 207 referencing a run-out of an anterior skim cut, which is generally performed at a shallower angle than an anterior resection.

Figure 12A:
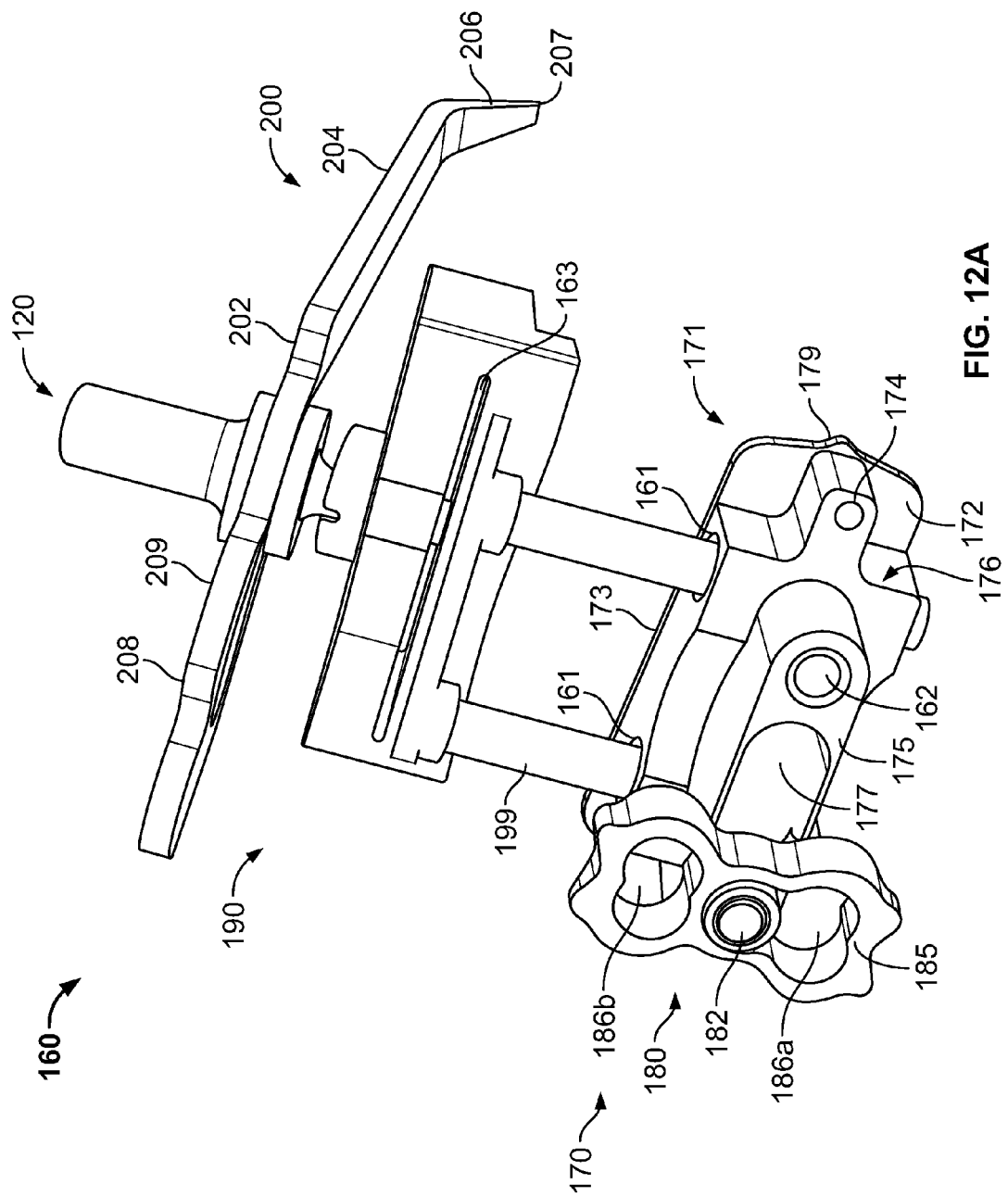
FIG. 12A is a front perspective view of a distal resection assembly including a distal referencing guide and a multicut guide according to another embodiment of the present disclosure.
Figure 12B:
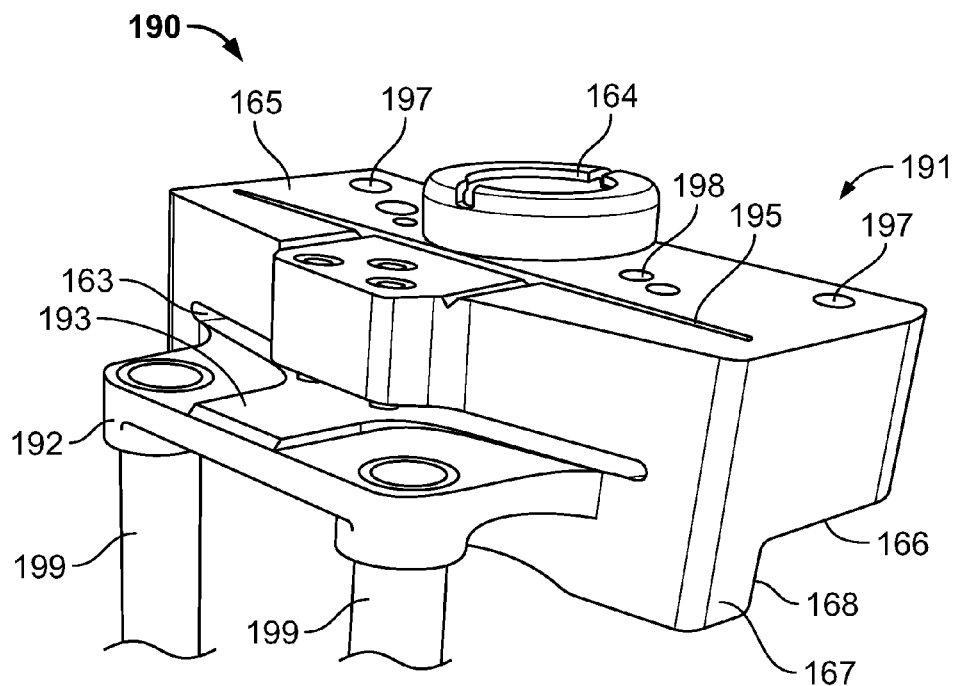
FIG. 12B is a partial front perspective view of the multicut guide of FIG. 12A.
Figure 12C:
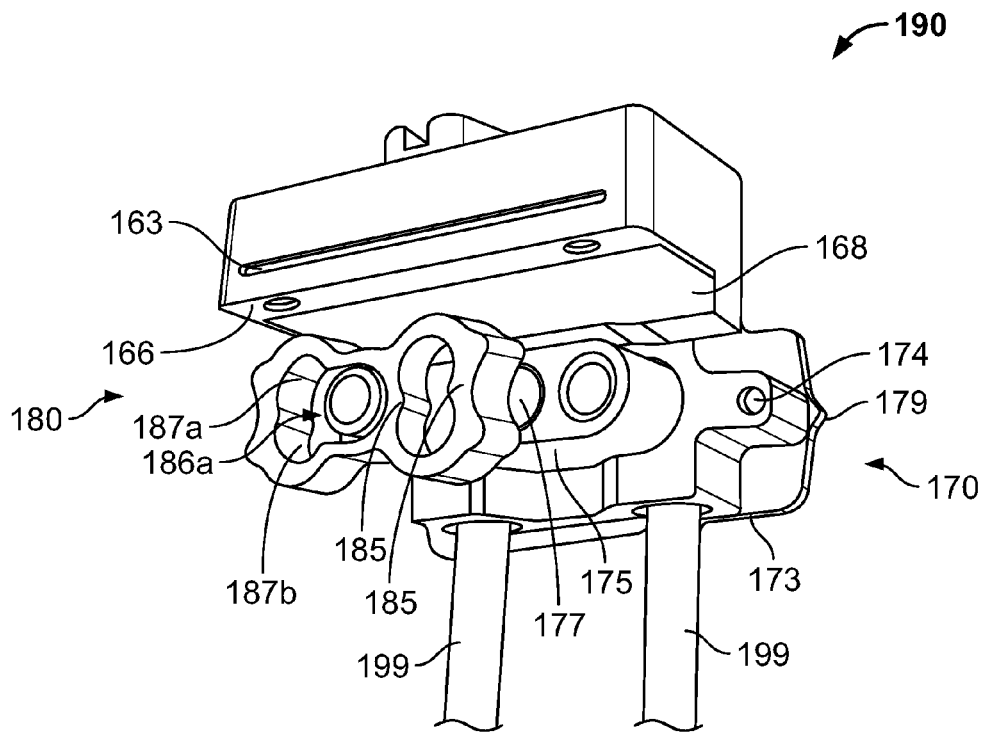
FIG. 12C is a front perspective view of a distal referencing guide and multicut guide of FIG. 12A assembled in a first condition.

FIG. 12C depicts multicut guide 190 assembled with distal referencing guide 170 in a first condition or skim cut condition. In this condition, elongate members 199 are slidingly connected to utility openings 161 of distal resection guide 170. Additionally, body 191 overhangs alignment guide 180 and flange portion 167 of multicut guide 190 is disposed between alignment guide 180 and body 171 and positioned over the ovular boss 175. This allows bone contact surface 178 of the referencing guide 170 to be positioned adjacent a distal femur without interference from body 191 of multicut guide 190 so that skim cut slot 163 can be properly positioned relative to femur 00. In other words, the first condition of distal resection assembly 160 allows skim cut slot 163 to be positioned posterior to an anterior surface of femur 00. At their closest, platform portion 192 or flange portion 167 of multicut guide 190 abuts block portion 176 of distal referencing guide 170, which sufficiently spaces bottom surface 166 of multicut guide 190 from alignment guide 180 to allow alignment guide 180 to be rotated so as to position any of circular portions 187*a* or 187*b* of alignment holes 186*a-b* in alignment with toggle-hole 177.

Figure 12D:
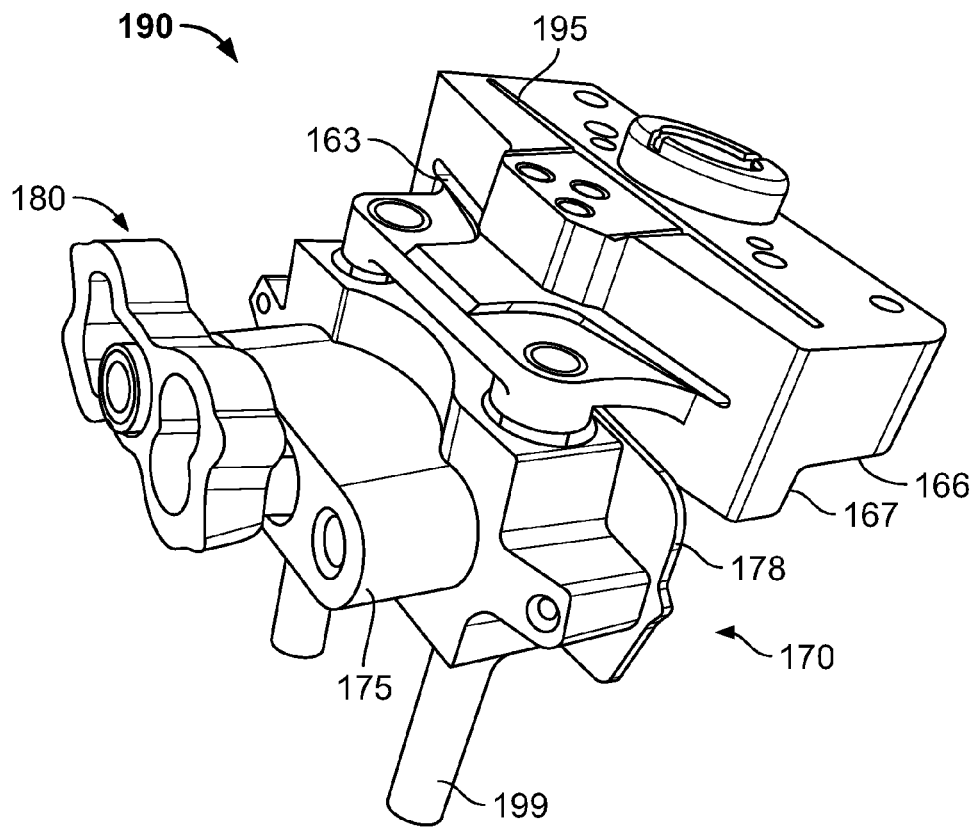
FIG. 12D is a front perspective view of a distal referencing guide and multicut guide of FIG. 12A assembled in a second condition.

FIG. 12D depicts multicut guide 190 assembled with distal resection guide 170 in a second condition or distal resection condition. In this condition, elongate members 199 are slidingly connected to utility openings 161 of distal resection guide 190 and body 191 is reversed from its position in the first condition. As such, body 191 extends beyond bone contact surface 178 so that distal resection slot 195 can be positioned proximal of a distal extent of femur 00. At their closest, platform portion 192 of multicut guide 190 abuts plate portion 172 of referencing guide 170 and plate portion 172 is at least partially disposed in the space between flange portion 167 and elongate members 199.

Figure 13:
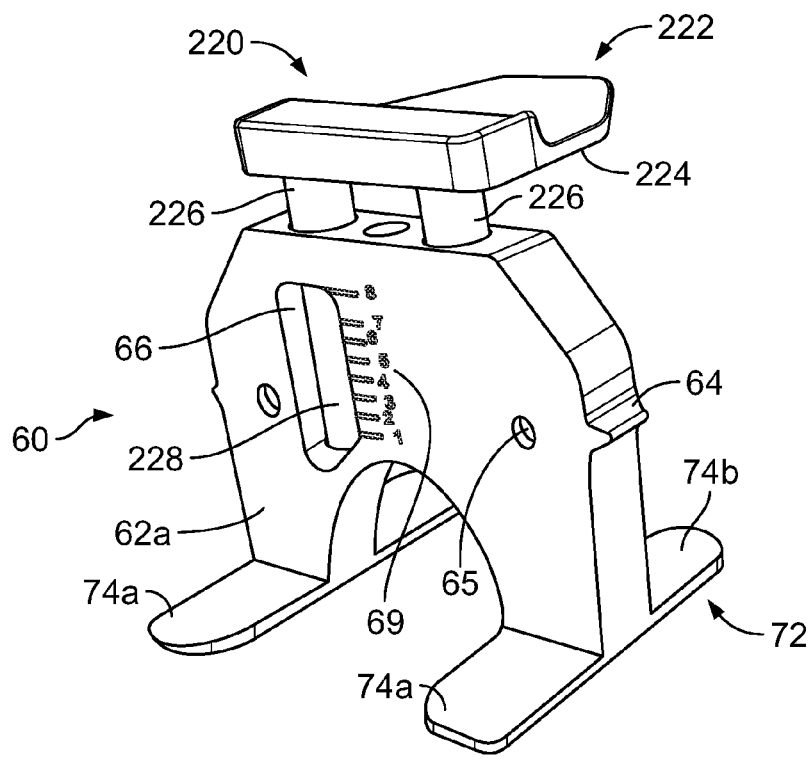
FIG. 13 is a front perspective view of the A/P reference/sizing guide of FIG. 3 according to another embodiment of the present disclosure including a reference plate assembled thereto.

FIG. 13 depicts A/P guide 60 configured for an anterior referencing technique/philosophy. The configuration 210 of A/P guide 60 for anterior referencing includes a reference plate 220. Reference plate 220 generally includes a plate portion 222 or body that includes a planar reference surface 224 for contacting an anterior skim cut surface. Elongate members 226 are attached to plate portion 222 at one end thereof and extend therefrom. Elongate members 226 are preferably oriented at about 92 degrees relative to reference surface 224 of plate portion 222. However, in some embodiments this orientation may be about 90 to 95 degrees. Each elongate member 226 includes a marking 228, such as an indicator line for indicating a prosthesis size.

Reference plate 220 can be assembled to A/P guide 60 such that plate portion 222 can overhang either side of A/P guide 60. Thus, reference plate 220 and A/P guide 60, in combination, are universal to a right and left leg. When connected to A/P guide 60, reference surface 224 of plate portion 222 is oriented preferably about 2 degrees relative to a plane defined by reference surfaces 74a-b of feet 72. However, this orientation can be about 0 to 5 degrees. In addition, height of plate portion 222 relative to A/P guide 60 can be adjusted by sliding elongate members 226 through utility openings 67. This moves marking 228 relative to indicia 69 formed on A/P guide 60 to determine a femoral prosthesis size.

Thus, as described herein, A/P guide 60 can be used for both sizing and establishing I/E rotation. In addition, A/P guide 60 can be used to perform anterior and posterior referencing, which when combined with the other instruments described herein, in particular A/P guide 80, helps to consolidate multiple conventional instruments that may be required to perform both techniques/philosophies and functions.

Figure 18:
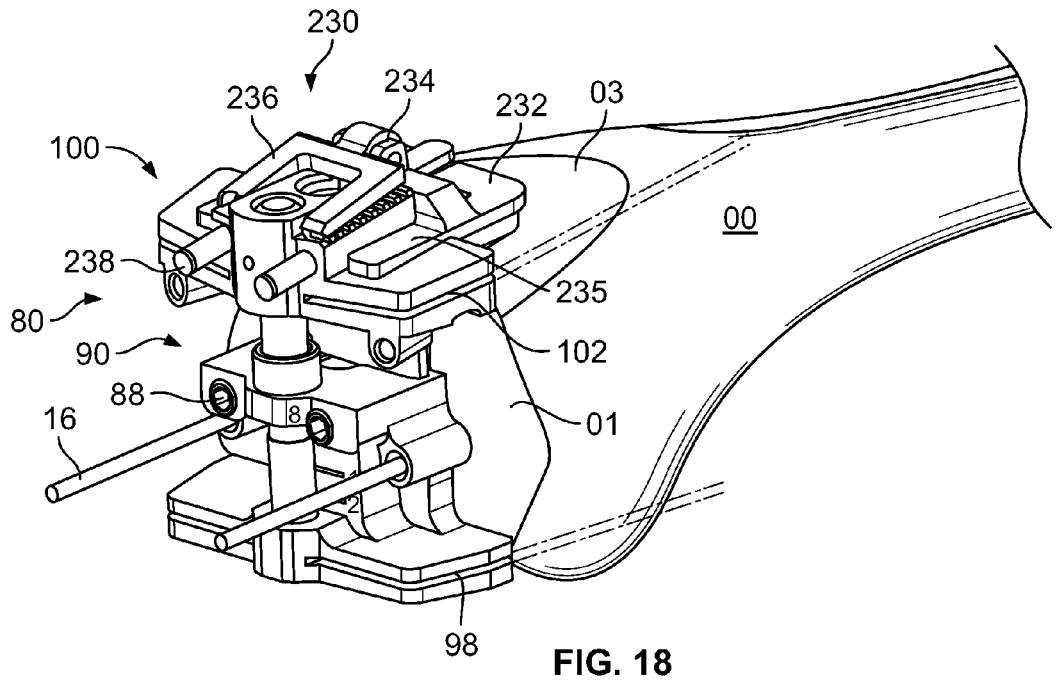
FIG. 18 illustrates a method of using the A/P cutting/sizing guide of FIG. 4A including a reference plate according to another embodiment of the present disclosure.

FIG. 18 depicts A/P guide 80 configured for an anterior referencing technique/philosophy. The configuration of A/P guide 80 for anterior referencing includes a reference plate 230 in lieu of connection bolt 110 and resection stylus 120. Reference plate 230 generally includes a plate portion 232, fork portion 236, and elongate members 238.

Plate portion 232 includes a planar bone contact surface (not shown) for contacting an anterior skim cut 03. At least one extension 235 extends from plate portion 232 and has a surface continuous with the bone contact surface. Extension 235 is generally rectangular in cross-section and is sized to fit in indented region 87 of first body 100 of A/P guide 80.

Elongate members 238 generally extend in the same direction as extension 235 and are sized to fit within utility openings 103a and 103b of first body 100 of the A/P guide 80.

Fork portion 236 is hingedly connected to plate portion 232 and includes at least one miniature protrusion (not shown) for engaging a notch in notched surface 83 of first body 100.

When connected to A/P guide 80, elongate members 238 extend through utility openings 103a and 103b and are slidingly adjustable therein. Extension 235 rests on indented region 87, which help stabilize plate portion 232 and helps establish a slope angle of plate portion 232 relative to bone contact surfaces 92 and 109 of A/P guide 80. Such angle is preferably about 92 degrees, but can be about 90 to 95 degrees. Fork portion 236 contacts notched surface 83 and engages at least one notch thereof to prevent reference plate 230 from moving in a proximal-distal direction.

Thus, as described herein, A/P guide 80 can be used to size a femoral prosthesis and guide an anterior and posterior resection of femur 00. In addition, A/P guide 80 can be used in an anterior and posterior referencing techniques/philosophies, which when combined with the other instruments described herein, in particular A/P guide 60, helps to consolidate multiple conventional instruments that may be required to perform both techniques/philosophies and functions.

FIGS. 5A-5B, 12A-13, and 18 depict a second set of devices which, as a set, can perform MA/AA alignment, measured resection, and posterior/anterior referencing techniques/philosophies. A method of using these instruments to perform an MA alignment, measured resection and anterior referencing techniques/philosophies is illustrated in FIGS. 10 and 14-18 and is now described.

In a TKA procedure, after the knee joint is exposed, an IM rod 10 is placed within the IM canal such that IM rod 10 at least partially extends from the distal end of femur 00. IM rod 10 can be a portion of an IM reamer, which reams through the distal end of the femur into the IM canal. At this point, IM rod 10 is substantially aligned with an AA axis of femur 00.

The orientation of the MA axis is determined relative to the AA axis, which is typically oriented 3 to 7 degrees from the AA axis. Distal referencing guide 170 is obtained and a varus-valgus angle is determined, which may correspond with the angular difference between the AA and MA axes. Alignment member 180 is rotated until the desired circular portion 187a or 187b of a respective alignment hole 186a-b corresponding with the determined varus-valgus angle is positioned over and aligned with toggle-hole 177. Thus, the orientation of distal resection 01 of femur 00 relative to the MA, in a MA alignment philosophy/technique, helps determine, which alignment hole 186a-b and circular portion 187a-b is selected. For example, where it is desired to perform a distal resection perpendicular to the MA and the MA is oriented 5 degrees relative to the AA, first alignment hole 186a and second circular portion 187b corresponding to 5 degrees varus-valgus is selected.

Figure 14:
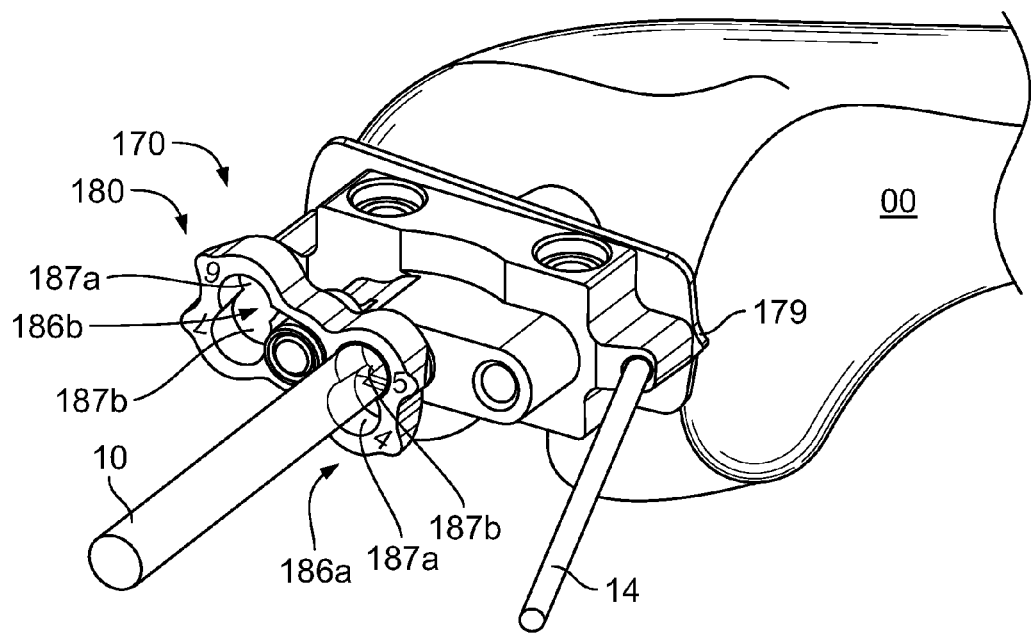
FIGS. 14-16 illustrate a method of using the distal resection assembly of FIG. 12A.

Once the desired circular portion 187b is aligned with toggle-hole 177, referencing guide 170 is slid onto IM rod 10 by passing IM rod 10 through toggle opening 177 and selected circular portion 187b of alignment hole 186a (best shown in FIG. 14). This aligns IM rod axis with an axis formed by toggle-hole 177 and circular portion 187b. Referencing guide 170 is slid along IM rod 10 until bone contact surface 178 abuts the distal femur. Due to the angle of IM rod 10 relative to bone contact surface 178, which is imposed by the alignment of toggle-hole 177 and circular portion 187b, bone contact surface 178 may only contact one distal condyle. At this point bone contact 178 surface aligns with the MA axis.

Distal referencing guide 170 can then be used to establish I/E rotation. This can be done by aligning protrusions 179 extending from reference edge 173 at lateral-medial locations thereof with the epicondyles (i.e., the epicondylar axis)

of femur 00. Alternatively, the angled portion of reference edge 173 can be aligned in parallel with the posterior condyles (i.e., the posterior condylar axis). The angle of reference edge 173 relative to a coronal plane bisecting referencing guide 170 is preferably 3 degrees or 2 to 6 degrees. Thus, when reference edge 173 is aligned in parallel with the posterior condylar axis, the remainder of referencing guide 170 is externally rotated as desired relative to the posterior condylar axis and, therefore, properly I/E oriented. In another alternative, distal referencing guide 170 can be aligned with Whiteside's line of femur 100. This can be done by attaching multicut guide 190 to distal referencing guide 170 in the first condition with connection bolt 120 attached to multicut guide 190. Connection bolt 120 can be aligned with Whiteside's line, thereby establishing proper I/E rotation. Once proper I/E rotation is established, a bone pin can be inserted through angled pinhole 174 to prevent further rotation of the referencing guide (best shown in FIG. 14).

Thereafter, multicut guide 190 is connected to referencing guide 170, which can take place either before or after connecting referencing guide 170 to IM rod 10. In addition, connection bolt 120 and skim stylus 200 is connected to multicut guide 190. Connection of multicut guide 190 is performed by inserting elongate members 199 into corresponding utility openings 161 in referencing guide 170 such that the assembly is in the first orientation, as described above (best shown in FIGS. 12C and 15). The height of multicut guide 190 relative to referencing guide 170 can be adjusted by sliding elongate members 199 within utility openings 161 until tip 207 of skim cut stylus 200 contacts anterior cortex 02 of femur 00, which indicates a blade runout of skim cut slot 163. Once anterior cortex 02 is referenced and the height of multicut guide 190 is determined, a retaining screw 88 can be adjusted using driver 18 until screw 88 firmly holds multicut guide 190 in place. At this point, skim cut slot 163 is positioned posterior of an anterior surface of femur 00.

Figure 15:
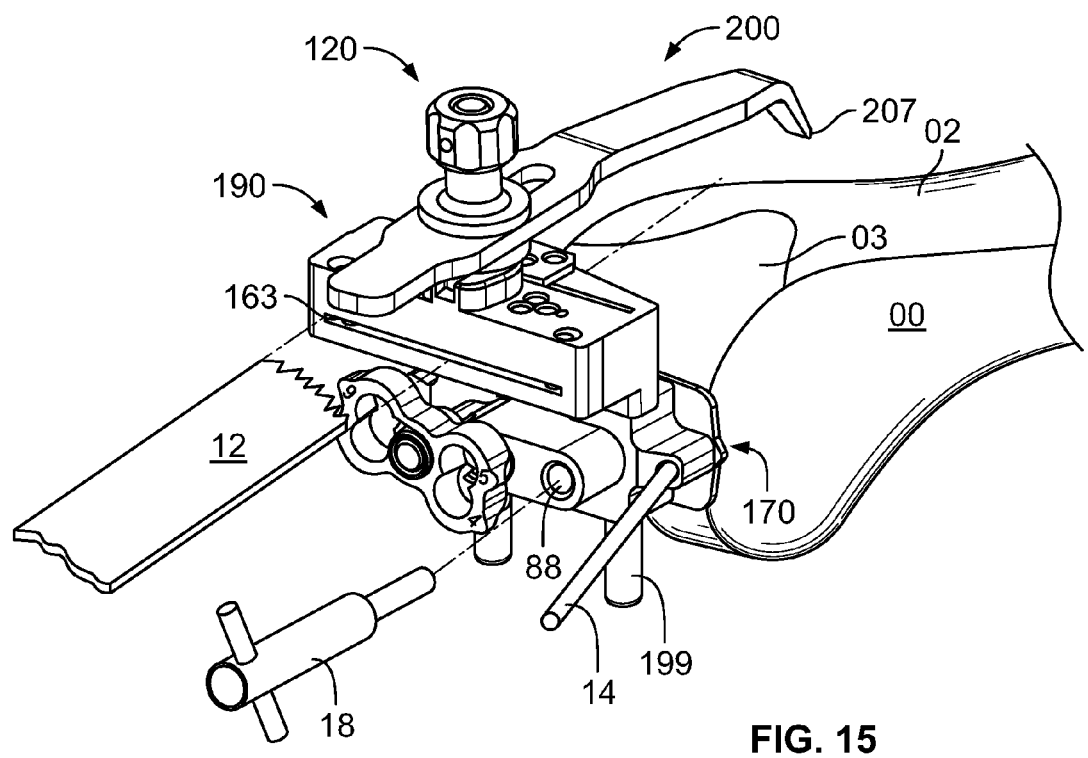
Figure 16:
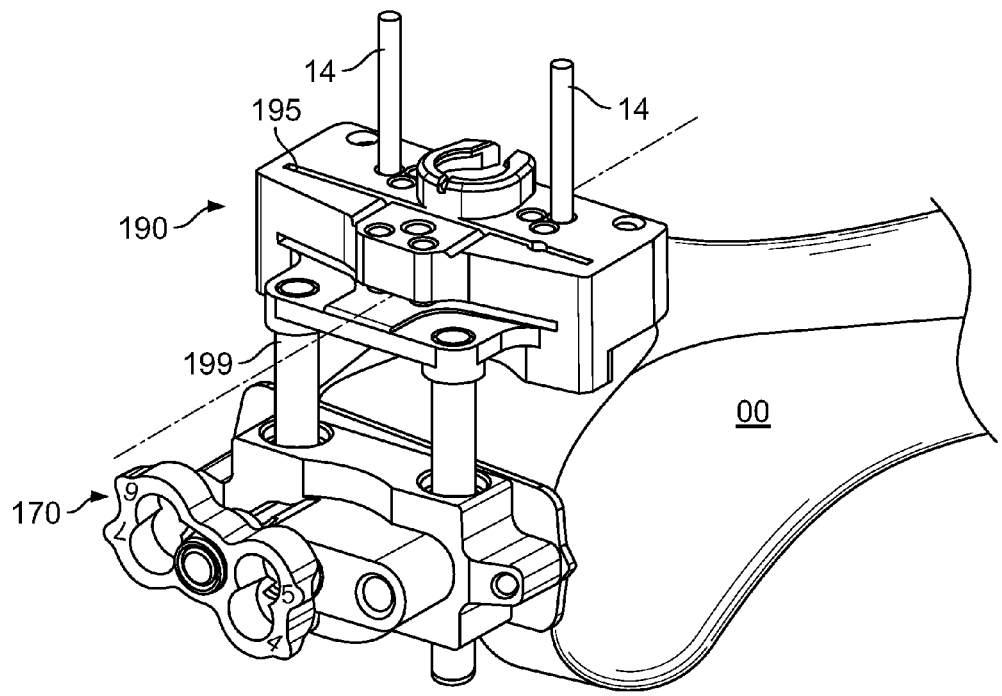

Thereafter, bone saw blade 12 is passed through skim cut slot 163, resects a portion of bone from an anterior aspect of femur 00, and forms a skim cut surface 03 or anterior reference surface (best shown in FIG. 15). Skim cut surface 03 has a slope that corresponds to a slope of skim cut slot 163 which, as mentioned above, is preferably about a 2 degree slope, but can be 0 to 5 degrees.

Once skim cut surface 03 is formed, connection bolt 120 and skim stylus 200 are removed from multicut guide 190 and multicut guide 190 is removed from referencing guide 170. Multicut guide 190 is then reconnected to referencing guide 170 such that assembly 160 is in the second condition, as described in detail above. The height of multicut guide 190 relative to referencing guide 170 is adjusted until multicut guide 190 contacts femur 00. At this point, distal resection slot 195 is positioned proximal to a distal extent of femur 00 (best shown in FIG. 16). Bone pins 14 are then placed through adjustment pinholes 198 and/or angled pinholes 197. IM rod 10 can be removed at this point along with any pins within distal referencing guide 170. However, IM rod 10 can be removed prior to the skim cut, particularly in embodiments where the referencing guide 170 is restrained by more than one pin within more than one angled pinhole 174. Bone saw blade 12 is then inserted through distal resection slot 195 and resects a predetermined amount of bone (according to a measured resection philosophy/technique) from the distal femur, thereby forming a distal resected surface 01. In the embodiments of multicut guide 190 that includes a shim, saw blade 12 can be inserted through either side of the shim depending on a distal thickness of a prefabricated femoral prosthesis. Once the distal resection is performed, further bone can be removed using adjustment pinholes 198 or by resecting on the second side of the shim if included in multicut guide 190. Resection assembly 160 may then be removed from femur 00.

As described above, in a posterior referencing technique/philosophy, A/P guide 60 is used to reference posterior condyles and establish I/E rotation. In addition, A/P guide 80, in a posterior referencing technique/philosophy, is used to size for a femoral component and perform anterior and posterior resections. In an anterior referencing technique/philosophy, A/P guide 60 is used to reference the anterior skim cut 03 and size for a femoral component, while A/P guide 80 is used to perform anterior and posterior resections.

Figure 17:
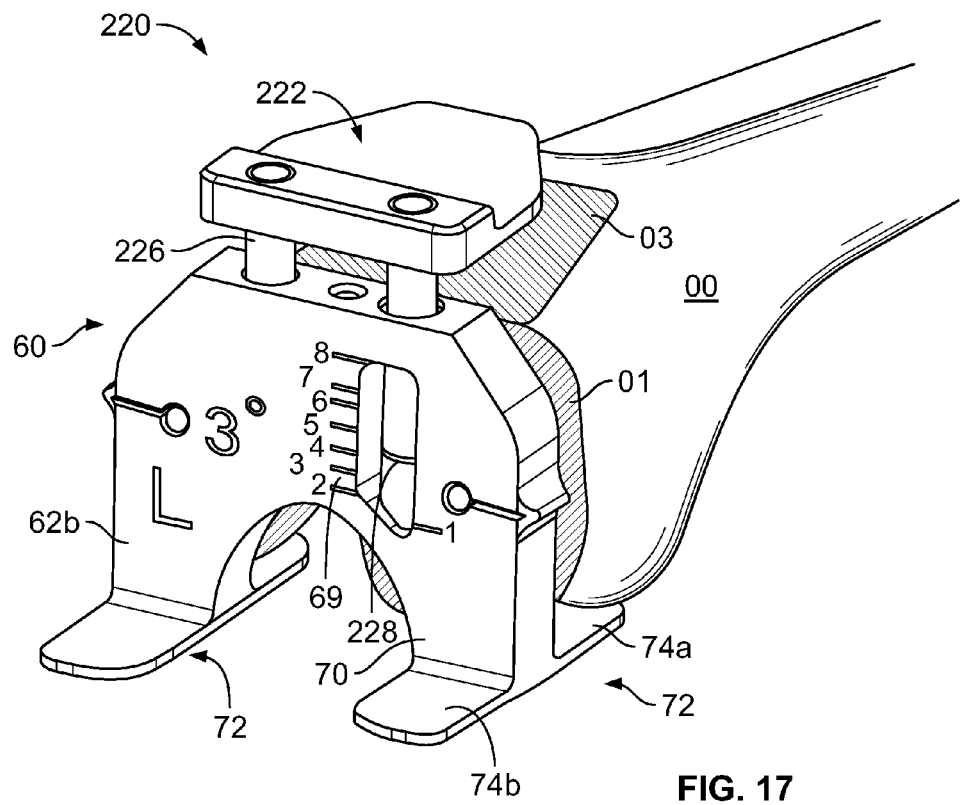
FIG. 17 illustrates a method of using the assembly of FIG. 13.

Thus, as illustrated in FIG. 17, once the skim cut is performed, reference plate 220 is connected to A/P guide 60, via elongate members 226 and utility openings 161, such that plate portion 222 overhangs the selected bone contact surface 62a, which depends on the leg, right or left. A/P guide 60 is placed adjacent to femur 00 such that reference surface 224 of reference plate 220 lies flush against skim cut surface 03 and the bone contact surface 62a of the A/P guide 60 lies flush against distal resected surface 01.

A/P guide 60 is then slid along elongate members 226 until one or both of reference feet 72 contact a posterior condyle. Once the posterior condyles are contacted by one or both of feet 72, a femoral prosthesis size is determined by viewing the alignment of marking 228 on one of elongate members 226 relative to indicia 69 on body 61 of A/P guide 60. Thereafter, A/P guide 60 can be removed from femur 100.

As illustrated in FIG. 18, the determined femoral prosthesis size is applied to A/P guide 80 by moving first body 100 relative to second body 90 until a marking 89 on elongate member 88 corresponds to the appropriate indicia 81 on second body 90. This position may be locked-in or set by driving retaining screws 88 through retaining holes 97 in first and second bodies 100, 90.

Reference plate 230 is attached to first body 100 by inserting elongate members 238 into utility openings 103a-b and extension 235 into indented region 87. Forked member 236 engages notched surface 83 to prevent proximal-distal movement of reference plate 230. The reference surface of reference plate 232 is placed flush against skim cut 03 and respective bone contact surfaces 92 and 109 of A/P guide 80 is placed flush against distal resected surface 01. Reference plate 230 can be adjusted proximally or distally, as needed, by rotating forked portion 236 away from first body 100 and sliding reference plate 230 proximally or distally. Thereafter, reference pins 16 are preferably inserted through guide openings 95 for stability and for use by chamfer resection block 130. However, it should be understood that reference pins 16 can be inserted through A/P guide 60 prior to using A/P guide 80.

Once A/P guide 80 is properly placed against femur 00, saw blade 12 is inserted through posterior and anterior resection slots 98, 102 to remove bone and form anterior and posterior resected surfaces. Anterior resection slot 102 has a slope, which is typically greater than that of skim cut slot 163 and preferably matches the slope of a surface of a femoral prosthesis. Such slope is preferably about 7 degrees. In addition, the distance between the anterior and posterior resected surfaces of femur 00 substantially corresponds to an anteroposterior dimension of a prosthesis having a size previously determined by A/P guide 60. A/P guide 80 is removed while reference pins 16 are left in place.

Thereafter, anterior and posterior chamfer resections are performed using chamfer resection block 130. As illustrated in FIG. 10, bone contact surface 138 of chamfer resection block 130 is placed flush against distal resected surface 01. Although, reference pins 16 are not shown in the figure, chamfer block 130 is placed over reference pins 16 via guide holes 136 and slid along pins 16 until block 130 abuts bone. The orientation of pins 16, which was initially determined by either A/P guide 60 or A/P guide 80, helps determine the I/E orientation of chamfer resection block 130. In addition, the size of the femoral component determined by A/P guide 60 determines the side of shim 135 at which the anterior chamfer resection is to be performed.

Once resection block 130 is positioned against the bone, bone pins 16 are inserted into angled pinholes 137 to prevent rotation of chamfer block 130 and to prohibit movement away from the bone during resection. Reference pins 16 are then removed.

A saw blade 12 is inserted through the nonadjustable slot and is used to cut through femur 00 to remove a segment of bone and to form a posterior chamfer resected surface. Saw blade 12 is also inserted through adjustable/floating slot 134 at a first or second side of shim 135 based on a size of a prosthesis, as was determined using A/P guide 60. For example, as shown, where a size of the prosthesis is determined to be a size 6, less bone is removed and the saw blade is inserted through slot 134 at a first side or anterior side of shim 135. Where a size 5 is determined, more bone is removed and saw blade 12 is inserted through slot 134 at a second side or posterior side of shim 135. Saw blade 12 cuts femur 00 to remove a segment of bone and form an anterior chamfer resected surface. Bone pins 16 and chamfer cutting block 130 are removed.

As previously mentioned, the devices depicted in FIGS. 5A-5B and 12A-13 can also be used in a posterior referencing technique. A method of forming a distal femur in accordance with such technique using these devices is virtually identical to the method described in relation to FIGS. 6-10. In addition, it should be understood that distal resection guide 50 can also be used with distal referencing guide 170 to perform a distal resection of femur 00.

Figure 19A:
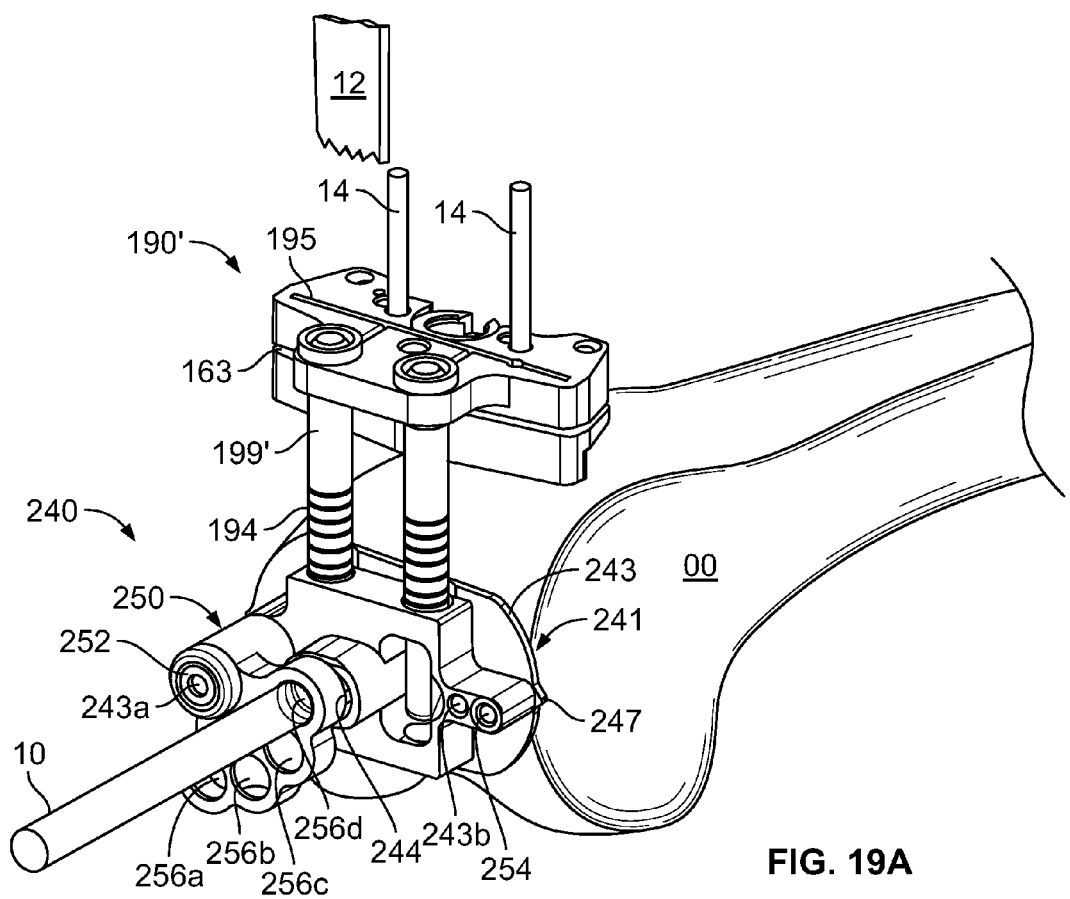
FIGS. 19A and 19B illustrate a distal resection assembly according to further embodiment of the present disclosure and method of using the same.
Figure 19B:
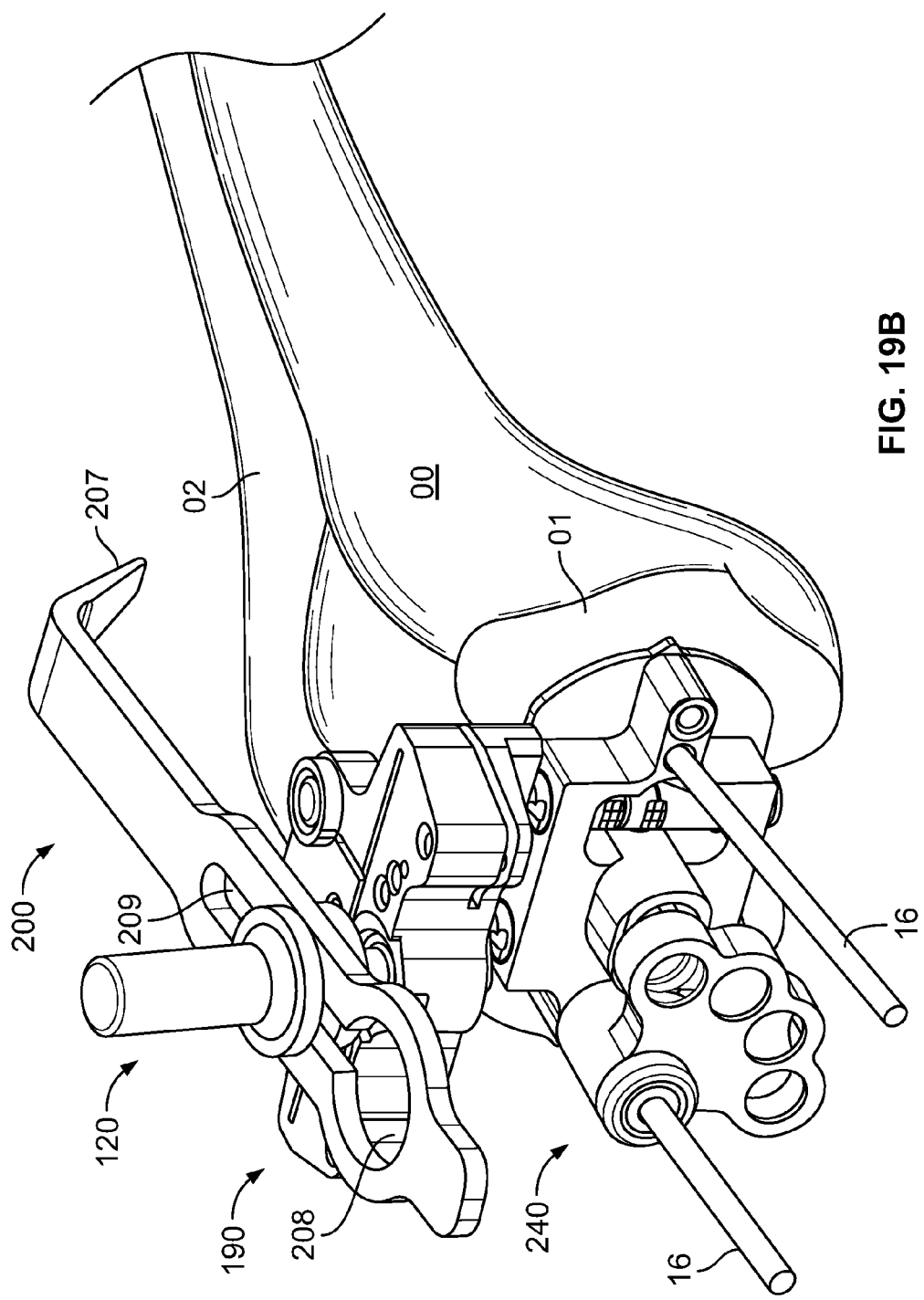

FIGS. 19A and 19B depict an alternative distal resection assembly, which can be used to perform a distal resection of femur 00 and can also be used to size a femoral prosthesis. In the embodiment depicted, the distal resection assembly includes distal referencing guide 240, multicut guide 190', connection bolt 120 and resection stylus 200.

Multicut guide 190' is similar to multicut guide 190 with the difference being that multicut guide 190' includes indicia 194 on elongate members 199' for sizing a femoral prosthesis. In addition, connection bolt 120 and skim cut stylus 200 are identical to that previously described.

Distal referencing guide 240 is similar to referencing guides 30 and 170. However, distal referencing guide 240 includes a marking (not shown) for correspondence with indicia 194 on elongate members 199' and includes two guide openings 243a and 243b. First guide opening 243a extends through the extension 252 extending from body 241 and may be coaxially aligned with the rotation axis of the alignment guide 250. The spacing of guide openings 243a and 243b substantially corresponds to that of all the other guide openings described herein.

A method of using this alternative distal resection assembly is also illustrated by FIGS. 19A and 19B in accordance with a posterior referencing technique/philosophy.

In the method, distal resected surface 01 is formed at the distal end of femur 00 as previously described. As such, distal referencing guide 240 is connected to IM rod 10 via toggle-hole 244 and a selected alignment hole 256a-d based on a predetermined varus-valgus angle. Multicut guide 190' is attached to referencing guide 240 such that distal resection slot 195 is positioned proximal to a distal extent of femur 00. Multicut guide 190' is pined, IM rod 10 is removed from femur 00 and saw blade 12 resects the distal femur through distal resection slot 195 (best shown in FIG. 19A).

Once distal resected surface 01 is formed, A/P guide 60 is used to contact the distal resected surface and posterior condyles to establish the desired I/E orientation. Reference pins 16 are inserted through guide holes 65 and A/P guide 60 is removed, as previously described. Thereafter, distal referencing guide 240 is placed over reference pins 16 via pinholes 243a-b. Multicut guide 190' is attached to referencing guide 240 in the first orientation (described above). The height of multicut guide 190' is adjusted until tip 207 of the resection stylus 200 contacts anterior cortex 02 of the femur 00. A size of a femoral prosthesis can be determined by the alignment of indicia 194 on elongate members 199' of multicut guide 190' and markings of referencing guide 240.

Once the size of a femoral prosthesis is determined, the distal resection assembly is removed leaving referencing pins 16 in place. A/P guide 80 is adjusted to the femoral prosthesis size as previously determined and is attached to reference pins 16. Anterior and posterior resections are performed through posterior and anterior resection slots 98, 102, respectively. Thereafter, chamfer resection block 130 is attached to reference pins 16 and chamfer resections are performed using chamfer block 130 also as described above.

Figure 20A:
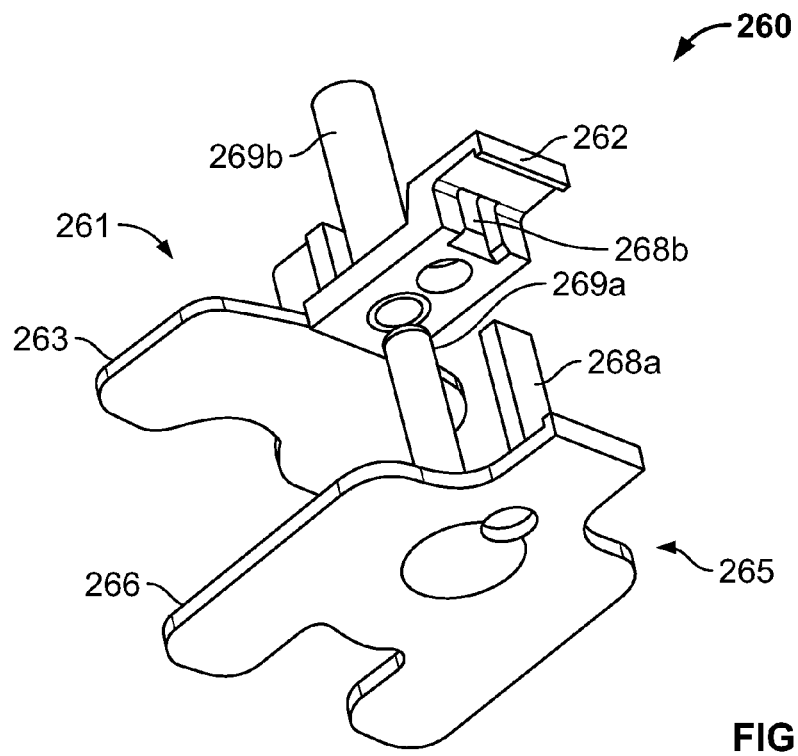
FIGS. 20A-20D illustrate the A/P cutting/sizing guide of FIG. 4A including a gap balance assembly according to an embodiment of the present disclosure and a method of using same.
Figure 20B:
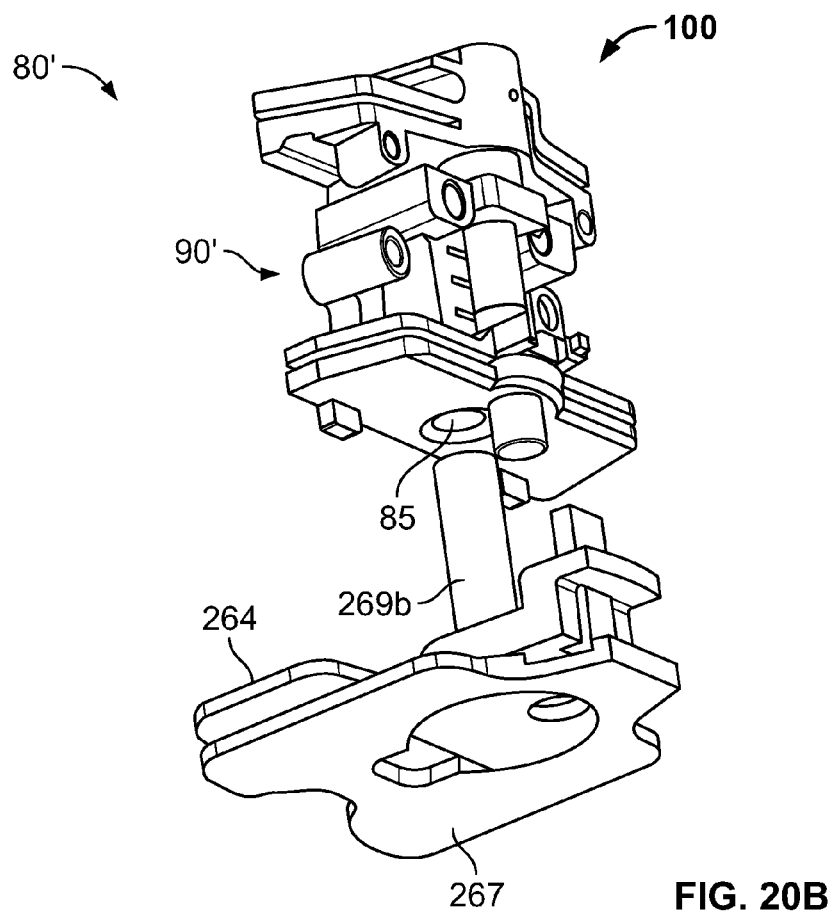

FIGS. 20A and 20B depict a gap balancing device 260 that can be coupled to A/P guide 80' to form a gap balancing assembly. Such device 260 can be provided in the set of devices depicted in FIGS. 2A-5B or in FIGS. 5A-5B, 12A-13, and 18, which provides such sets with a gap balancing functionality without the need for a whole other set of multiple devices.

Gap balancing device 260 generally includes a femoral member 261 and a tibial member 265. Femoral member 261 includes a femoral contact plate 263 and a post connector 262. Femoral contact plate 263 includes a planar reference surface 264 that is sized to extend between two posterior condyles. Post connector 262 is rotatably connected to and extends from femoral contact plate 263 such that contact plate 263 can rotate about a pivot axis. Post connector 262 is generally z-shaped and includes a cannulated post 269b extending therefrom in a direction substantially transverse to the pivot axis. Post connector 262 also includes an opening 268b extending therethrough for receipt of an indicator member 268a (described below).

Tibial member 265 includes a tibial contact plate 266, an indicator member 268a and a post 269a. Indicator member 268a and post 269a each extend from tibial contact plate 266. Tibial contact plate 266 includes a planar bone contact surface 267 for contacting a proximal resected surface 06 of tibia 05. Indicator member 268a is generally rectangular and includes indicia for determining a flexion gap setting. Post 269a is offset from indicator member 268a in a posterior direction and is sized to slidingly engage an opening within cannulated post 269b. The combination of post 269a and indicator member 268a prevents rotation of tibial member 265 relative to femoral member 263.

In the gap balancing assembly (best shown in FIG. 20B), A/P guide 80' includes a modified second body 90', which includes an opening 85 at a bottom end thereof for receipt of cannulated post 269b. Second body 90' of A/P guide 80' is slid over post connector 262 until second body 90' rests on post connector 262. Post 269a extends into cannulated post 269b, and indicator member 268a extends through opening 268b. Markings or an indicator tool on second body 90' align with indicia on indicator member 268a to indicate a femoral component size.

Femoral contact plate 264 extends beyond bone contact surfaces 92 and 109 of A/P guide 80 in a posterior direction for referencing posterior condyles. A resection guide surface defining posterior resection slot 98 is substantially parallel to contact surface 264 of femoral contact plate 263.

Figure 20C:
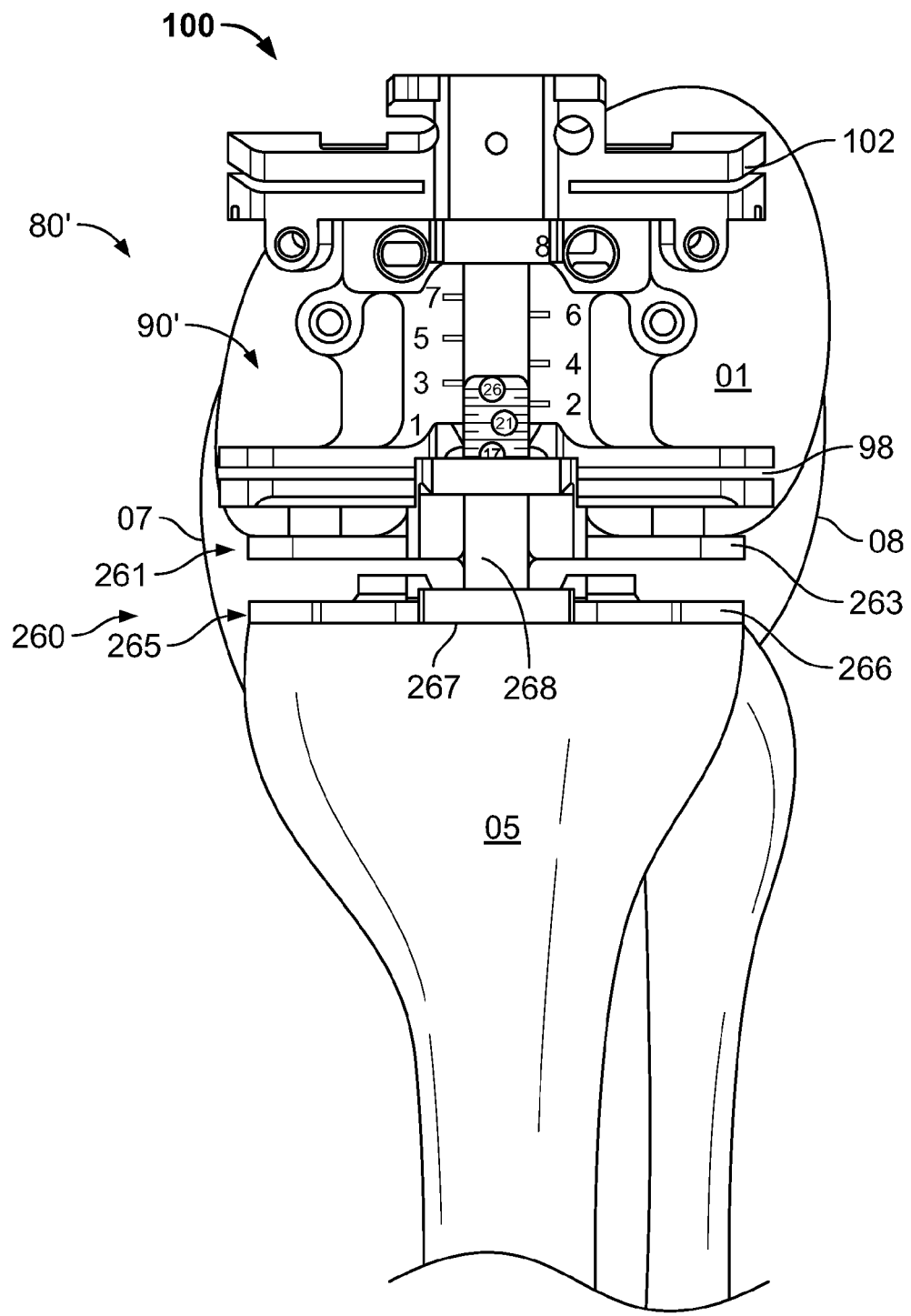
Figure 20D:
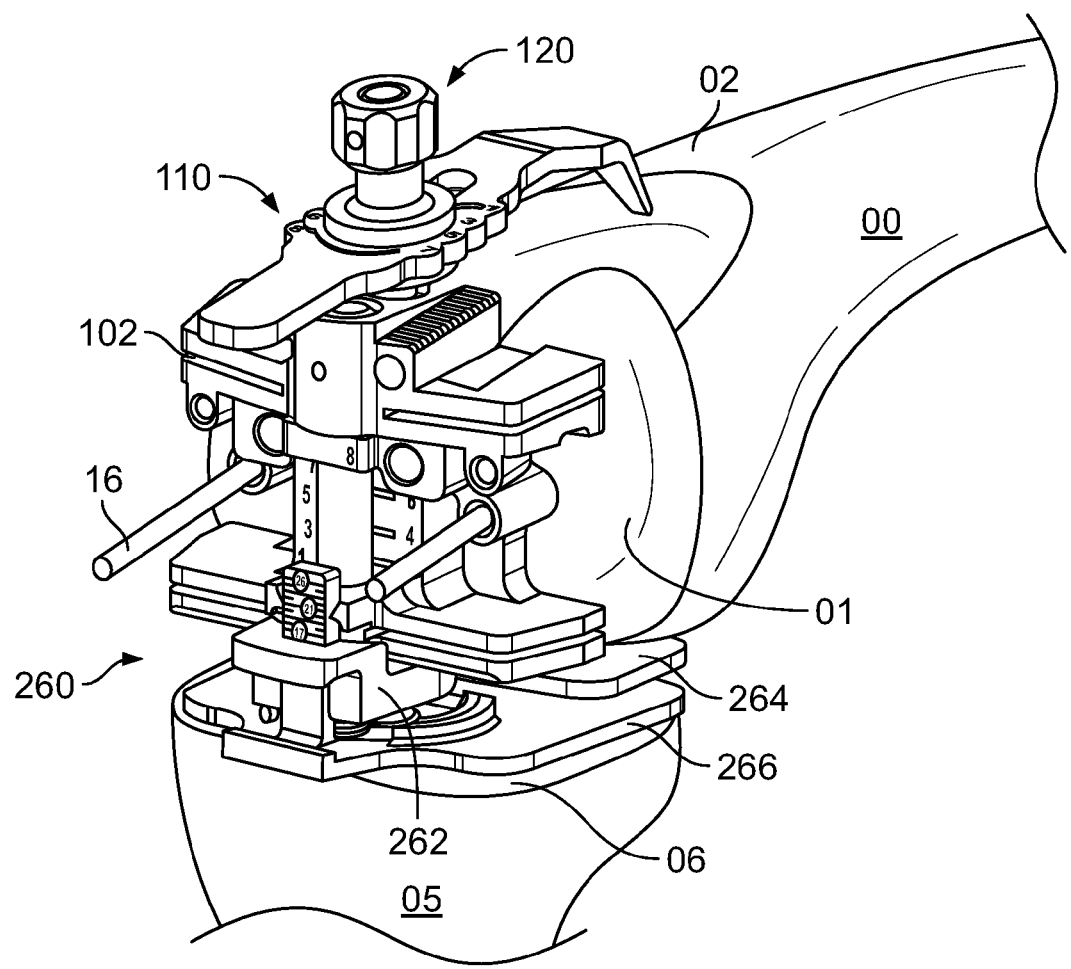

FIGS. 20C and 20D partially illustrate a method of forming bone in accordance with a gap balancing technique using the gap balancing assembly. In such a method, a proximal tibia is resected to form a proximal resected surface 06. Such surface 06 may be perpendicularly aligned with an MA axis of the tibia.

Thereafter, or even before performing the proximal tibial resection, the distal femur is resected using any of the distal resection assemblies as described above. Femur 00 and tibia 05 are then distracted using a tensioner (not shown) or some other device. The extension gap between the distal resected surface 01 of femur 00 and proximal resected surface 06 of tibia 05 is measured.

Tibia 05 is then rotated to about 90 degrees of flexion. Tibial contact plate 266 of gap balancing device 260 is placed flush with proximal resected surface 06. The posterior condyles of femur 00 are placed on femoral reference plate 263 such that both of the posterior condyles are in contact with surface 264. Using the same tensioner (or other device), upper plate portion 261 and lower plate portion 265 are distracted until the markings of post connector 262 and indicia of post 268 indicate a flexion gap measurement substantially the same as the previously measured extension gap. Releases of the collateral ligaments 07 may be performed as needed to adjust the I/E rotation of femur 00 and to balance collateral ligament tension. Such releases are performed until the femoral contact plate 263 is rotated about its pivot axis into parallel alignment with tibial contact plate 266. This indicates parallel alignment between proximal resected surface 06 and the posterior femoral condyles.

A/P guide 80' may be placed on the post connector before or after measuring the flexion gap, although it is preferable for them to be fully assembled first. At this point, posterior resection slot 98 is substantially parallel to proximal resected surface 06 of tibia 05 (best shown in FIG. 20A). Reference pins 16 are inserted through guide openings 95 of A/P guide 80' to set A/P guide 80' in place and for use by chamfer block 130.

Connection bolt 120 and resection stylus 110 are connected to first body 100 (best shown in FIG. 20D). First body 100 is adjusted in an anteroposterior direction until stylus tip 127 contacts the femoral anterior cortex 02. A femoral prosthesis size is determined, and retaining screws 88 are inserted through retaining openings 97 and 108 to fix first body 100 in position relative to second body 90'. Thereafter, connection bolt 120 and/or stylus 110 are removed. Saw blade 12 is inserted through posterior and anterior resection slots 98, 102 to remove bone and form anterior and posterior resected surfaces. Thereafter, chamfer resection block 130 is attached to reference pins 16 and chamfer resected surfaces are formed as described above.

Thus, as described above, when combined with gap balancing device 260, the set of instruments of FIGS. 2A-5B can perform an MA/AA alignment, posterior referencing technique/philosophy, and a measured resection/gap balancing technique/philosophy (or combination thereof). In addition, when combined with gap balancing device 260, the set of instruments of FIGS. 5A-5B, 12A-13, and 18 can perform an MA/AA alignment, anterior/posterior referencing technique/philosophy, and a measured resection/gap balancing technique (or combination thereof). Therefore, as described, such sets of devices can significantly reduce the number of instruments utilized in a TKA procedure and can be provided to a larger segment of surgeons that subscribe to differing techniques/philosophies of bone formation than with current devices.

Figure 21A:
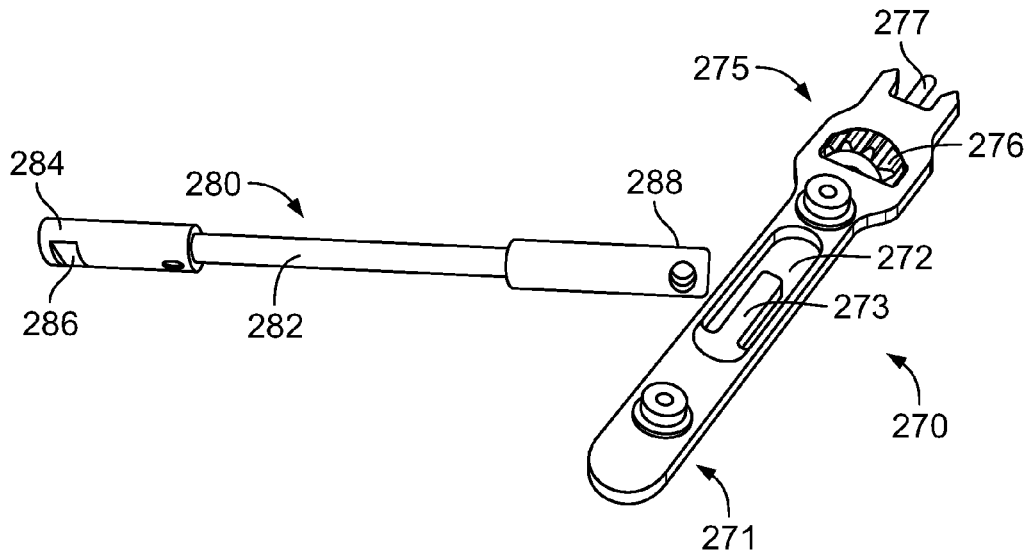
FIG. 21A is a perspective view of a multipurpose handle and elongate instrument according to an embodiment of the present disclosure.
Figure 21B:
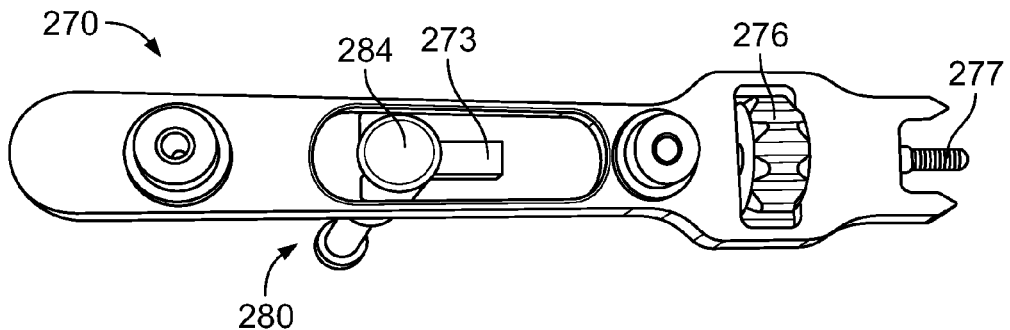
FIG. 21B is a perspective view of the multipurpose handle and elongate instrument of FIG. 21A in an assembled configuration.
Figure 21C:
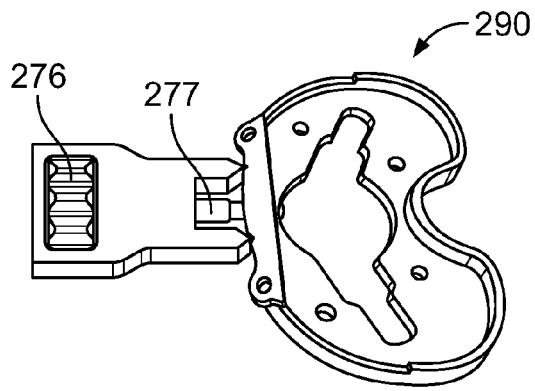
FIG. 21C is a partial view of the multipurpose handle of FIG. 21A connected to a tibial baseplate.

In addition to the devices described above, other instruments utilized in a TKA procedure may be provided with multiple functionalities to help reduce the total number of devices needed for a surgical procedure. FIGS. 21A-21C illustrate such a device, namely a multipurpose handle 270. Handle 270 may be used to manipulate a tibial baseplate template, such as template 290 illustrated in FIG. 21C. Such tibial baseplate template 290 can be used to guide a keel punch and help size for a tibial baseplate prosthesis. Handle 270 can also be used as a T-handle for applying a torque to a device attachable thereto, such as an IM reamer or an adaptor for an IM reamer and other instruments, such as the adaptor 280.

Handle 270 generally includes an elongate member 271 and a head member 275 connected to one end of elongate member 271. Head member 275 includes a threaded extension 277 extending from head member 275. Threaded extension 277 is connected to a thumbwheel 276 disposed within head member 275. Thumbwheel 275 is configured to rotate threaded extension 277 upon tactile manipulation thereof for connection to template 290.

Elongate member 271 includes a channel 272 extending therethrough in a direction transverse to a longitudinal axis thereof. An extension 273 extends into channel 272 in substantially the same direction as the longitudinal axis. Extension 273 preferably has a quadrilateral geometry or some other non-circular geometry. However, a circular geometry can be utilized, but is not preferable. Such extension 273 is receivable in a correspondingly shaped opening in adaptor 280.

Adaptor 280 includes an elongate shaft 282 having a working end 288 disposed at one end of shaft 282 and a connection end 284 at another end of shaft 282. Connection end 284 includes a through-hole 286 configured to receive extension 273 of handle 271. Working end 288 is adapted to couple to multiple instruments, including an IM reamer and/or IM rod, for example.

In a method of using handle 270, extension 273 may be inserted into opening 286 within adaptor 280. Adaptor 280 may be coupled to an IM reamer. Alternatively, handle 270 can couple directly to an opening in an IM rod or IM reamer. The reamer may be placed adjacent a proximal tibia or distal femur and rotated by applying torque to the IM reamer via handle 270 to ream a hole in the bone. Handle 270 can be disconnected from adaptor 280 by removing extension 273 from opening 286, as needed.

Within the same TKA procedure, threaded extension 277 may be inserted into an opening in tibial baseplate template 290. Thumbwheel 276 may then be rotated in a first direction to threadedly connect head member 275 of handle 270 to template 290. While holding elongate member 271, baseplate template 290 can be placed over a resected proximal tibia to assess for size, and a keel punch can be inserted through the template and impacted to form a void within the bone. Template 290 can then be removed from the proximal tibia via handle 270 and disconnected from handle 270 by rotating thumb wheel 276 in a second direction.

Figure 23A:
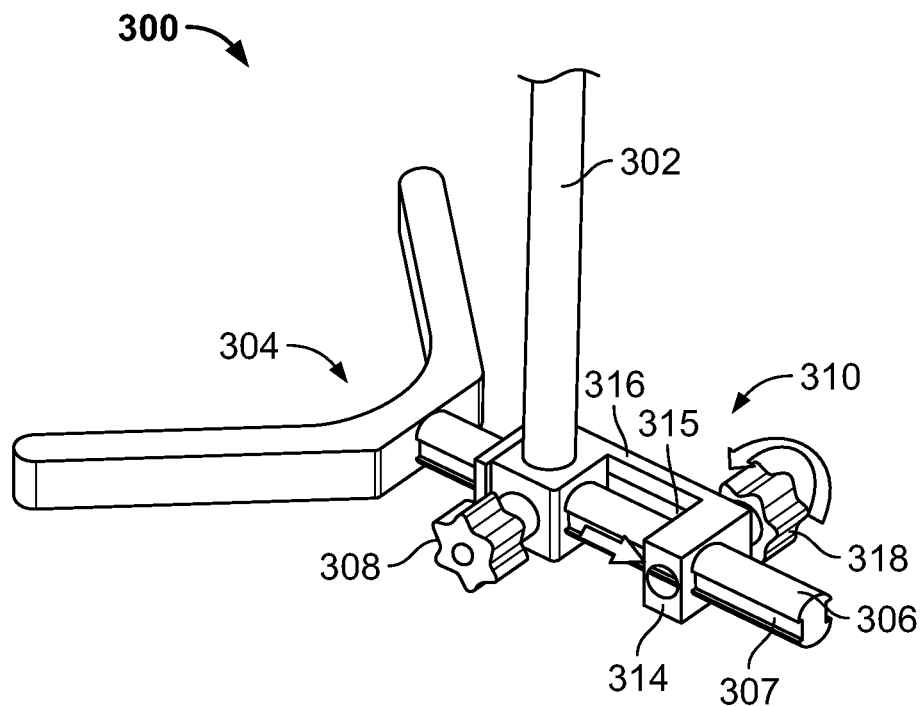
FIG. 23A is a partial perspective view of a tibial resection guide according to the present disclosure including an elongate shaft in a first condition.
Figure 23B:
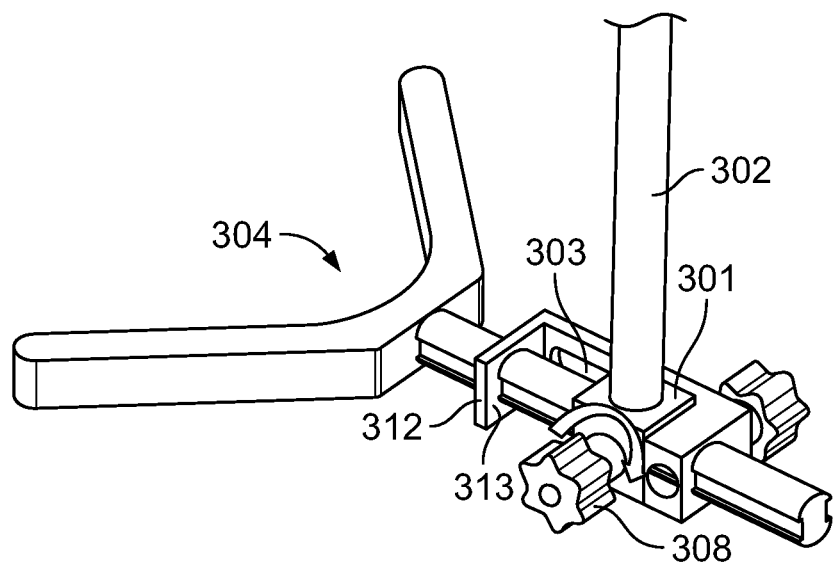
FIG. 23B is a partial perspective view of the tibial resection guide of FIG. 23A with the elongate shaft in a second condition.

In addition to the femoral instruments described above, an improved tibial resection guide 300 is depicted in FIGS. 23A and 23B. Resection guide 300 is improved to help provide a posterior slope to a proximal tibial resection with precision without the need for complex mechanisms or multiple cutting blocks.

In order to provide sagittal plane adjustment (i.e., posterior slope) to a tibial resection, current tibial resection guides use multiple cutting blocks, each with a different sloped guide surface, or complex mechanisms such as adjustment bushings or angular gauges that adjust the slope angle of the guide's cutting surface relative to the tibia.

Figure 22B:
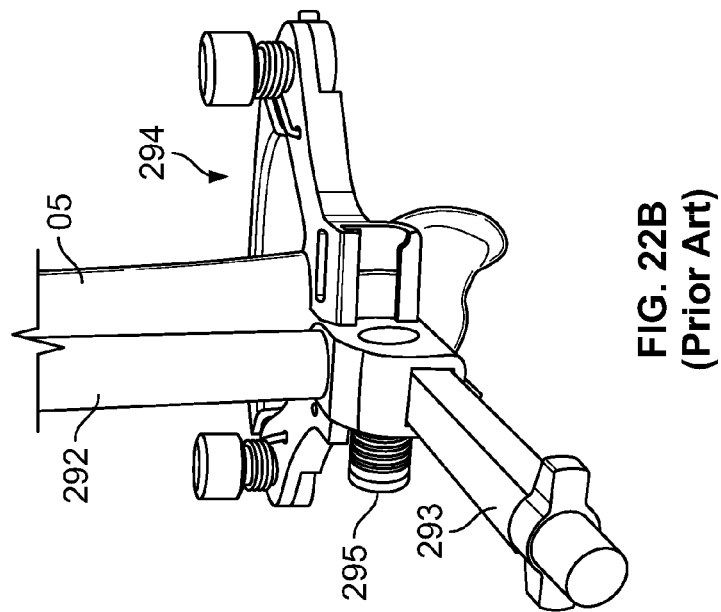
FIG. 22B is a partial perspective view of the tibial resection guide of FIG. 22A.
Figure 22A:
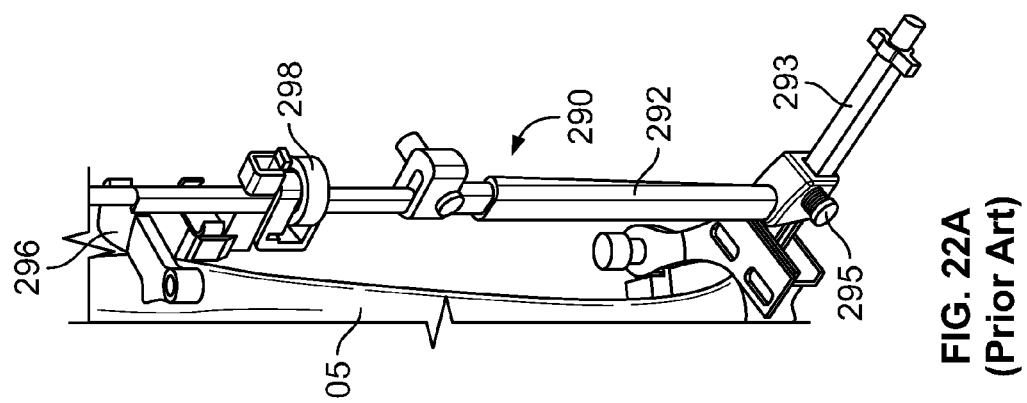
FIG. 22A is a perspective view of a tibial resection guide according to the prior art.

FIGS. 22A and 22B illustrate a prior art extramedullary tibial resection guide 290 that includes an adjustment bushing 298, ankle clamp 294, resection block 296, and elongate shaft 292. Resection block 296 is attached to adjustment bushing 298, which can adjust the proximal-distal location of adjustment block 296 via thumbwheel mechanism 298. Adjustment bushing 298 is attached to elongate shaft 292. Elongate shaft 292 is slidably attached to an elongate member 293 of ankle clamp 294 to provide further slope adjustments. In use, the pitch of resection block 296 is altered by depressing a spring locking mechanism 295 and sliding the distal end of elongate shaft 292 along elongate member 293. However, the slope provided by this adjustment is not measured by device 290 and is difficult to determine how much slope is being added.

FIGS. 23A and 23B illustrate a distal end of the improved tibial resection guide 300. Tibial resection guide 300 includes a resection block (not shown), elongate shaft 302, ankle clamp 304, and a guide block or C-block 310. Resection block (not shown) is similar to resection block 296 and includes a cutting guide surface, which may partially define a cutting guide slot. Ankle clamp 304 includes an elongate member 306 extending therefrom, which includes opposing grooves 307 extend along its length.

Elongate shaft 302 includes a connection portion 301 disposed at a distal end thereof. Connection portion 301 is cube-shaped and has an opening extending therethrough with a similar shape to that of a cross-sectional shape of elongate member 306 of ankle clamp 304. A locking mechanism 308, such as a retaining screw, is connected to connection portion 301.

C-block 310 includes first and second members 312, 314 connected by an intermediate member 316 to form a generally C-shaped structure. First member 312 includes a first abutment surface 313, and second member 314 includes a second abutment surface 315. First and second abutment surfaces 313, 315 face each other and are spaced apart a predetermined distance. Openings extend through first and second members 312, 314 and have a similar shape to that of the cross-sectional shape of elongate member 306. A locking mechanism 318, such as a retaining screw, is a connected to C-block 310. Indicia may be disposed along intermediate member 316 for correspondence to a marking on connection portion 301 to indicate a posterior slope angle.

As assembled, the resection block is connected to a proximal end of elongate shaft 302. Elongate member 306 of ankle clamp 304 extends through the openings of the C-block and connection portion of elongate shaft 306 such that the C-block 310 and connection portion 301 are slidable thereon. Opposing grooves 307 help prevent C-clamp 310 and connection portion 301 from being rotated relative to elongate member 306. Connection portion 301 is disposed between first and second members 312, 314 of C-clamp 310. The predetermined distance between abutment surfaces 313, 315 is such that abutting abutment surface 313 of first member 312 with the connection member 301 positions the resection guide surface at a first angle relative to a tibia, and abutting abutment surface 315 of the second member 314 with the connection member positions the resection guide surface at a second angle with respect to the tibia. The difference between the first and second angles is about 2 to 4 degrees and preferably about 3 degrees. However, the difference between these angles can be about 1 to 6 degrees.

In a method of use, ankle clamp 304 is clamped to a patient's ankle and the tibial resection block is placed adjacent to the proximal tibia such that elongate shaft 302 is positioned in alignment with a tibia. Connection portion 301 of elongate shaft 302 is slid along elongate member 306 of ankle clamp 304 until the resection guide surface of the resection block is oriented at a neutral or zero degree posterior slope relative to the tibia. Locking mechanism 308 is then engaged to elongate member 306.

C-block 310 is then slid along elongate member 306 until first abutment surface 313 of first member 312 abuts connection portion 301 of elongate shaft 302. C-block 310 is then locked into position by rotating locking mechanism 318 to engage elongate member 306. Thus, connection portion 301 abuts first abutment surface 313 at a zero degree posterior slope. Where a posterior slope greater than zero degrees is desired, connection portion is unlocked by rotating locking mechanism 308 and then connection portion 301 is slid along elongate member 306, while maintaining the resection block adjacent to the tibia, until connection member 301 abuts second abutment surface 315, which pitches the resection block to the desired posterior slope. The tibia is then resected with a saw along the resection guide surface of the resection block. In this regard, the posterior slope of the proximal resected surface may be about 2 to 4 degrees.

In some embodiments, connection portion 301 may be stopped at incremental locations between first and second abutment surfaces 313, 315 to achieve different angles of posterior slope. A marking on connection portion 301 may align with indicia on intermediate member 316 to indicate which angle is achieved. In other embodiments, modular spacers (not shown) may be provided, which can connect to second abutment surface 315 so that abutting the spacer with connection portion 301 of elongate shaft 302 achieves a different posterior slope angle. In even further embodiments, a plurality of C-blocks may be provided that each have different distances between first and second abutment surfaces 313, 315 for achieving different angles of posterior slope.

The devices described herein can be provided in device/instrument sets for performing TKA where such devices achieved multiple functionalities that would otherwise be achieved with a greater number of conventional instruments. Individually and in the aggregate, this can lead to significant cost reductions for manufacturers, hospitals and patients alike.

Figure 24A:
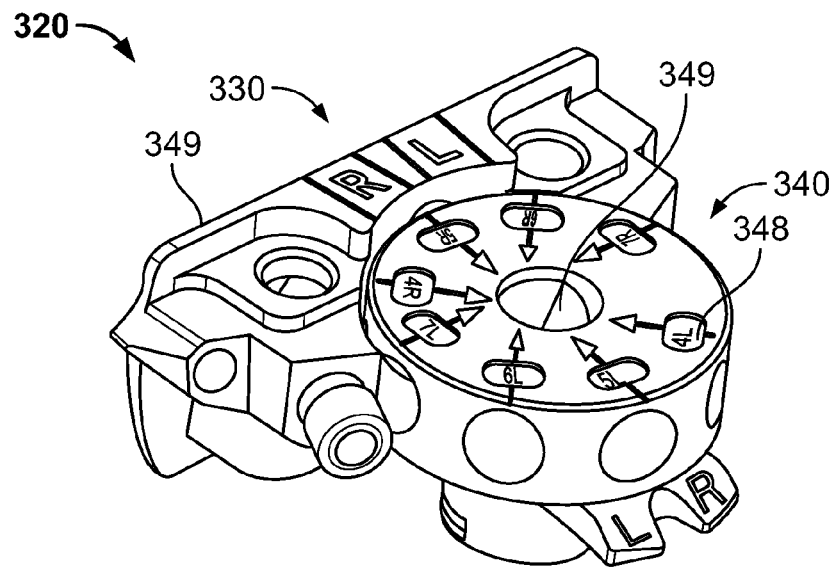
FIG. 24A is a perspective view of a distal referencing guide according to another embodiment of the present disclosure.
Figure 24B:
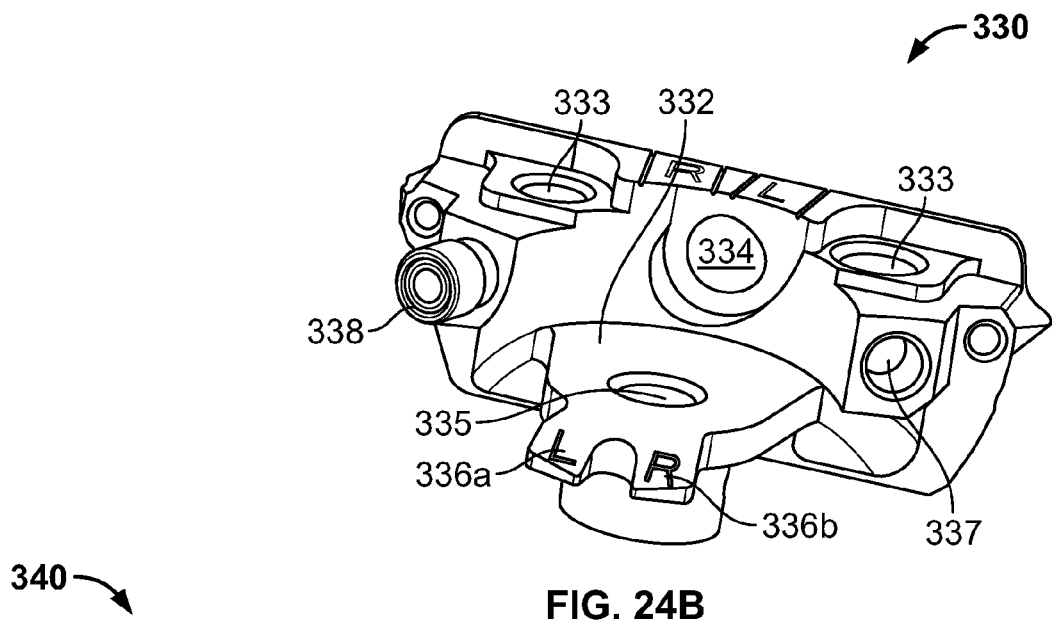
FIGS. 24B and 24C are perspective views of a referencing member and wheel component of the distal referencing guide of FIG. 24A.
Figure 24C:
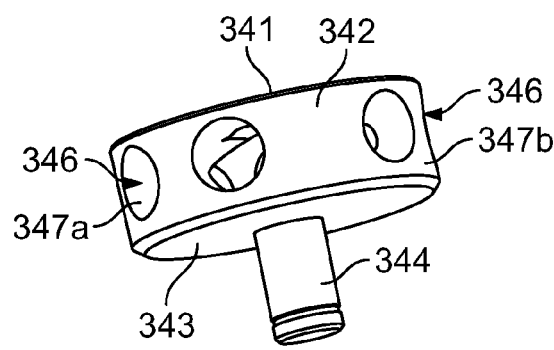

The following description includes various alternative embodiments of some of the devices described above. FIGS. 24A-24C depict a distal referencing guide 320 according to another embodiment. Referencing guide 320 is similar to referencing guides 30, 170, and 240. Referencing guide 320 has a low profile that is particularly useful for an anterior referencing technique using multicut guide 190, as previously described. However, referencing guide 320, much like guide 170, can also be used for a posterior referencing technique and is also adapted for use with distal cutting guide 50.

Distal referencing guide 320 generally includes a referencing member 330 and a wheel component 340. Referencing member 330 is similar to bodies 21, 171, and 241 in that referencing member 330 includes utility openings 333, a toggle-hole 334 forming a rim, and a bone contact surface 339 for contacting a distal resected surface of a femur. Referencing member 330 also includes retaining openings 337 intersecting with utility openings 333. Set screws 338 are disposed within retaining openings 337 and are adjustable to retain a resection guide coupled to referencing member 330.

Unlike bodies 21, 171, and 241, referencing guide 320 does not include an ovular boss or ovular opening. Instead, referencing guide 330 includes a semi-circular recessed region intersecting with toggle hole 334. This semi-circular recessed region forms a wheel-component platform 332 having an opening 335 extending therein.

Wheel component or alignment member 340 generally includes a cylindrical body 342 and a cylindrical extension 344. Cylindrical extension 344 extends from and is concentric with body 342. Extension 344 is sized to be received by opening 335 of wheel-component platform 332 and is rotatable therein. This provides for a reliable and easy to sterilize structure.

Cylindrical body 340 is sized to be received in the semi-circular recess of referencing member 330. Body 342 includes a top surface 341 and bottom surface 343 defining a sidewall 342 therebetween. A plurality of alignment-holes 346 spaced at intervals about a circumference thereof, extend through sidewall 342 and through the entirety of body 342. Each hole 346 has a diameter slightly larger than an IM rod and forms two openings 347a-b in sidewall 342, which are disposed at opposite sides of wheel component 340. Thus each alignment-hole 346 has two openings 347a-b associated with it. An axis of each hole 346 is offset from a central axis of wheel component 340. An offset distance of each hole 346 is based on a particular varus-valgus angle associated with the particular hole 346. An axial opening 349 extends through top surface 341 of wheel component 340, is concentric with the central axis of the wheel component 340, and intersects at least some of alignment-holes 346. This opening 349 facilitates sterilization.

Indicia 348 are located on top surface 341 and align with each opening 347 to indicate a particular varus-valgus angle and a particular leg. In addition, referencing member 330 includes indicia 336a-b adjacent to wheel component 340, such that when selected indicia 348 of wheel component 340 is aligned with indicia 336a or 336b of referencing member 330, an alignment-hole 346 associated with selected indicia 348 is aligned with toggle-hole 334.

For example, where a 5 degree varus-valgus angle for a left leg is desired, indicia 348 on wheel component 340 indicating 5 degree left leg is aligned with indicia 336a on the referencing member indicating left leg. A first opening 347a associated with this indicia 348 faces the operator. Conversely, where a 5 degree varus-valgus angle for a right leg is desired, wheel component 340 is rotated less than 180 degrees such that indicia 348 of the wheel component indicating 5 degree varus-valgus and right leg is aligned with indicia 336b on referencing member 330 indicating right leg. A second opening 347b associated with this indicia 348 faces the operator. It is noted that in this example, a different opening 347a or 347b, but the same hole 346, is aligned with indicia 336a or 336b of referencing member 330 in order to achieve the same varus-valgus angle for an opposite leg. Thus, for this device 320, openings determine leg and holes determine varus-valgus angle. Thus referencing member is universal to both right and left legs.

In a method of using, a desired varus-valgus angle is determined, as described in greater detail above. Wheel component 340 is rotated until indicia 348 indicating the desired varus-valgus angle is aligned with indicia 336a or 336b on referencing member 330. Referencing member 330 is slid over an IM rod, such as IM rod 10, extending from a femur such that the rod extends through toggle-hole 334 and the selected alignment-hole 346. Due to the two-opening, one-hole characteristics of wheel component 340, once the IM rod is engaged to referencing guide 320, wheel component 340 cannot be rotated, which prevents unintended rotation of wheel component 340 and removes the need for other mechanisms, such as ball detents, to lock wheel component 340 in the desired orientation. Referencing guide 320 is slid along the IM rod until a bone contact surface 339 thereof abuts the distal femur. Cutting block 50, 190, or 190' can then be attached thereto via utility openings 333 for performing a distal resection and/or anterior skim cut.

Figure 25A:
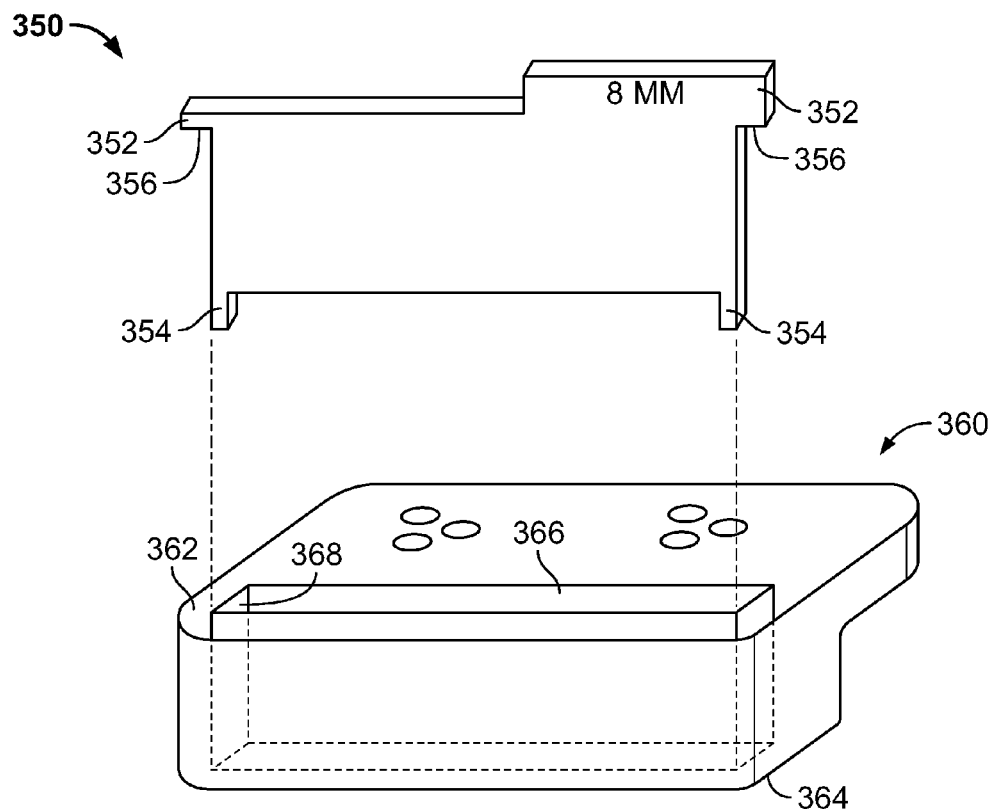
FIG. 25A is an exploded, schematic view of a distal cutting guide that includes shim in a first condition according to another embodiment of the present disclosure.
Figure 25B:
FIG. 25B is a cross-sectional view of the shim in a second condition and disposed within a body of the distal cutting guide of FIG. 25A.

FIGS. 25A and 25B depict a distal cutting guide that includes a floating slot according to another embodiment. As previously described with regard to distal cutting guide 50, a shim can be attached thereto via rails. The depicted embodiment illustrates an alternative attachment mechanism.

As shown, a shim 350 includes laterally-medially extending tabs 352 at one end thereof, which define abutment surfaces 356. Bendable tabs 354 are disposed at another end of shim 350. These bendable tabs 354 are plastically deformable from a first position, as shown in FIG. 25A, to a second position, as shown in FIG. 25B.

Thus, in a method of assembly, shim 350 is placed within a slot 366 of a resection guide body 360. Guide body 360 includes a top surface 362, a bottom surface 364 and a sidewall 368 therebetween Shim 350 is inserted into slot 366 such that abutment surfaces 356 abut top surface 362 and bendable tabs 354 extend from slot 366. Bendable tabs 354 are bent outwardly into the second position so as to form abutment surfaces 358, which can abut bottom surface 364. In this way, shim 350 can be displaced within slot 366 for guiding differing depths of resection.

Figure 26A:
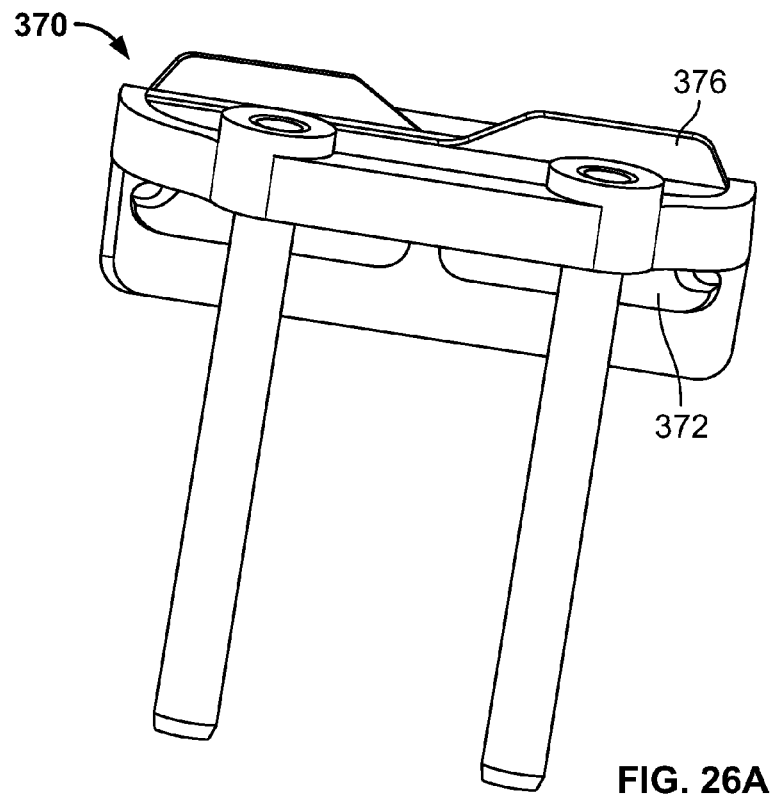
FIG. 26A is a perspective view of a distal cutting guide according to a further embodiment of the present disclosure.
Figure 26B:
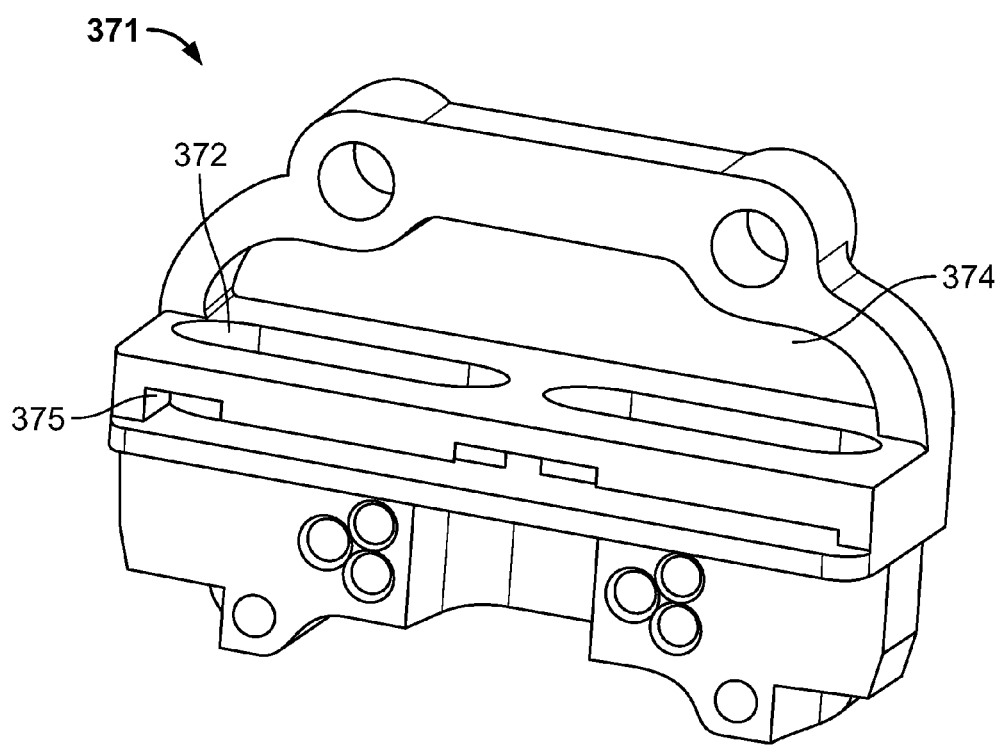
FIG. 26B is a top perspective view of the distal cutting guide of FIG. 26A.

FIG. 26A depict a further embodiment of distal cutting guide 370. This guide 370 includes multiple slots 372, 374 for access to shim 374 in order to facilitate sterilization. For example, as shown, horizontal slots 372 extend through a body 371 of guide 370 and intersect with a guide slot 375. A vertical slot 374 also extends through the body and intersects horizontal slots 372. These slots 372 and 374 provide additional passageways for cleaning solution, gases, and other sterilizing agents.

Figure 27A:
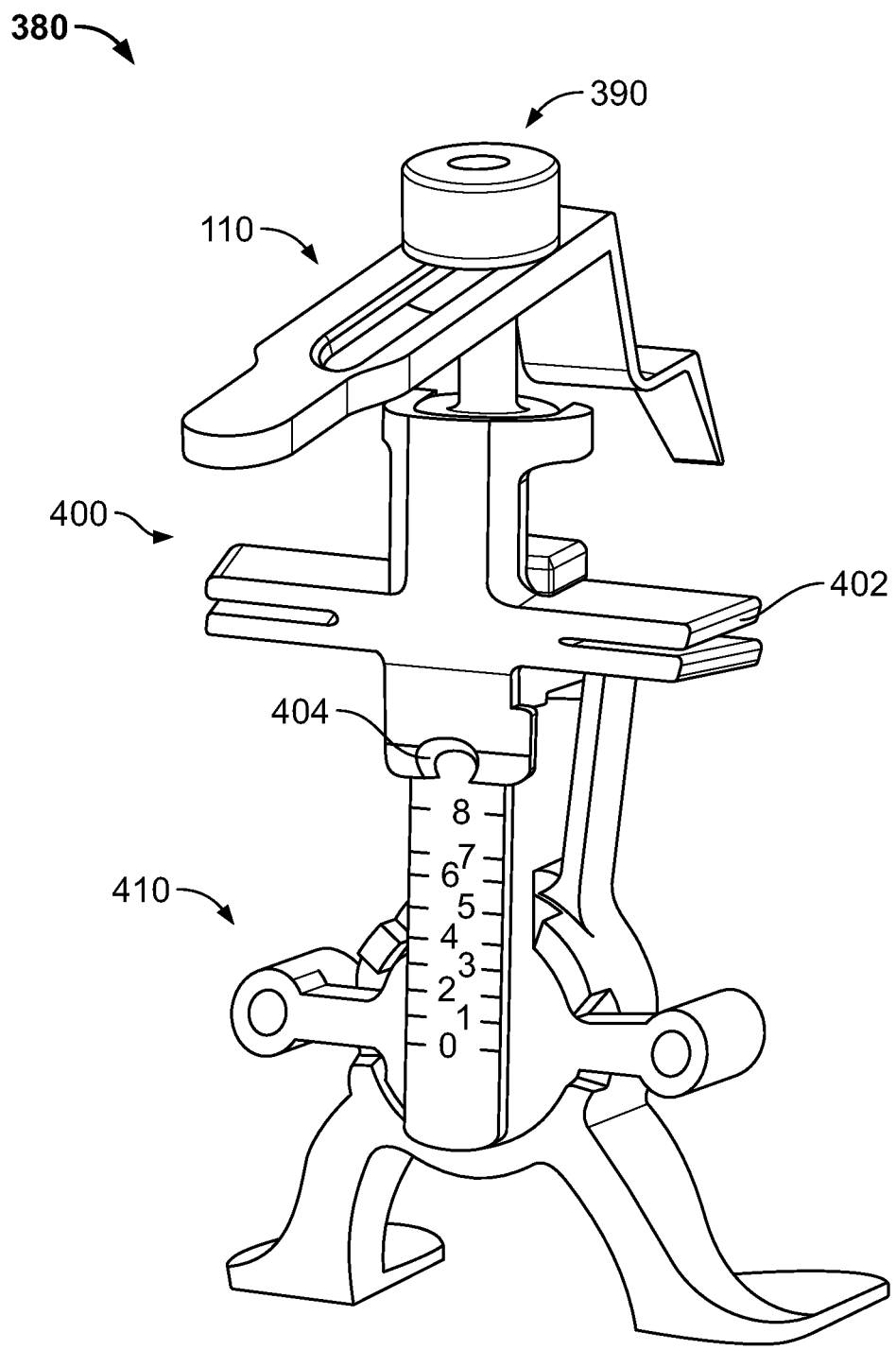
FIG. 27A is a perspective view of an A/P guide according to a further embodiment of the present disclosure.
Figure 27B:
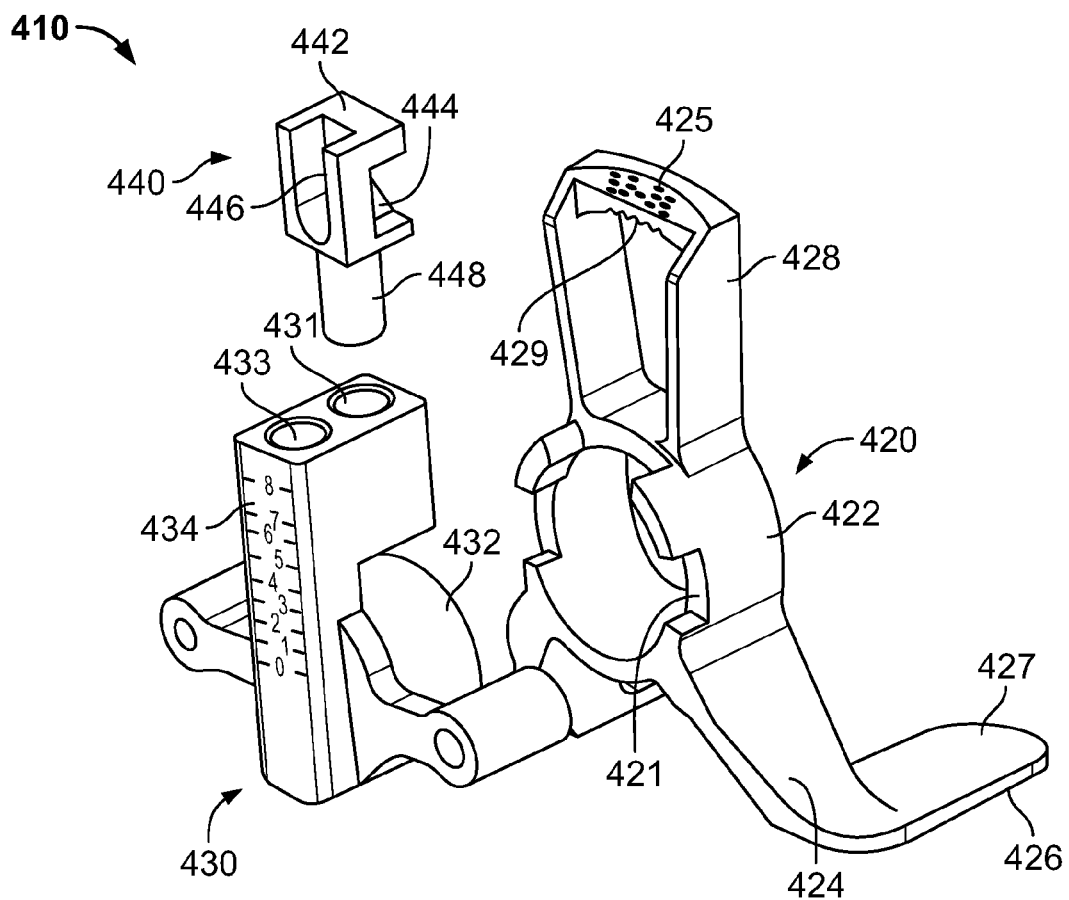
FIG. 27B is an exploded view of a referencing assembly of the A/P guide of FIG. 27A.
Figure 27C:
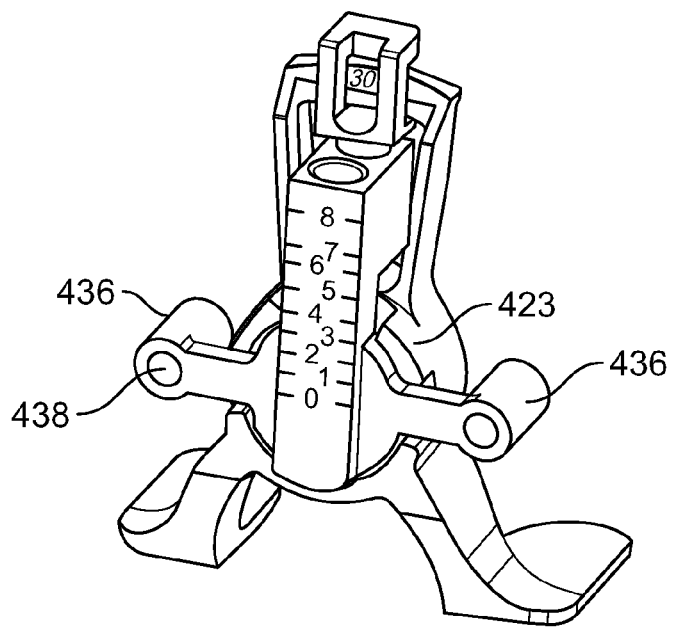
FIG. 27C is an assembled, perspective view of the referencing assembly of FIG. 27A.

FIGS. 27A-27C an A/P guide 380 according to another embodiment. A/P guide 380 is preferably used for posterior referencing and generally includes anterior referencing guide 400, referencing assembly 410, resection stylus 110, and connection bolt 390.

Resection stylus 110 is the same as that previously described, and connection bolt 390 is similar to connection bolt 120. Anterior referencing guide 400 includes a guide slot 402 extending therethrough for guiding a blade runner. Referencing guide 400 also includes markings or an indicator tool 404 for aligning with indicia located on referencing assembly 410 for indicating a femoral component size. Referencing assembly 410 (best shown in FIGS. 27B and 27C) generally includes a reference member 420, toggle member 430, and engagement member 440. Reference member 420 includes an annular body 422, a pair of legs 424 and associated feet 426, and a reference head 428. Legs 424 and reference head 428 are connected to and extend from annular body 422. Feet 426 extend from legs 424 and include planar reference surfaces 427 for contacting posterior condyles. Head 428 includes an aperture for receipt of a portion of toggle member 430 and includes indicia 425 for indicating an angle of I/E rotation. Reference head 428 also includes a plurality of teeth 429 defining notches therebetween. Annular body 422 includes an aperture for receipt of a portion of toggle member 430. Interference members 423 are disposed about the periphery of annular body 422 and define recesses 421 for arms of toggle member 430.

Toggle member 430 includes cylindrical body 432, arms 436, and a toggle head 434. Cylindrical body 432 is receivable within annular body 422 and is rotatable therein. Arms 436 are receivable in recesses 421 and include guide-holes 438 extending therethrough. Toggle head 434 includes a first opening 431 for receipt of a spring and engagement member 440, and a second opening 433 for receipt of connection bolt 390 or a post of anterior referencing guide (not shown).

Engagement member 440 includes an engagement head 442 and a post 448 extending therefrom. Engagement head 442 includes a viewing window 446 for viewing indicia and includes at least one tooth 444 for engaging a notch formed by corresponding teeth 429 of reference head 428.

As assembled (best shown in FIG. 27C), arms 436 extend through recesses 421 and cylindrical body 432 is rotatably disposed within annular body 422 such that arms 436 can toggle between various angles of rotation, such as 0 to 6 degrees of rotation, for example. Interference members 423 provide a rotational limit for arms 436. Post 448 of engagement member 440 is disposed within first opening 431 and is biased into toothed engagement with reference head 428 by a spring.

In a method of using, a desired I/E orientation is determined, as discussed in more detail above. An operator depresses engagement member 440 to disengage engagement member 440 from reference member 420. Toggle member 430 is then rotated to the desired orientation, which is indicated by indicia 425, and engagement member 440 is released into its biased position, thereby locking toggle member 430 into position via toothed engagement.

A/P guide 410 is placed against a distal resected surface and posterior condyles of a femur. Reference pins, such as pins 16, are inserted through guide-holes 438. Anterior referencing guide 400 along with stylus 110 are slidably connected to second opening 433 until stylus 110 contacts an anterior cortex of the femur. A femoral component size is then determined. A secondary check can be performed by inserting a blade runner (not shown) through guide slot 402 to reference the anterior cortex.

Figure 28A:
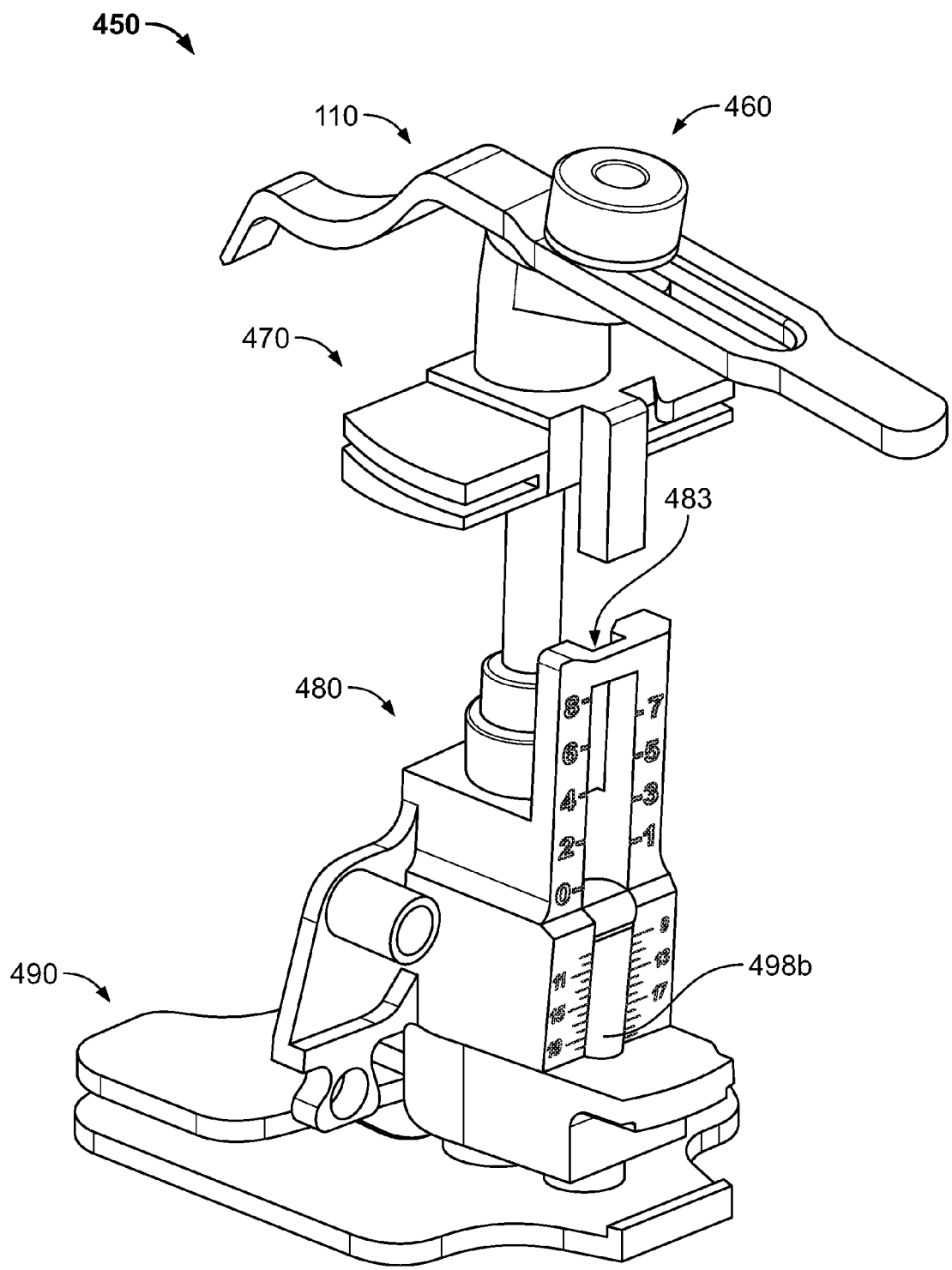
FIG. 28A is a perspective view of a gap balancing assembly according to another embodiment of the present disclosure.
Figure 28B:
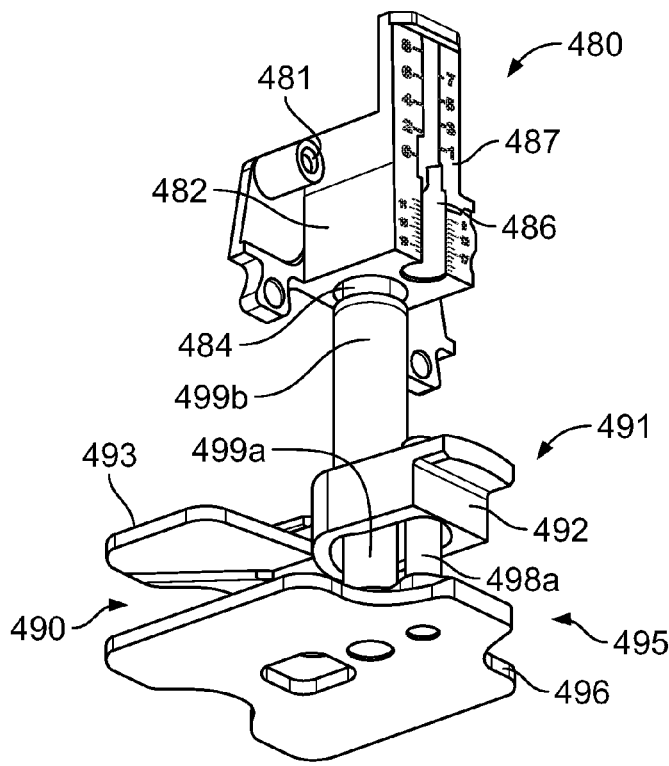
FIG. 28B is a partially exploded view of a gap balancing device and referencing member of the gap balancing assembly of FIG. 28A.
Figure 28C:
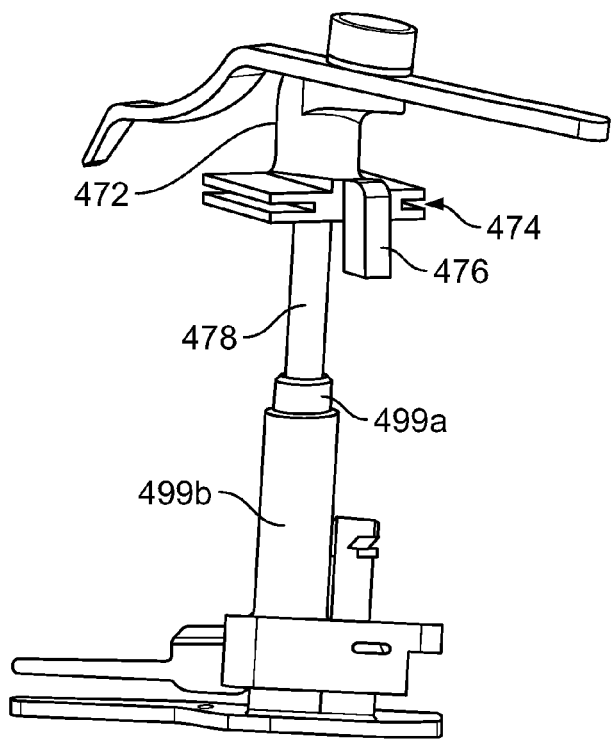
FIG. 28C is a perspective view of the gap balancing device assembled with a resection guide and stylus of FIG. 28A.

FIGS. 28A-28C depict gap balancing assembly 450 according to another embodiment. Gap balancing assembly 450 generally includes an intermediate member 480, gap balancing device 490, reference stylus 110 and connection bolt 460. Reference stylus 110 is the same as that previously described, and connection bolt 460 is similar to connection bolt 120.

Intermediate member includes a body that has a planar bone contact surface for contacting a distal resected surface of a femur. In addition, intermediate member 480 includes a post opening 484 extending through a bottom surface thereof, guide openings 481 for reference pins 16, and a front facing slot 486 for receipt of an indicator member 498a. Indicia 487 are located adjacent front facing slot 486 for indicating collateral ligament tension and femoral component size.

Gap balancing device 490 is similar to gap balancing device 260 in that it includes a femoral member 491 and tibial member 495. Femoral member 491 includes a femoral contact plate 493 rotatably connected to post connector 492. The post connector includes a cannulated post 499b and an opening 498b. In addition, tibial member 495 includes an indicator member 498a and post 499a. However, gap balancing device 490 differs from device 280 in that post 499a is also cannulated for receipt of a post 478 extending from anterior reference guide 470 (described below). Also, indicator member 498a is cylindrical, not rectangular.

Anterior reference guide 470 includes a body 472 with a reference guide slot 474 extending therethrough. A downwardly extending tab 476 extends from body 472 and is receivable within a bone-facing slot 483 of intermediate member 480. A post 478 also extends from body 472 and is receivable within first cannulated post 499a.

As assembled, femoral member 491 is slidably connected to tibial member 495 such that first cannulated post 499a extends into second cannulated post 499b, and the indicator member 498a extends into opening 498b. Intermediate member 480 rests on post connector 492 such that first and second cannulated posts 499a-b extend through post opening 484 and indicator member 498a is slidably disposed in front facing slot 486. Post 478 of anterior reference guide 470 extends into first cannulated post 499a, and downwardly extending tab 476 is disposed within bone-facing slot 483.

Operation of gap balancing assembly 450 is similar to that previously described. As such, tibial contact plate 496 is placed against a proximal resected surface of a tibia and femoral reference plate 493 contacts posterior condyles of a femur. Femoral member 491 and tibial member 495 are distracted with a tensioner until indicia 487 and indicator member 498a indicates a tension substantially similar to an extension gap tension previously determined Collateral ligament releases are performed as needed to obtain parallel alignment of femoral and tibial contact plates 493, 496.

Thereafter, anterior reference guide 470 and stylus 110 are adjusted by sliding post 478 within first cannulated post until stylus 110 contacts an anterior cortex of a femur. A femoral component size is determined by viewing the alignment of downwardly extending tab 476 with adjacent indicia 487. A secondary check can be performed by inserting a blade runner (not shown) through guide slot 402 to reference the anterior cortex.

FIGS. 29A-29D depict a distal referencing guide 500 according to a further embodiment of the present disclosure. Distal referencing guide 500 includes a guide body 502 and a bushing 510. Guide body 502 includes first and second surfaces 505, 506. First surface 505 is a planar bone contact surface and is disposed opposite second surface 506. An elongate slot 507 extends through first and second surfaces 505, 506. Such slot 507 also extends through an edge 509 of body 502 which intersects first and second surfaces 505, 506 at a posterior end of body 502. Opposing rails or sidewalls 501a-b define slot 507 and extend in an anterior-posterior direction. Guide body 502 also includes a resection guide support 508 extending from first surface 505 and is configured to connect to a distal resection guide.

Bushing 510 is generally a solid body of revolution and has a longitudinal opening 515 that extends along its length through first and second ends 514, 516 of bushing 510. Longitudinal opening 515 is sized to receive an intramedullary rod therethrough and defines a longitudinal axis 511. First and second engagement notches 512a-b are disposed on opposite sides of bushing 510 adjacent first end 514 of bushing 510 and are sized to receive respective rails 501a-b of guide body 502. Such notches 512a-b have a generally rectangular shape that each defines a centroid. The centroid of the first engagement notch 512a is positioned closer to first end 514 of bushing 510 than the centroid of second notch 512b. In this regard, a notch axis 513 extending through the centroids of each notch 512a-b is perpendicular to or obliquely angled relative to longitudinal axis 511. The angular relationship between such axes 512a-b corresponds to a varus-valgus angle. For example, notch axis 513 and longitudinal axis 511 may intersect at an angle of about 87 degrees for a 3 degree varus-valgus angle, or 84 degrees for a 6 degrees varus-valgus angle. However, in some embodiments, the axes 511, 513 may be perpendicular to correspond to a 0 degree varus-valgus angle.

Figure 29A:
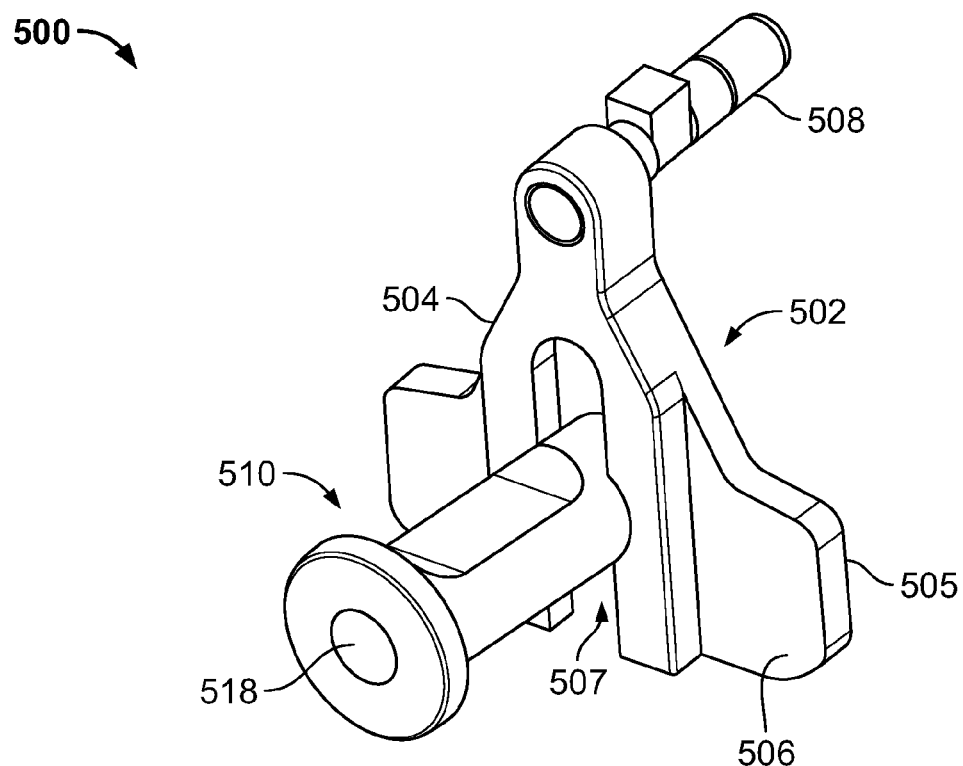
FIG. 29A is a perspective view of a distal referencing guide according to a further embodiment of the present disclosure.
Figure 29B:
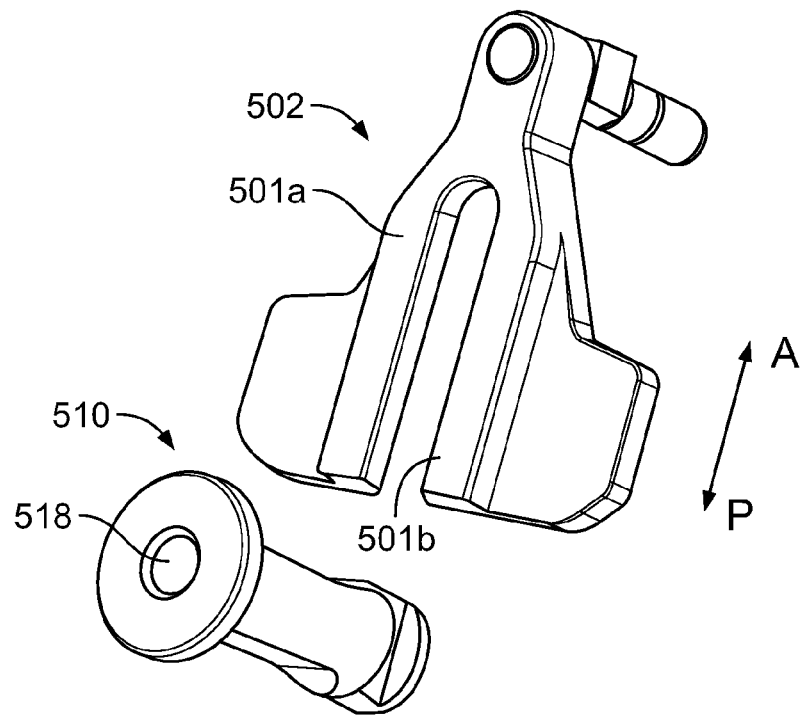
FIG. 29B is an exploded view of the distal referencing guide of FIG. 29A.
Figure 29C:
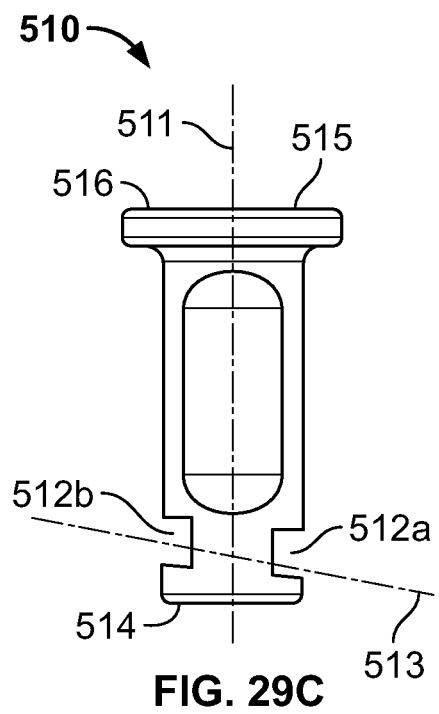
FIG. 29C is a bottom view of a guide bushing of the distal referencing guide of FIG. 29A.
Figure 29D:
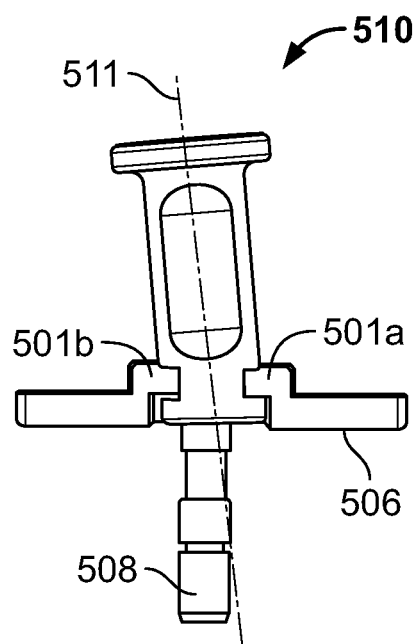
FIG. 29D is a bottom view of the distal referencing guide of FIG. 29A.

As shown in FIGS. 29A and 29D, when bushing 510 is connected to guide body 502, bushing 510 is slidably connected to rails 501a-b such that rails 501a-b are slidably disposed within corresponding engagement notches 512a-b. Rails 501a-b and notches 512a-b may be closely dimensioned so that friction holds bushing 510 in any position within slot 507 while allowing an operator to overcome the friction to reposition bushing 510 within slot 507.

Several bushings 510 that correspond with different varus-valgus angles may be provided in a kit that includes guide body 500. For example, a kit may include a first bushing corresponding to a 0 degree varus-valgus angle, a second bushing corresponding to a 3 degree varus-valgus angle, and a third bushing corresponding to a 6 degree varus-valgus angle.

In a method of using distal referencing guide 500, a distal end of a femur is exposed by an operator. An intramedullary rod is inserted into an intramedullary canal of the femur so that a portion of the intramedullary rod extends from the distal end of the femur. The operator selects a desired varus-valgus angle for the final implanted femoral prosthesis. For example, a varus-valgus angle of 3 degrees may be selected. In such example, the operator then selects a bushing 500 corresponding to a 3 degree varus-valgus angle and connects bushing 500 to guide body 502. In this regard, bushing 510 is engaged to rails 501a-b via notches 512a-b and slid along rails 501a-b to a desired anterior-posterior position. Bushing 510, along with guide body 502, is then positioned over the intramedullary rod so that bone contacting surface 505 of guide body 502 contacts the lateral and medial condyles of the femur. A resection guide (not shown) is connected to the resection guide support 508. The resection guide may then be moved posteriorly to abut an anterior portion of the femur by sliding guide body 502 posteriorly relative to bushing 510 while bushing 510 is coupled to the intramedullary rod. After the distal resection guide is fixed to the bone, such as by bone pins, the intramedullary rod may be removed from the bone and bushing 510 may be disconnected from guide body 502 so that resection of the distal femur can be performed.

Variations of the above described method are contemplated. For example, bushing 510 may be slid over the intramedullary rod without guide body 502. Guide body 502 can then be connected to bushing 510 while bushing 510 is connected to the intramedullary rod by inserting rails 501a-b into notches 512a-b and sliding body 502 in a posterior direction. In another variation, the intramedullary rod can be connected to the intramedullary rod before the intramedullary rod is inserted into the femur.

Figure 30:
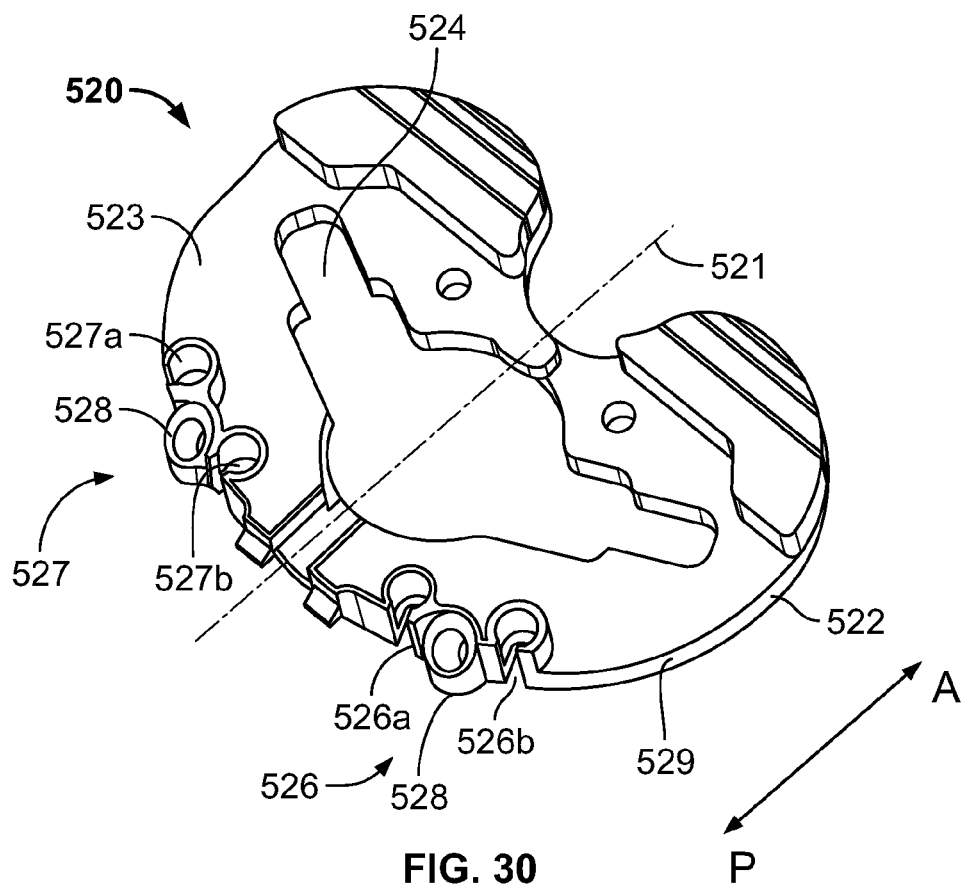
FIG. 30 is a perspective view of a baseplate template according to an embodiment of the present disclosure.

FIG. 30 depicts a baseplate template 520 according to an embodiment of the present disclosure. Baseplate template 520 can be used to help size a tibial baseplate for fixation to a proximal end of a tibia. Baseplate template 520 can also be used to assist in guiding a keel punch into a proximal end of the tibia. In this regard, baseplate template 520 includes a first surface or proximal surface 523 and a second surface or distal surface 529. First and second surfaces 523, 529 intersect an edge 522 that defines a periphery of template 520. The periphery of template 520 is contoured and sized to match a periphery of a resected proximal tibia of a certain size. Thus, template 520 can be provided in multiple different sizes to accommodate a particular patient's anatomy.

Baseplate template 520 has a keel opening 524 that extends through the first and second surfaces 523, 529 and defines the general shape of a keel punch. Template 520 also has two sets of notches 526, 527 that extend into edge 522 of template 520 at a posterior end thereof. Each set 526, 527 includes two notches which are separated by an angled pin sleeve 528. Thus, first set 526 has a first and second notch 526a-b, and second set 527 also has a first and second notch 527a-b. The sets of notches 526, 527, while being disposed at a posterior end of template 520, are disposed at opposite sides of a midline 521 of template 520 which extends in an anterior-posterior, or A-P, direction. Each notch 526a-b, 527a-b is dimensionally larger at an end thereof which is remote from edge 522 so as to be able to receive an engagement head 537a-b of a template alignment handle 530, as described below.

FIGS. 31A-31D depict the template alignment tool 530 which may be used to manipulate baseplate template 520. Template alignment tool 530 generally includes a tool portion 531 and a cam portion 540. Tool portion 531 includes a handle shank 532, an offset portion 534, and a plurality of prongs 536a-b. Handle shank 532 is connected to offset portion 534, and offset portion 534 is connected to prongs 536a-b so that prongs 536a-b are offset from an axis of handle shank 532. Prongs 536a-b are separated by a gap and each include an engagement head 537 at a terminal end thereof. As depicted, engagement heads 537a-b are rounded features that have a greater cross-sectional geometry than the remainder of their respective prongs 536a-b. In this regard, engagement heads 537a-b can be received within corresponding notches 526a-b or 527a-b of baseplate template 520. First prong 536a also includes a cam support member 538 that extends from an inner surface thereof into the gap between first and second prongs 536a-536b.

Figure 31A:
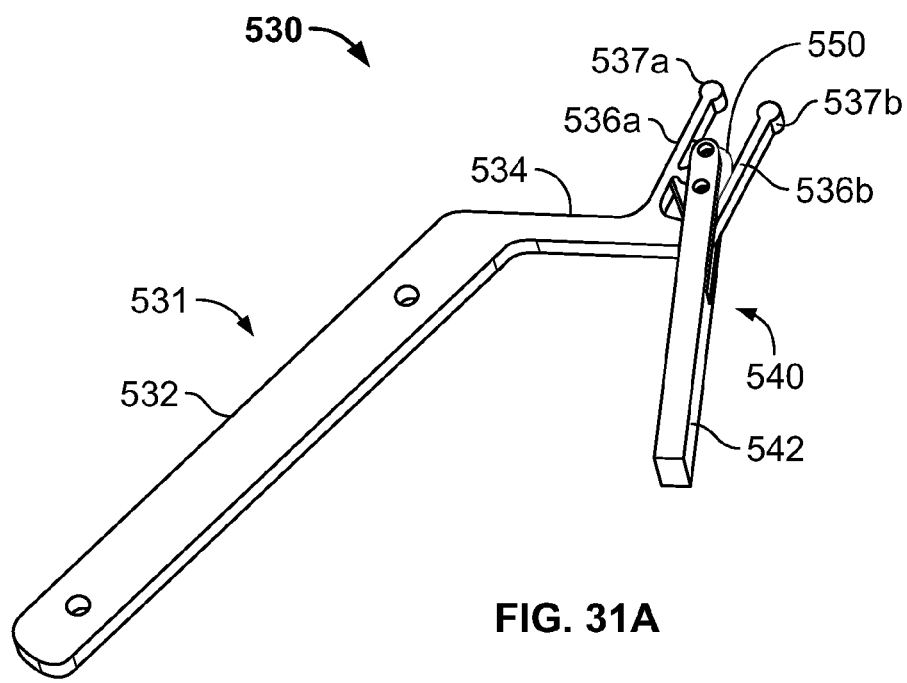
FIG. 31A is a perspective view of a template alignment tool according to an embodiment of the present disclosure.
Figure 31B:
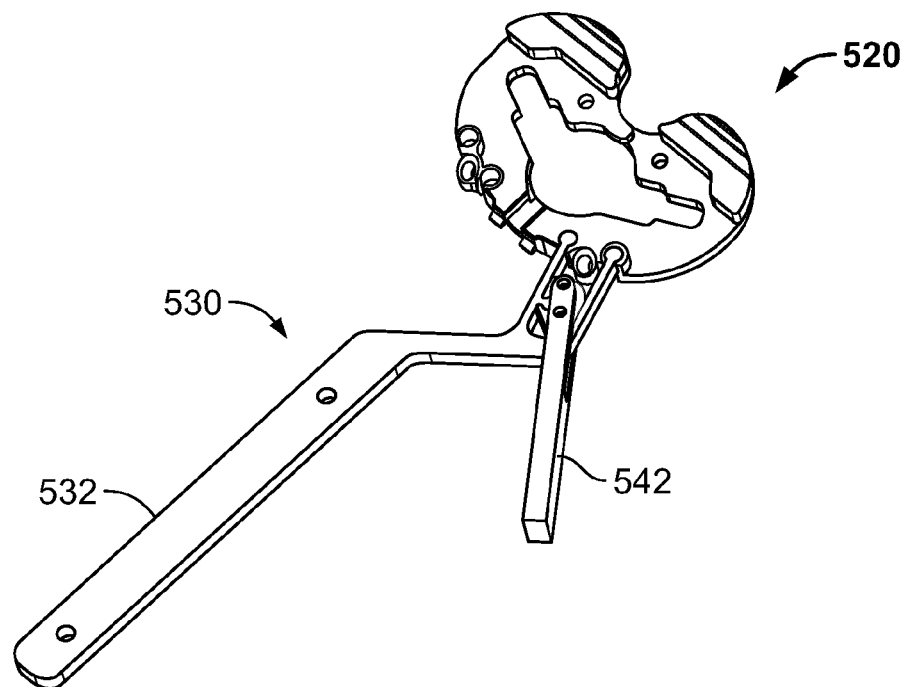
FIGS. 31B and 31C are perspective views of the template alignment tool of FIG. 31A connected to baseplate template of FIG. 30 in a first configuration.
Figure 31C:
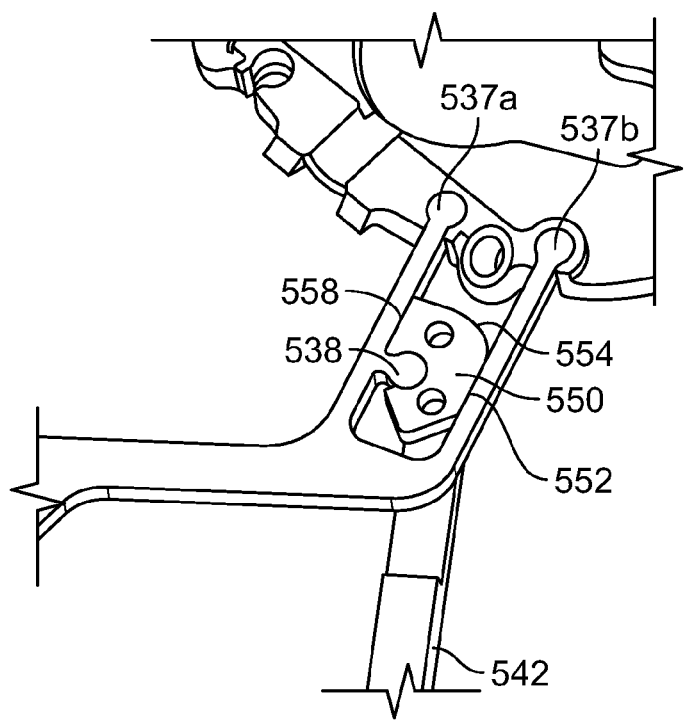
Figure 31D:
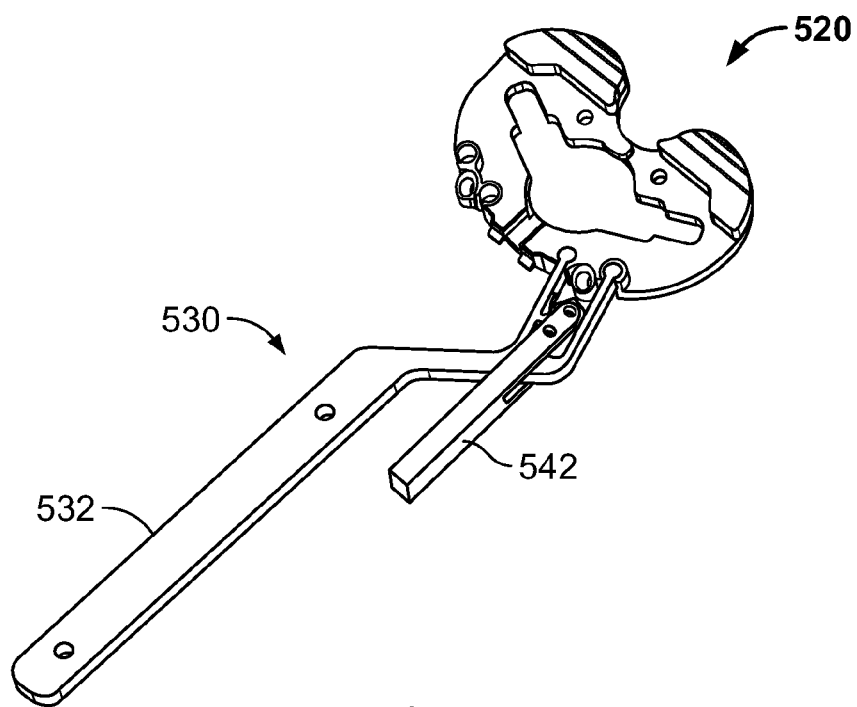
FIGS. 31D and 31E are perspective views of the template alignment tool of FIG. 31A connected to baseplate template of FIG. 30 in a second configuration.
Figure 31E:
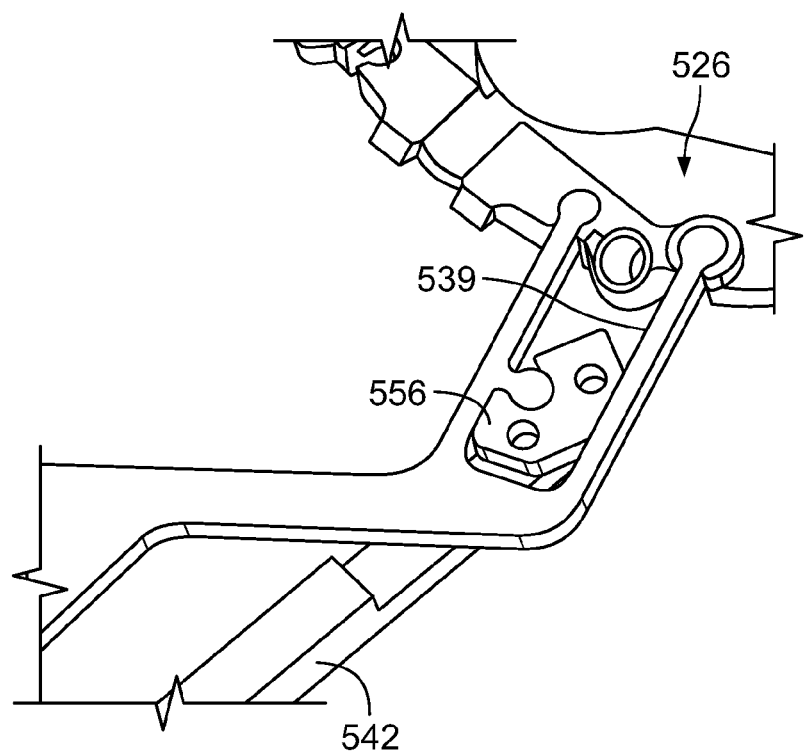

Cam portion 540 includes a handle shank 542 and a cam 550. Cam 550 is connected to an end of handle shank 542 and includes a first cam surface 552, a second cam surface 554, and two stop surfaces 556, 558. Cam 550 is connected to cam support member 538 and is rotatable thereabout. In this regard, cam 550 is positioned within the gap between first and second prongs 536a-b and is rotatable between a first configuration and a second configuration. In the first configuration, which is depicted in FIGS. 31B and 31C, first cam surface 552 abuts an inner surface 539 of second prong 536b and first stop surface 556 contacts an inner surface of first leg 536a. In the second configuration, which is depicted in FIGS. 31D and 31E, handle shank 542 of cam portion 540 is positioned closer to handle shank 532 of tool portion 531 than in the first configuration. Additionally, second cam surface 554 abuts inner surface 539 of second prong 536b and second stop surface 558 abuts the inner surface of first prong 536a. It is noted that in the first configuration, first cam surface 552 is closer to cam support member 538 than second cam surface 554 when cam 550 is in the second configuration. Thus, in the second configuration, cam 550 applies pressure to first and second prongs 536a-b so as to urge first and second prongs 536a-b apart.

In a method of using template alignment tool 530, cam portion 540 is placed in the first configuration and first and second engagement heads 537a-b of prongs 536a-b are inserted into respective first and second notches 526a-b, 527a-b from a proximal side of either first set of notches 526 or second set of notches 527. As depicted, in FIGS. 31B-31D, engagement heads 537a-b are inserted into first set of notches 526a-b. Due to the larger dimension of engagement heads 537a-b relative to the remainder of their respective prongs 536a-b, prongs 536a-b cannot be pulled out of template 520 posteriorly. Once engagement heads 537a-b are placed within notches 526a-b, handle shank 542 is moved toward handle shank 532 of tool portion 531 so as to transition assembly 530 into the second configuration. The force applied by cam 550 on second prong 536b while in the second configuration urges prongs 536a-b apart. However, prongs 536a-b are resisted by template 530 which creates a locking relationship between template 530 and prongs 536a-b. At this point, template 520 can be manipulated via handle shank 532 of tool portion 531. In this regard, template 520 is placed over a resected proximal tibia using tool 530. When in a desired position, pins can be inserted through pin holes including those extending through angled pin sleeves 528 to prevent template 520 from being inadvertently moved. Tool 530 can then be disengaged from template 520 by moving shank handle 542 of cam portion 540 away from shank handle 532 of tool portion 531 to transition assembly 530 back into the first configuration which unlocks prongs 536a-b from template 520 so that they can be removed from notches 526a-b.

Figure 32A:
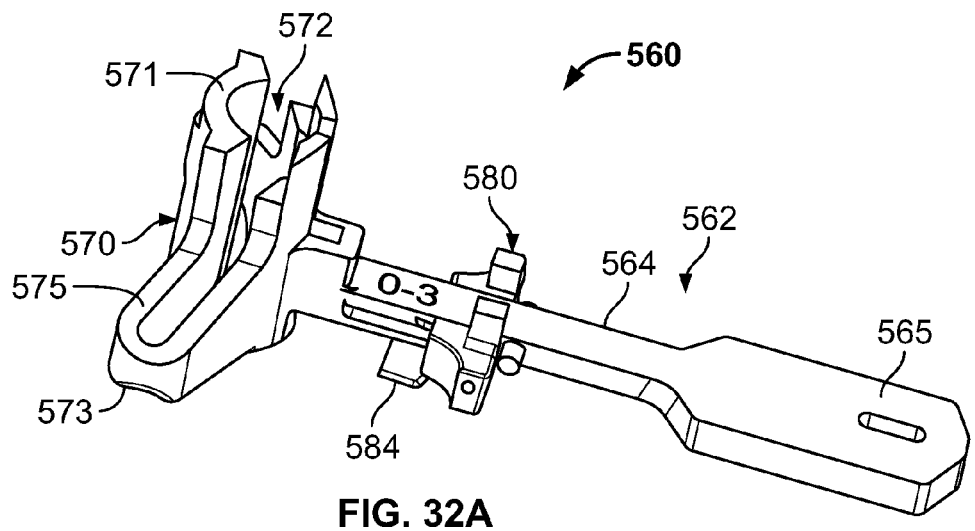
FIG. 32A is a perspective view of a keel punch guide according to an embodiment of the present disclosure.
Figure 32B:
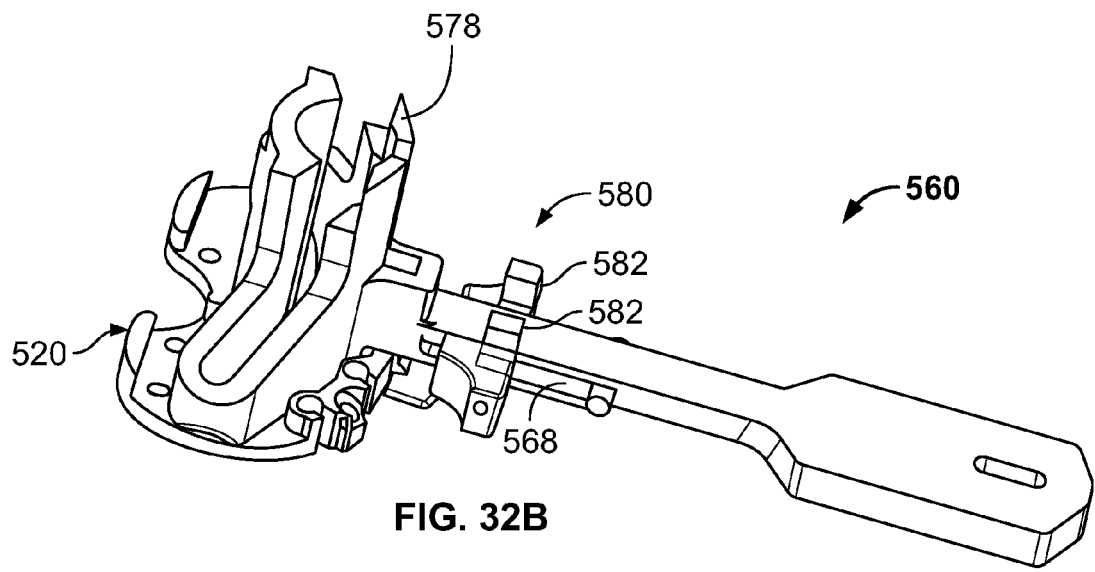
FIG. 32B is a perspective view of an assembly comprised of the keel punch guide of FIG. 32A and the baseplate template of FIG. 30.
Figure 32C:
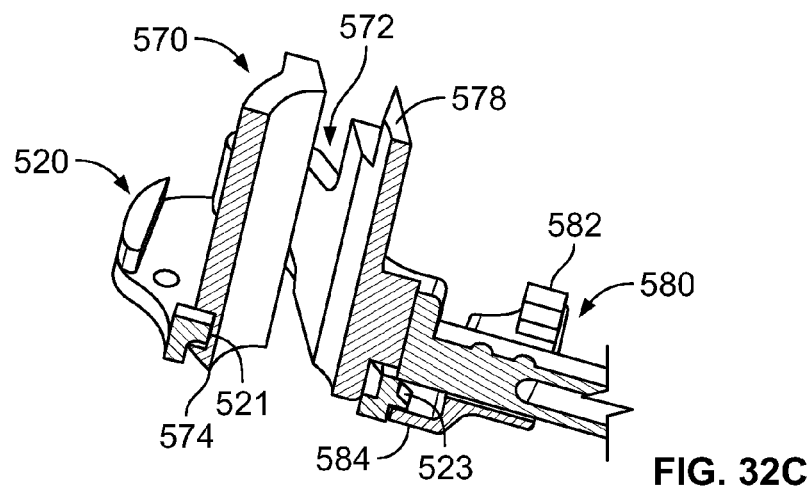
FIG. 32C is a partial cross-sectional view of the assembly of FIG. 31B taken along a midline thereof.

FIGS. 32A-32C depict a keel punch guide assembly 560 according to an embodiment of the present disclosure. Keel punch guide assembly 560 generally includes a handle 562, punch guide 570, and shuttle 580. Punch guide 570 is connected to an end of handle 562 and has an opening 572 that extends therethrough that is in the general shape of a keel punch. Such opening 572 partially defines a sidewall 575 which extends from opening 572 to an exterior of punch guide 575. A flange 578 extends from sidewall 575 at a proximal end 571 of punch guide 570. Also, a hook arm 574 extends from sidewall 571 from a distal end 573 of punch guide 570, as best shown in FIG. 32C.

Handle 562 includes a narrow portion 564 and a wide portion 565. Narrow portion 564 has grooves 568 that are disposed at opposite sides thereof and extend along its length. Shuttle 580 is slidably connected to grooves 568 and can translate along narrow portion 564 toward and away from punch guide 570. Shuttle 580 includes engagement members 582 that project proximally beyond narrow portion 564 when shuttle 580 is connected thereto. Also, a tongue 584 projects from a distal side of shuttle 580 in a direction toward punch guide 570.

Keel punch guide assembly 570 is connectable to baseplate template 520, as best shown in FIGS. 32B and 32C. When connected, punch guide 570 is positioned on proximal surface 523 of template 520 so that guide opening 572 aligns with opening 524 of template 520. In addition, hook arm 521 extends through opening 524 and latches to template 520 from a distal side thereof. Shuttle 580 is also slid into a connection position in which tongue 584 interfaces with a flange 523 of template which traps a portion of template 520 between handle 562 and tongue 523, as best shown in FIG. 32C.

Figure 33A:
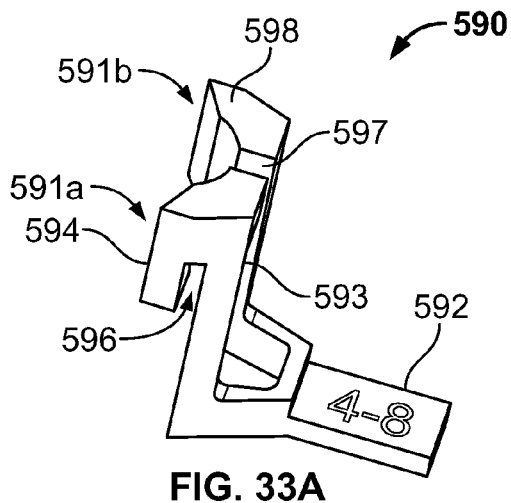
FIG. 33A is a perspective view of a punch guide adaptor according to an embodiment of the present disclosure.
Figure 33B:
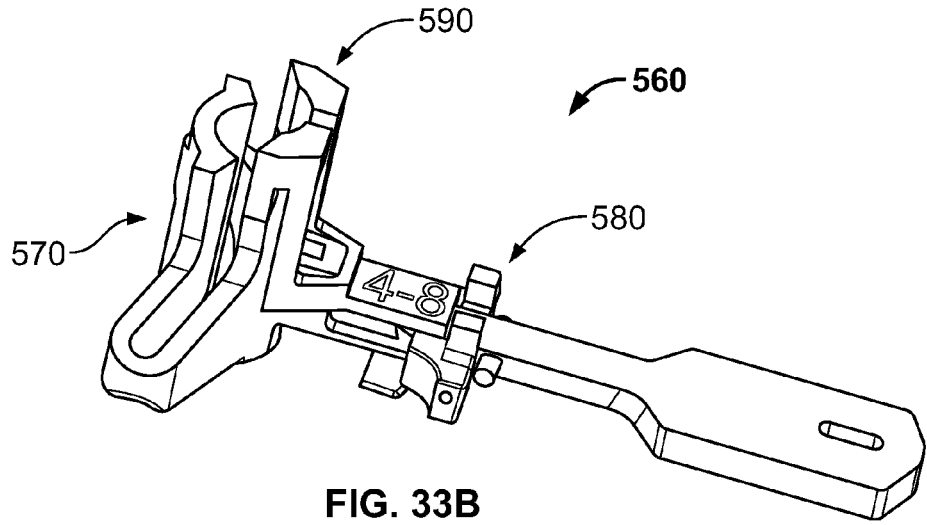
FIGS. 33B is and 33C are perspective views of an assembly comprised of the keep punch guide of FIG. 32A and the punch guide adaptor of FIG. 33A with a shuttle of the keel punch guide being in a first and second position, respectively.
Figure 33C:
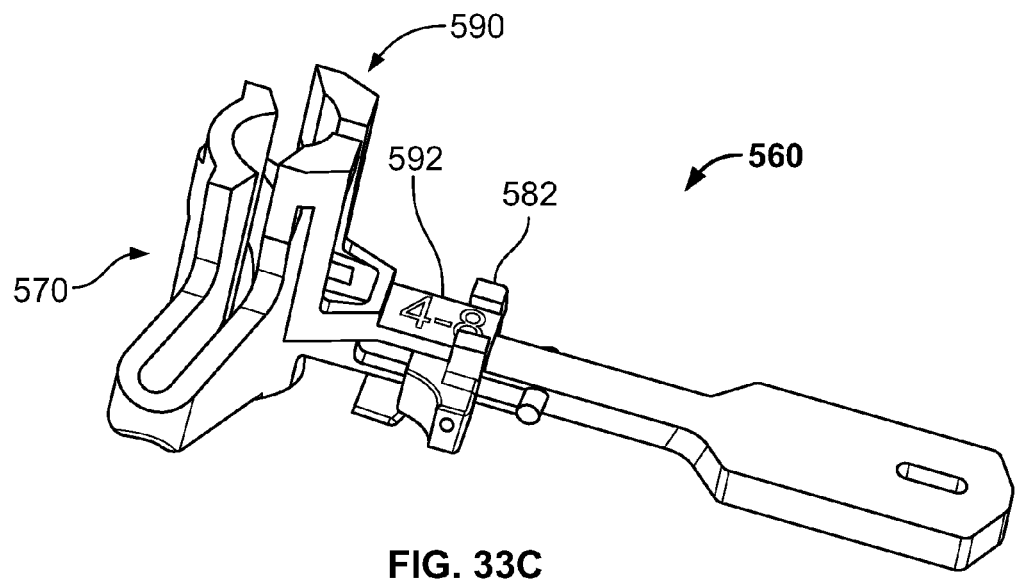

FIGS. 33A-33C depict a punch guide adaptor 590 that can be used in conjunction with punch guide assembly 560. Punch guide adaptor 590 includes a tab 592 and first and second legs 291a-b extend from tab 592. Each leg 591 includes a proximally extending portion 593 and a distally extending portion 594. Proximally and distally extending portions 593, 594 are connected to each other at a knee which defines an abutment surface 598. A recess 596 is disposed between proximally and distally extending portions 593, 594. Additionally, each leg 591a-b is separated by a gap 597 which receives an anti-rotation feature of a keel punch.

Adaptor 590 can be connected to punch guide assembly 560 so as to adjust punching depth in order to account for different sized keels without the need for an entirely different punch guide assembly. In this regard, adaptor 590 is positioned on a proximal end of assembly 560 so that flange 578 of punch guide assembly 560 is disposed in recess 596 of adaptor 590 and tab 592 rests on narrow portion 564 of handle 562. Adaptor 590 is locked into place via engagement members 582 of shuttle 580. In this regard, when shuttle 580 is in its connection position to connect punch guide 570 to baseplate template 520, engagement members 582 trap tab 580 against narrow portion 564 of handle 562 to prevent inadvertent displacement of adaptor 590, as best shown in FIG. 33C.

In a method of using keel punch guide assembly 560 and adaptor 590, once tibial baseplate template 520 is connected to a proximal tibia, as described above, keel punch guide assembly 560 is connected thereto. This is achieved by inserting hook arm 574 through opening 524 of template 520 and connecting hook arm 574 to template 520. Thereafter, shuttle 580 is slid forward toward punch guide 570 until tongue 584 interfaces flange 523 of template 520 thereby locking template 520 to keel punch guide assembly 560. At this point, punch guide assembly 560 is fixed to baseplate template 520. A keel punch (not shown) is then inserted through punch opening 572 and impacted into the proximal tibia to form a keel void in the bone, as is known in the art. The keel punch is impacted until it abuts the proximal end 571 of punch guide 570 which determines the depth of the punch.

Punching a keel void into the proximal tibia can be performed without an adaptor, such as adaptor 590, for certain sizes of implants. For example, keel punch guide assembly 560 can be utilized to punch a keel for size 0-3 tibial implants. However, for other size implants, adaptor 590 may be utilized. For example, adaptor 590 can be used for size 4-8 tibial implants. In this regard, hook arm 574 is connected to baseplate template 520. However, before shuttle 580 is slid into position against template 520, adaptor 590 is placed on proximal end 571 of punch guide 560 so that flange 578 is disposed in recess 596 and tab 592 rests on narrow portion 564 of handle 562. Thereafter, shuttle 580 is slid toward template 570 so that engagement features 582 engage tab 592 holding adaptor 590 in place and tongue 584 interfaces with flange 523 to hold the assembly in place. A punch is then inserted through punch opening 572 until it abuts abutment surface 598 of adaptor 590. In this regard, the punch depth differs relative to that of guide assembly 560 without adaptor 590.

FIGS. 34A-34C depict a tibial insert trial assembly 620 according to an embodiment of the present disclosure. Tibial insert trial assembly 620 generally includes an insert shim 600 and an insert trial 610. Insert shim 600, as best shown in FIG. 34A, includes a post 602 and feet 606a-b. Post 602 defines grooves 604a-b which are disposed at opposite sides of thereof. Such grooves 604a-b extend in an anterior-posterior direction. Feet 606a-b extend from a distal end of post 602 and each includes a protrusion 608 extending from a proximal surface 603 thereof. Such protrusions 608 are positioned adjacent post 602. Additionally, feet 606a-b have a predetermined thickness spanning between proximal surface 603 and a distal surface 605. Such thickness corresponds to an incremental difference in thickness between tibial insert prostheses. For example, if the difference in thickness between a first tibial insert prosthesis and a second tibial insert prosthesis is 5 mm, then the thickness of legs 606a-b may be 5 mm to correspond to this difference.

In this regard, multiple insert shims 600 can be provided in a kit each with varying thicknesses. For example, a first shim can be provided with a leg thickness corresponding to the difference in thickness between tibial insert prostheses that differ by one thickness increment, such as an increment of 5 mm. However, a second insert shim can be provided that has a leg thickness corresponding to a thickness between tibial insert prostheses that differ by more than one thickness increment, for example, 10 mm or two increments of 5 mm.

Tibial insert trial 610, as shown in FIG. 34B, includes a proximal articular surface 614, a distal surface 615, and a post 612. Post 612 extends proximally from articular surface 614. Post 612 is optional as post 612 is typically utilized in stabilized prostheses. However, insert trial 610 could correspond to a posterior cruciate retaining tibial insert prosthesis in which post is not needed. Distal surface 615 has openings (not shown) extending therein which are configured to receive protrusions 608 extending from legs 606a-b. Another larger opening, which is illustrated in FIG. 34C, also extends into distal surface 615 and is configured to receive post 602. First and second openings or prong openings 616a-b extends into an anterior side of insert trial 610. Such openings 616a-b are aligned in a lateral-medial direction. A third opening or pin opening 618 also extends into an anterior side of insert trial 610 and is positioned proximal to and midway between first and second openings 616a-b. However, first and second openings 616a-b only extend in an anterior-posterior direction, while third opening 618 extends in an anterior-posterior direction and also a proximal-distal direction.

When insert shim 600 is assembled to insert trial 610, post 602 and protrusions 608 of shim insert 600 are received in corresponding openings of insert trial 610. In addition, first and second openings 616a-b align with grooves 604a-b of post 602, as best shown in FIG. 34C. Also, distal surface 615 of tibial insert trial 610 rests on proximal surface 603 of feet 606a-b which increases the thickness of tibial insert trial 610 by an amount substantially equal to the thickness of feet 606a-b. Thus, the thickness of tibial insert trial 610 can be incrementally increased to correspond to tibial insert prostheses of various thicknesses.

FIGS. 35A-35D depict a tibial insert tool 630 according to an embodiment of the present disclosure. Tibial insert tool 630 can be used to hold tibial insert trial assembly 620 together while also allowing an operator to easily manipulate assembly 620 so that it can be inserted into a joint space between a femur and tibia. In this regard, tibial insert tool 630 includes a tool portion 640, a lever 650, and a pin assembly 660. Tool portion 640 includes a handle shank 642, a plurality of prongs 648, a pin assembly support 644, and a lever support 646. The plurality of prongs 648 includes first and second prongs 648a-b which extend from an end of handle shank 642. Such prongs 648a-b extend along their own axes which are each generally parallel to an axis defined by handle shank 642.

Pin assembly support 644 and lever support 646 both extend from the same side of shank 642 and in a direction transverse to the shank's axis. Additionally, pin assembly support 644 is disposed closer to prongs 648a-b than lever support 646. Pin assembly support 644 includes a sleeve portion 645 that has longitudinal slots that extend along its length. Lever support 646 includes an axle 647 which is connected to lever 650 such that lever 650 can rotate about axle 647. Lever 650 includes a manipulation portion 652 at one side of axle 647 and a forked portion comprised of prongs 654 at an opposite side of axle 647.

Figure 35A:
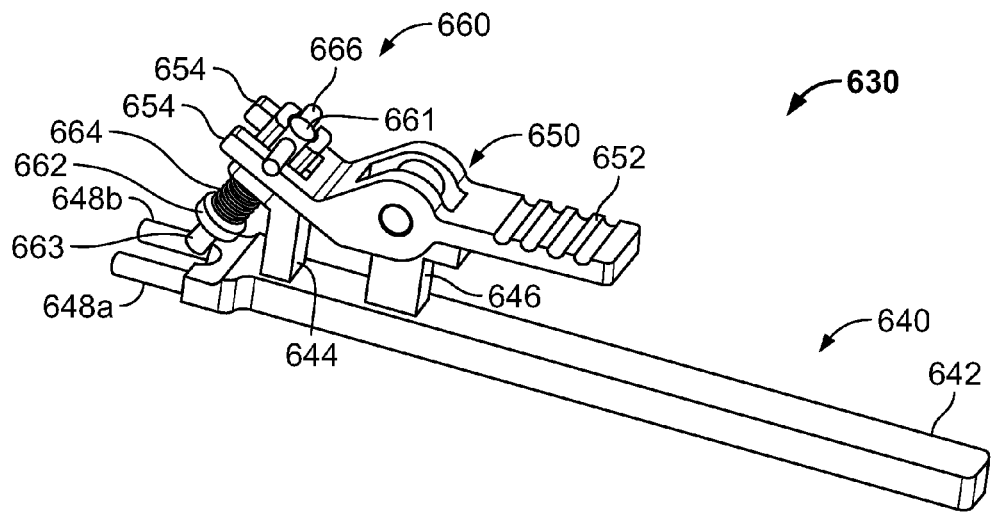
FIG. 35A is a perspective view of a tibial insert tool according to an embodiment of the present disclosure.

Pin assembly 660 includes a pin, spring 664, and transverse shaft 666. Pin includes a pin head 663, a pin shank 661 and a collar 662 disposed between shank 661 and head 663. Transverse shaft 666 extends through pin shank 661 in a direction transverse to the shank's axis. Spring 664 is disposed over pin shank 661. When assembled to pin assembly support 644, shank 661 extends through sleeve 645 while transverse shaft 666 extends through the longitudinal slots of sleeve 645. Additionally, prongs 654 of lever 650 engage transverse pin 647, as illustrated in FIG. 35A. Spring 664 is disposed about pin shank 661 between sleeve 645 and collar 662 of the pin. Pin head 663 extends from collar 662 toward a gap between prongs 648a-b.

Figure 35B:
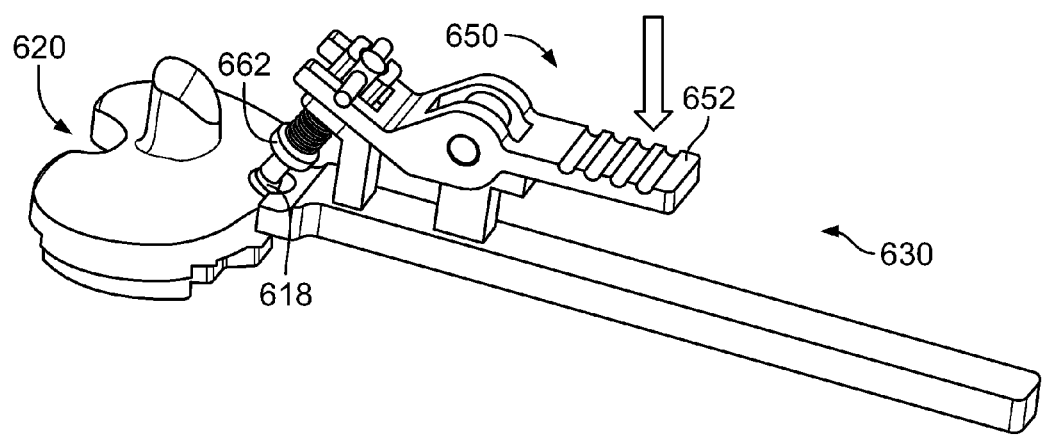
FIG. 35B is a perspective view of an assembly comprised of the insert shim, tibial insert trial, and tibial insert tool of FIGS. 34A, 34B, and 35A, respectively, with the tool being in a first configuration.

In a method of using tibial insert tool 630, lever 650 is pushed toward handle shank 642 which causes prongs 654 to pull on transverse pin 666 so that spring 664 is depressed and pin head 663 moves away from prongs 648a-b of tool portion 640, as best shown in FIG. 35B. At this point, prongs 648a-b of tool portion 640 are inserted through corresponding prong openings 616a-b in tibial insert trial 610 while shim trial 600 is attached thereto. In this regard, prongs 648a-b also extend into grooves 604a-b of post 602. Grooves 604a-b are formed so that when prongs 648a-b are inserted into grooves 604a-b and into prong openings 616a-b, insert trial 610 is prevented from being disconnected from shim trial 600.

Figure 35C:
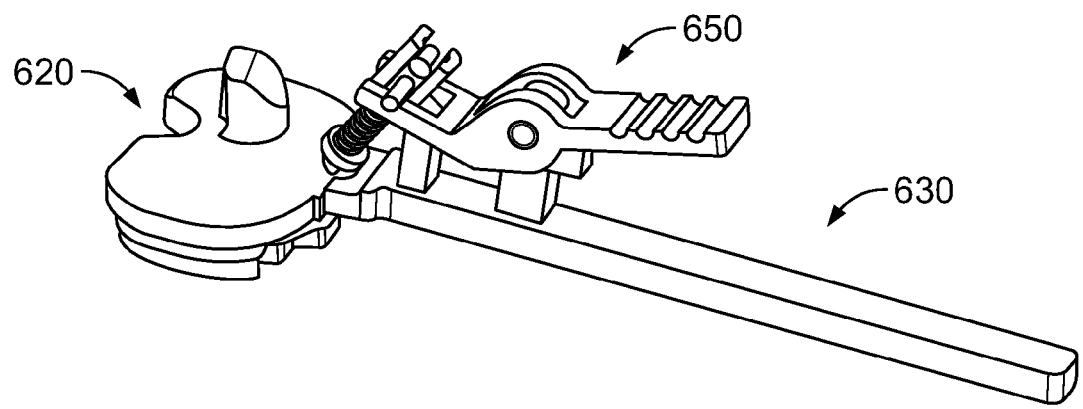
FIG. 35C is a perspective view of the assembly of FIG. 35B with the tool being in a second configuration.
Figure 35D:
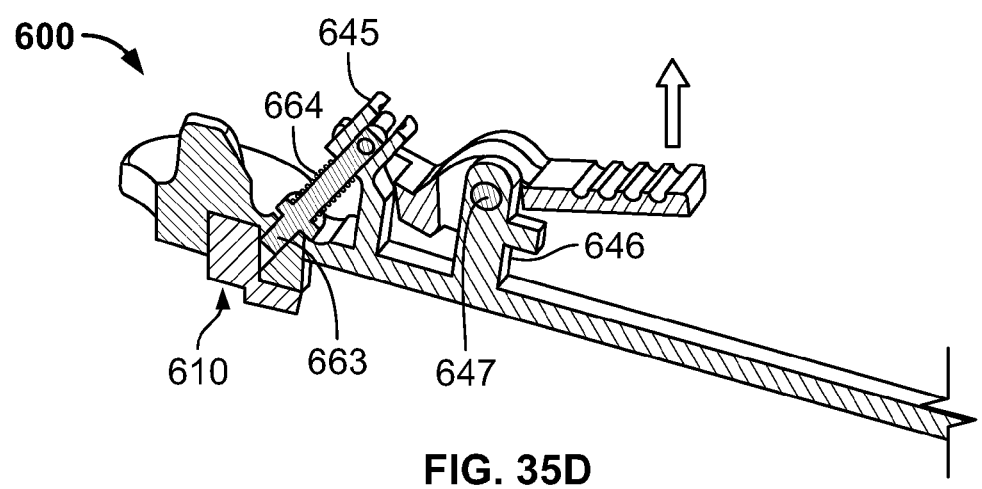
FIG. 35D is a partial cross-sectional view of the assembly of FIG. 35C.

Thereafter, lever 650 is released and the natural bias of spring 664 pushes pin head 663 into pin opening 618 of insert trial 610, as best shown in FIGS. 35C and 35D. Due to the angle of pin opening 618, pin head 663 engaging with insert trial 610 prevents prongs 648a-b from being inadvertently removed from first and second openings 616a-b. In this regard, tibial insert trial assembly 620 is locked to tibial insert tool 630 which can be manipulated from handle shank 642 so that trial assembly 620 can be inserted into a joint space between a tibia and femur.

Figure 36A:
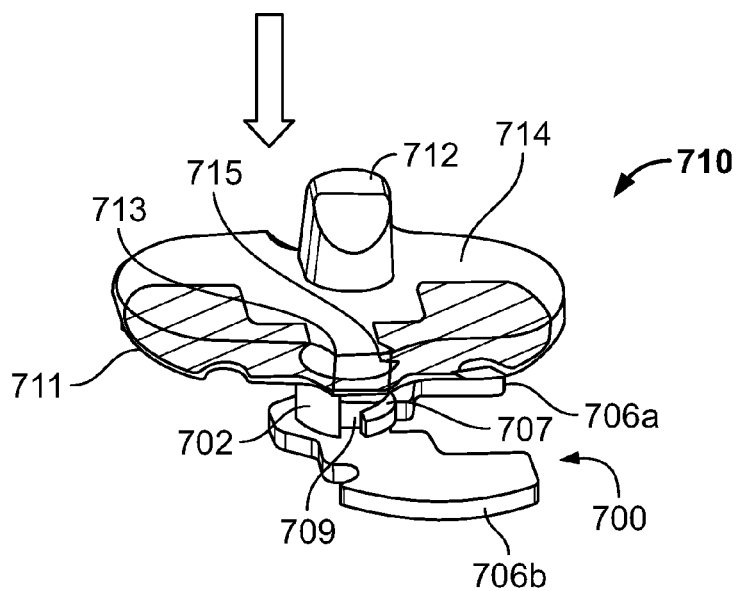
FIGS. 36A-36C depict a method of connecting an insert shim and tibial insert trial according to a further embodiment of the present disclosure.
Figure 36B:
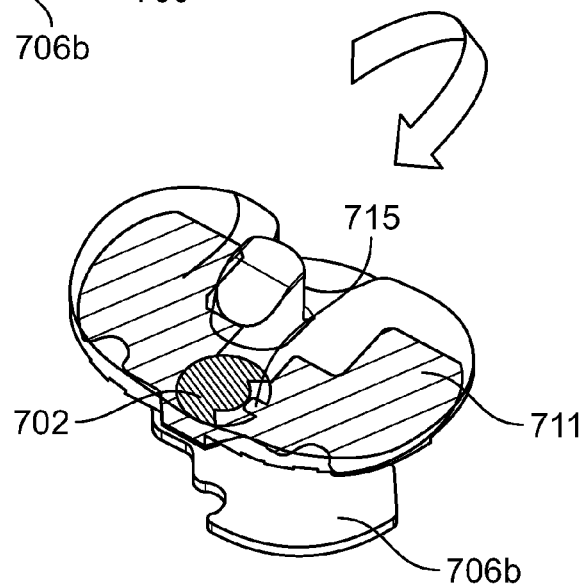
Figure 36C:
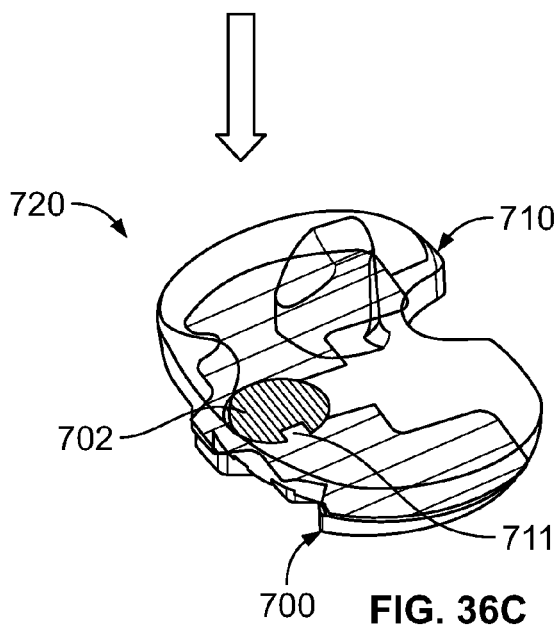

FIGS. 36A-36C depict tibial insert trial assembly 720 according to a further embodiment of the present disclosure. Tibial insert trial assembly 720 is similar to tibial insert trial assembly 620 in that it includes a shim insert 700 and an insert trial 710. However, insert trial assembly 720 differs with regard to the mechanism connecting the two components 700 and 710. In the embodiment depicted, shim insert 700 is connected to tibial insert trial 710 via a bayonet connection.

More particularly, shim trial 700 includes a post 702 and feet 706a-b extending from post 702. Feet 706a-b have a thickness that corresponds to an incremental difference in thickness between tibial insert prostheses, as describe above with regard to shim insert 600. Post 702 includes a first vertical slot, a second vertical slot 709 and a horizontal slot 707. The first vertical is not shown. However, first and second vertical slots intersect horizontal slot 709 such that second vertical slot 709 is offset from the first vertical slot.

Insert trial 710 includes a proximal articular surface 714 and a distal surface. In FIGS. 36A-36C, distal surface 711 of insert trial 710 is shown schematically on a proximal side of insert trial 710. Distal surface 711 of insert trial 710 includes a post opening 713 that that is configured to receive post 702 of shim trial 700. A key 715 extends into post opening 713 and is configured to be received in the vertical and horizontal slots 709, 707 of post 702.

Thus, in a method of assembly, insert trial 710 is rotated relative to shim insert 700 so that key 715 aligns with the first vertical slot, as illustrated in FIG. 36A. Key 715 is inserted into such slot until it enters into horizontal slot 707. Insert trial 710 is then rotated about 90 degrees so that key 715 translates through horizontal slot 707 until it reaches second vertical slot 709, as best shown in FIG. 36B. Once key 715 reaches second vertical slot 709, key 715 is advanced therethrough until distal surface 711 of insert trial 710 comes to rest on feet 706*a-b*, as shown in FIG. 36C. In this regard, shim insert 700 is connected to insert trial 710 and increases the thickness of tibial insert trial 710 by a predetermined amount.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A varus-valgus alignment instrument, comprising:
a body having a bone contact surface for contacting a distal femur and an opening extending through the body and bone contact surface, the opening being sized to receive an elongate shaft therein; and
an alignment member moveably attached to the body and having first and second openings therethrough, each of the first and second openings being sized to receive the elongate shaft and being interchangeably positioned in alignment with the opening of the body,
wherein when the opening of the body is aligned with the first opening, the opening of the body and first opening define a first axis having a first angle relative to the bone contact surface, and
when the opening of the body is aligned with the second opening, the opening of the body and second opening define a second axis having a second angle relative to the bone contact surface, the first angle is not equal to the second angle.

2. The alignment instrument of claim 1, wherein the first angle is one of four, five, six, and seven degrees, and the second angle is one of four, five, six, and seven degrees.

3. The alignment instrument of claim 2, wherein the alignment member includes a third opening extending therethrough and the first, second and third openings are positioned adjacent one another along a circular arc.

4. The alignment instrument of claim 1, wherein the opening includes first and second portions, the first portion is defined by a circular rim and the second portion is defined by an ovular boss.

5. The alignment instrument of claim 4, wherein the first portion is dimensioned to receive the elongate shaft therein such that the elongate shaft, when received by the opening of the body, is pivotable about the rim and moveable from one side of the second portion to a second side thereof as the elongate shaft pivots about the rim.

6. The alignment instrument of claim 1, wherein the alignment member is rotatably connected to the body.

7. The alignment instrument of claim 6, wherein the body includes an extension member extending therefrom, and the alignment member is rotatably connected to the extension member, the extension member defining a rotation axis.

* * * * *